(12) United States Patent
Karaborni et al.

(10) Patent No.: US 8,722,733 B2
(45) Date of Patent: *May 13, 2014

(54) LEVODOPA PRODRUG MESYLATE HYDRATE

(71) Applicant: XenoPort, Inc., Santa Clara, CA (US)

(72) Inventors: Sami Karaborni, Cupertino, CA (US);
Manshiu Leung, Daly City, CA (US);
Chen Mao, Redwood City, CA (US);
Venkat R. Thalladi, Santa Clara, CA (US)

(73) Assignee: XenoPort, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/769,625

(22) Filed: Feb. 18, 2013

(65) Prior Publication Data

US 2013/0184344 A1 Jul. 18, 2013

Related U.S. Application Data

(62) Division of application No. 12/581,810, filed on Oct. 19, 2009, now Pat. No. 8,399,513.

(60) Provisional application No. 61/106,937, filed on Oct. 20, 2008.

(51) Int. Cl.
*A61K 31/24* (2006.01)

(52) U.S. Cl.
USPC .......................................... 514/517; 514/533

(58) Field of Classification Search
USPC .................................. 514/517, 533
See application file for complete search history.

(56) References Cited

U.S. PATENT DOCUMENTS

| | | | |
|---|---|---|---|
| 3,811,444 A | 5/1974 | Heller et al. | |
| 3,845,770 A | 11/1974 | Theeuwes et al. | |
| 3,916,899 A | 11/1975 | Theeuwes et al. | |
| 3,962,414 A | 6/1976 | Michaels | |
| 3,992,518 A | 11/1976 | Chien et al. | |
| 4,038,411 A | 7/1977 | Saari | |
| 4,066,747 A | 1/1978 | Capozza | |
| 4,070,347 A | 1/1978 | Schmitt | |
| 4,079,038 A | 3/1978 | Choi et al. | |
| 4,083,949 A | 4/1978 | Benedikt | |
| 4,093,709 A | 6/1978 | Choi et al. | |
| 4,134,991 A | 1/1979 | Wermuth | |
| 4,180,509 A | 12/1979 | Metcalf et al. | |
| 4,311,706 A | 1/1982 | Bodor et al. | |
| 4,663,349 A | 5/1987 | Repta | |
| 4,771,073 A | 9/1988 | Repta | |
| 4,826,875 A | 5/1989 | Chiesi | |
| 4,873,263 A | 10/1989 | Repta | |
| 4,879,303 A | 11/1989 | Davison et al. | |
| 4,914,222 A | 4/1990 | Budavari et al. | |
| 4,966,915 A | 10/1990 | Tsuchiya et al. | |
| 4,983,400 A | 1/1991 | Dempski et al. | |
| 5,017,607 A | 5/1991 | Chiesi | |
| 5,057,321 A | 10/1991 | Edgren et al. | |
| 5,073,641 A | 12/1991 | Bundgaard et al. | |
| 5,128,145 A | 7/1992 | Edgren et al. | |
| 5,133,974 A | 7/1992 | Paradissis et al. | |
| 5,190,763 A | 3/1993 | Edgren et al. | |
| 5,283,352 A | 2/1994 | Backstrom et al. | |
| 5,332,576 A | 7/1994 | Mantelle | |
| 5,462,933 A | 10/1995 | Kramer et al. | |
| 5,580,904 A | 12/1996 | Ishikura et al. | |
| 5,607,969 A | 3/1997 | Milman et al. | |
| 5,637,780 A | 6/1997 | Jadhav et al. | |
| 5,698,155 A | 12/1997 | Grosswald et al. | |
| 5,725,883 A | 3/1998 | Staniforth et al. | |
| 5,827,819 A | 10/1998 | Yatvin et al. | |
| 5,840,756 A | 11/1998 | Cohen et al. | |
| 6,696,600 B2 | 2/2004 | Frenkel et al. | |
| 7,008,950 B1 | 3/2006 | Ohkawa et al. | |
| 7,101,912 B2 | 9/2006 | Xiang et al. | |
| 7,323,585 B2 | 1/2008 | Xiang et al. | |
| 7,342,131 B2 | 3/2008 | Xiang et al. | |
| 7,534,813 B2 | 5/2009 | Xiang et al. | |
| 7,563,821 B2 | 7/2009 | Xiang et al. | |
| 7,671,089 B2 | 3/2010 | Xiang et al. | |
| 7,709,527 B2 | 5/2010 | Xiang et al. | |
| 7,829,592 B2 | 11/2010 | Xiang et al. | |
| 7,893,105 B2 * | 2/2011 | Xiang et al. | ................... 514/517 |
| 7,956,212 B2 | 6/2011 | Xiang et al. | |
| 7,968,597 B2 | 6/2011 | Xiang et al. | |

(Continued)

FOREIGN PATENT DOCUMENTS

CA          2607198         11/2006
DE   10 2005 022 276 A1    11/2006

(Continued)

OTHER PUBLICATIONS

Airaksinen et al., Excipient selection can significantly affect solid-state phase transformation in formulation during wet granulation. *AAPS PharmSciTech* 2005, 6(2), E311-E322.

Alpert and Friedhoff, Paradoxical reaction to L-dopa in schizophrenic patients, *Am J Psychiatry*, 1978, 135(11), 1329-1332.

Bai, pGlu-L-Dopa-Pro: A tripeptide prodrug targeting the intestinal peptide transporter for absorption and tissue enzymes for conversion, Pharm. Res. 1995, 27(7), 1101-1104.

Berge et al., Pharmaceutical salts, *J. Pharm. Sci*, 1977, 66(1), 1-19.

Betarbet et al., Animal models of Parkinson's disease, *Bioessays*, 2002, 24(4), 308-318.

Bodor et al. Improved delivery through biological membranes. 4. Prodrugs of L-Dopa, *J. Med. Chem.*, 1977, 20(11), 1435-1445.

(Continued)

*Primary Examiner* — Rei-tsang Shiao

(74) *Attorney, Agent, or Firm* — Kilpatrick Townsend & Stockton LLP

(57) ABSTRACT

Crystalline (2R)-2-phenylcarbonyloxypropyl (2S)-2-amino-3-(3,4-dihydroxyphenyl)propanoate mesylate, hydrate, methods of making the hydrate, pharmaceutical compositions containing the hydrate, and methods of using the hydrate to treat diseases or disorders such as Parkinson's disease are provided.

19 Claims, 13 Drawing Sheets

(56) References Cited

U.S. PATENT DOCUMENTS

| | | |
|---|---|---|
| 8,163,958 B2 | 4/2012 | Xiang et al. |
| 2002/0099041 A1 | 7/2002 | Gallop et al. |
| 2003/0152628 A1 | 8/2003 | Licht et al. |
| 2003/0158254 A1 | 8/2003 | Zerangue et al. |
| 2005/0209181 A1 | 9/2005 | Akil et al. |
| 2005/0209246 A1 | 9/2005 | Ueda et al. |
| 2005/0282891 A1 | 12/2005 | Xiang et al. |
| 2006/0020028 A1 | 1/2006 | Xiang et al. |
| 2007/0225366 A1 | 9/2007 | Xiang et al. |
| 2008/0070984 A1 | 3/2008 | Tran et al. |
| 2008/0103200 A1 | 5/2008 | Xiang et al. |
| 2008/0132570 A1 | 6/2008 | Xiang et al. |
| 2008/0171789 A1 | 7/2008 | Xiang et al. |
| 2008/0214663 A1 | 9/2008 | Xiang et al. |
| 2009/0137834 A1 | 5/2009 | Xiang et al. |
| 2009/0156679 A1 | 6/2009 | Xiang et al. |
| 2009/0325061 A1 | 12/2009 | Xiang et al. |
| 2010/0099761 A1 | 4/2010 | Karaborni et al. |
| 2010/0099907 A1 | 4/2010 | Raillard et al. |
| 2010/0173992 A1 | 7/2010 | Xiang et al. |
| 2010/0226855 A1 | 9/2010 | Nangia et al. |
| 2011/0028544 A1 | 2/2011 | Xiang et al. |
| 2011/0111024 A1 | 5/2011 | Mao et al. |
| 2011/0111062 A1 | 5/2011 | Xiang et al. |
| 2011/0201817 A1 | 8/2011 | Xiang et al. |

FOREIGN PATENT DOCUMENTS

| | | |
|---|---|---|
| EP | 0309827 B1 | 4/1989 |
| GB | 1447599 | 8/1976 |
| GB | 1537951 | 1/1979 |
| JP | 58-024547 | 2/1983 |
| WO | 86/04579 | 8/1986 |
| WO | 88/01615 | 3/1988 |
| WO | 01/68065 A2 | 9/2001 |
| WO | 02/28882 A1 | 4/2002 |
| WO | 2005/121069 A1 | 12/2005 |
| WO | 2005/121070 A1 | 12/2005 |
| WO | 2007/067495 | 6/2007 |
| WO | 2007/087256 A2 | 8/2007 |

OTHER PUBLICATIONS

Boivin and Montplaisir, The effects of L-dopa on excessive daytime sleepiness in Narcolepsy, *Neurology*, 1991, 41, 1267-1269.

Bonelli and Wenning, Pharmacological management of Huntington's disease: an evidence-based review, *Current Pharmaceutical Design*, 2006, 12(21), 2701-2720.

Bruno and Bruno, Effects of L-dopa on pharmacological parkinsonism, *Acta Psychiatr Scand*, 1966, 42(3), 264-271.

Buchanan et al., Double blind trial of L-dopa in chronic schizophrenia, *Aust N Z J Psychiatry*, 1975, 9(4), 269-271.

Carboxylic Acid Derivatives and Nitriles, http://www.chem.uky.edu/Courses/che232/JEA!In/9.%20Esters etc.pdf, retrieved Mar. 24, 2010.

Cho et al., Dopamine neurons derived from embryonic stem cells efficiently induce behavioral recovery in a Parkinsonian rat model, *Biochemical ad Biophysical Research Communication*, 2006, 341(1), 6-12.

Coleman et al., A practical guide to polymer miscibility, *Polymer Reviews*, 1990, 31, 1187-1203.

Conti et al., Levodopa for idiopathic restless legs syndrome: evidence-based review, *Mot Disord*, 2007, 22(13), 1943-1951.

Cools, Dopaminergic modulation of cognitive function-implications for L-dopa treatment in Parkinson's disease, *Neuroscience Biobehavioral Rev*, 2006, 30, 1-23.

Cooper et al., L-Dopa esters as potential prodrugs: behavioural activity in experimental models of Parkinson's disease, *J. Pharma Pharmacology*, 1987, 39, 627-635.

Davey et al., Polymorphism in molecular crystals: stabilization of a metastable form by conformation mimicry, *J Am Chem Soc* 1997, 119(7), 1767-1772.

Di Stefano et al., Dimeric L-dopa derivatives as potential prodrugs, *Bioorganic & Medicinal Chem. Lett.*, 2001, 11, 1085-1088.

Doggrell, The therapeutic potential of dopamine modulators on the cardiovascular and renal systems, *Expert Opin. Investig., Drugs*, 2002, 11 (5), 631-644.

Durif et al., Worsening of levodopa-induced dyskinesias by motor and mental tasks, *Movement Disorders*, 1999, 14(2), 242-245.

During, Controlled release of dopamine from a polymeric brain implant: In vivo characterization, *Ann. Neurol.*, 1989, 25(4), 351-356.

Ebadi and Srinivasan, Pathogenesis, prevention and treatment of neuroleptic-induced movement disorders, *Pharmacological Reviews*, 1995, 47(4), 575-604.

Eltayb et al., Enhanced cortical dopamine output and antipsychotic-like effect of raclopride with adjunctive low-dose L-dopa. *Biol Psychiatry*, 2005, 58, 337-343.

Emborg, Evaluation of animal models of Parkinson's disease for neuroprotective strategies, *Journal of Neuroscience Methods*, 2004, 139(2), 121-143.

Fahn et al., Levodopa and the progression of Parkinson's disease, *N Engl J Med*, 2004, 351 (24), 2498-2508.

Faulkner et al., Gabapentin for the treatment of tremor, *The Annals of Pharmacotherapy*, 2003, 37(2), 282-286.

Fincher, Particle size of drugs and Its relationship to absorption and activity, *Journal of Pharmaceutical Sciences*, 1968, 57(11), 1825-1835.

Fix et al., A comparison of oral and rectal absorption of L-dopa ester in rats and mice, *Pharmaceutical Research*, 1990, 7(4), 384-387.

Fix et al., Short-chain alkyl esters of L-dopa as prodrugs for rectal absorption, *Pharmaceutical Research*, 1989, 6(6), 501-505.

Floel et al., Dopaminergic effects on encoding of a motor memory in chronic stroke, *Neurology*, 2005, 65(3), 472-474.

Floel et al., Levodopa increases memory encoding and dopamine release in the striatum in the elderly, *Neurobiology of Aging*, 2008, PMID 17098331.

Folstein et al., Mini-mental state. A practical method for grading the cognitive state of patients for the clinician, *J. Psychiat. Res.*, 1975, 12(3), 189-198.

Garcia-Borreguero et al., Treatment of restless legs syndrome with gabapentin: a double-blind, cross-over study, *Neurol*, 2002, 11(2), 1573-79.

Garzon-Aburbeh et al., A lymphotropic prodrug of L-Dopa: Synthesis, pharmacological properties, and pharmacokinetic behavior of 1,3-dihexadecanoyi-2-[(S)-2-amino-3-(3,4-dihydroxyphenyl)propanoyl]propane-1,2,3-triol, *J. Med. Chem.*, 1986, 29, 687-691.

Gelb et al., Diagnostic criteria for Parkinson disease, *Arch Neurol*, 1999, 56(1), 33-39.

Gerlach and Luhdorf, The effect of L-dopa on young patients with simple schizophrenia, treated with neuroleptic drugs, *Psychopharmacologia*, 1975, 44(1), 105-110.

Gibb et al., The relevance of the Lewy body to the pathogenesis of idiopathic Parkinson's disease, *J Neurol Neurosurg Psychiatry*, 1988, 51(6), 745-752.

Giovannoni et al., Bradykinesia akinesia incoordination test (BRAIN TEST): An objective computerized assessment of upper limb motor function, *J Neurol Neurosurg Psychiatry*, 1999, 67, 624-629.

Hirsch et al., Animal models of Parkinson's disease in rodents induced by toxins: an update, *J. Neural Transm Suppl*, 2003, 65, 89-100.

Hisaka et al., Absorption of a novel product of L-Dopa, L-3-(3-hydroxy-4-pivaloyloxphenyl) alanine (NB-355), In vitro and in situ studies, *Drug Metabolism and Disposition*, 1990, 18(5), 621-625.

Hoes et al., The application of drug-polymer conjugates in chemotherapy, *Drug Carrier System*, 1989, 9, 57-100.

Hogl et al., Increased daytime sleepiness in Parkinson's disease: a questionnaire survey, *Movement Disorders*, 2003, 18(3), 319-323.

Howard et al., Intracerebral drug delivery in rats with lesion-induced memory deficits, *J Neurosurg*, 1989, 71, 105-112.

Inanaga et al., Double-blind controlled study of L-dopa therapy in schizophrenia, *Folia Psychiatr Neurol Jpn*, 1975, 29(2), 123-143.

Ishikura et al., Database CAS citation 1995:365090 [retrieved Nov. 23, 2009] from STN; Columbus, OH USA.

(56) References Cited

OTHER PUBLICATIONS

Ishikura et al., Drug delivery to the brain. DOPA prodrugs based on a ring-closure reaction to quaternary thiazolium compounds, *Int'l. J. Pharmaceutics*, 1995, 116, 51-63.

Jankovic, Treatment of dystonia, *Lancet Neurol*, 2006, 5(10), 864-872.

Jaskiw and Popli, A meta-analysis of the response to chronic L-dopa in patients with schizophrenia: therapeutic and heuristic implications, *Psychopharmacology*, 2004, 171, 365-374.

Juncos et al., Levodopa methyl ester treatment of Parkinson's disease, *Neurology*, 1987, 37, 1242-1245.

Kay and Opler, L-dopa in the treatment of negative schizophrenic symptoms: a single-subject experimental study, *Int'l J Psychiatry Med*, 1985-86, 15(3), 293-298.

Knecht et al., Levodopa: faster and better word learning in normal humans, *Ann. Neurol*, 2004, 56(1), 20-26.

Kulisevsky, Role of dopamine in learning and memory: implications for the treatment of cognitive dysfunction in patients with Parkinson's disease, *Drugs Aging*, 2000, 16(5), 365-379.

Langer and Peppas, Chemical and physical structure of polymers as carriers for controlled release of bioactive agents: a review. *JMS-Rev. Macromol. Chem. Phys.* 1983, C23(1), 61-126.

Langer, Medical applications of controlled release, *Science*, 1983, C23(1), 61-126.

Langer, New methods of drug delivery, *Science*, 1990, 249, 1527-1533.

Leong and Langer, Polymeric controlled drug delivery, *Advanced Drug Delivery Reviews*, 1987, 1, 199-233.

Leppert et al., The effects of carbidopa dose and time and route of administration on systemic L-dopa levels in rats, *Pharmaceuticals Res.*, 1988, 5(9), 587-591.

Levy et al., Inhibition of calcification of bioprosthetic heart valves by local controlled-release diphosphonate, *Science*, 1985, 28, 190-192.

Lu and Yu, Dimensionless presentation for drug release from a coated pure drug bead: 2. Experiment, *Int. J. Pharm.*, 1994, 112, 117-124.

Ludatscher, Stable remission of tardive dyskinesia by L-dopa, *J Clin Psychopharm*, 1989, 9(1), 39-41.

Manson et al., An ambulatory dyskinesia monitor, *J. Neurol. Neurosurg. Psychiatry*, 2000, 68(2), 196-201.

Marrel et al., L-DOPA esters as potential prodrugs, *Eur. Journal Med. Chem. Chim. Ther.*, 1985, 5, 459-465.

Movement Disorder Society Task Force on Rating Scales for Parkinson's Disease. The Unified Parkinson's Disease Rating Scale (UPDRS): Status and Recommendations, *Movement Disorders*, 2003, 18(7), 738-750.

Nutt, Response to levodopa treatment in dopa-responsive dystonia, *Arch Neurol*, 2001, 58, 905-910.

O'Neill et al., LY503430: Pharmacology, pharmacokinetics, and effects in rodent models of Parkinson's disease, *CNS Drug Reviews*, 2005, 11(1), 77-96.

Olanow et al., Drug insight: continuous dopaminergic stimulation in the treatment of Parkinson's disease. *Nat Clin Pract Neurol* 2006, 2(7), 382-92.

Olson et al., Gabapentin for Parkinsonism: A double-blind, placebo-controlled, Crossover trial, *Am. J. Med.*, 1997, 102(1), 60-66.

Ondo and Jankovic, Restless legs syndrome: clinicoetiologic correlates, *Neurology*, 1996, 47(6), 1435-1441.

Orth and Tabrizi, Models of Parkinson's disease, *Movement Disorders*, 2003, 18(7), 729-737.

O'Suilleabhain and Dewey, Contributions of dopaminergic drugs and disease severity to daytime sleepiness in Parkinson disease, *Arch. Neurol*, 2002, 59, 986-989.

Paus et al., Sleep attacks, daytime sleepiness, and dopamine agonists in Parkinson's disease, *Movement Disorders*, 2003, 18(6), 659-667.

Racette and Perlmutter, Levodopa responsive parkinsonism in an adult with Huntington's Disease, *J Neurol Neurosurg Psychiatry*, 1998, 65(4), 577-579.

Rascol and Fabre, 2001, Dyskinesia: L-Dopa-induced and tardive dyskinesia, *Clinical Neuropharmacology*, 2001, 24(6), 313-323.

Sasahara et al., Dosage form design for Improvement of bioavailability of levodopa II: bioavailability of marketed levodopa preparations in dogs and Parkinsonian patients, *Journal of Pharmaceutical Sciences*, 1980, 69(3), 261-265.

Saudek et al., A preliminary trail of the programmable implantable medication system for insulin delivery, *New England Journal of Medicine*, 1989, 321 574-579.

Scheidtmann et al., Effect of levodopa in combination with physiotherapy on functional motor recovery after stroke: a prospective, randomized, double-blind study, *Lancet*, 2001, 358(9284), 787-790.

Schneider et al., Familial dopa-responsive cervical dystonia, *Neurology*, 2006, 66(4), 599-601.

Sefton, Implantable pumps, *CRC Crit. Rev. Biomed. Eng.*, 1987, 14(3), 201-240.

Silber, Sleep disorders, *Neurologic Clin*, 2001, 19(1), 173-186.

Soares and McGrath, The treatment of tardive dyskinesia—a systematic review and meta-analysis, *Schizophrenia Research*, 1999, 39, 1-16.

Staab et al., Control of polymorphism by 'tailor-made' polymeric crystallization auxiliaries. Preferential precipitation of a metastable polar form for second harmonic generation, *Adv Mater* 1990, 2(1), 40-43.

Tang et al., Synthesis and characterization of water-soluble and photostable L-dopa dendrimers, *Organic Letters*, 2006, 8(20), 4421-4424.

Tolwani et al., Experimental models of Parkinson's disease: Insights from many models, *Laboratory Animal Science*, 1999, 49(4), 363-371.

Van Blercom et al., Effects of gabapentin on the motor response to levodopa: A double blind, placebo-controlled, crossover study in patients with complicated Parkinson disease, *Clin Neuropharmacol*, 2004, 27(3), 124-128.

Verma et al., Osmotically controlled oral drug delivery, *Drug Development and Industrial Pharmacy*, 2000, 26(7), 695-708.

Von Scheele, Levodopa in restless legs, *Lancet*, 1986, 2(8504), 426-427.

Wang et al, Synthesis and pharmacological activities of a novel tripeptide mimetic dopamine prodrug, *Bioorganic & Medicinal Chemistry Letters*, 1995, 5(19), 2195-2198.

Wang et al., Preparation and intestinal absorption of L-Dopa-D-phenylglycine, *J. Food and Drug Analysis*, 2002, 10(2), 81-87.

Wikstrom et al., Manipulating theophylline monohydrate formation during high-shear wet granulation through improved understanding of the role of pharmaceutical excipients, *Pharmaceutical Research* 2008, 25(4), 923-035.

International Search Report and Written Opinion mailed Nov. 3, 2005, for PCT.US2005/019493 filed Jun. 3, 2005.

International Search Report and Written opinion mailed Nov. 3, 2005, for PCT/US2005/019492 filed Jun. 3, 2005.

International Search Report and Written Opinion mailed Jul. 23, 2007, for PCT/US2006/046273 filed Apr. 12, 2006.

International Search Report and Written Opinion mailed Apr. 15, 2008, for PCT/US2007/026200 filed Dec. 20, 2007.

International Search Report and Written Opinion mailed May 14, 2008, for PCT/US2007/026271 filed Dec. 20, 2007.

International Search Report and Written Opinion mailed May 27, 2008, for PCT/US2007/078541 filed Sep. 14, 2007.

International Search Report, Written Opinion, and International Preliminary Report on Patentability mailed May 12, 2011, May 9, 2012, and May 19, 2012, respectively, for PCT/US2010/002937 filed Nov. 8, 2010.

International Search Report, Written Opinion, and International Preliminary Report on Patentability mailed Jul. 30, 2012, Apr. 20, 2011, and Apr. 26, 2011, respectively, for PCT/US2009/005698 filed Oct. 19, 2009.

Office Action mailed Nov. 24, 2006, for U.S. Appl. No. 11/145,159, filed Jun. 3, 2005.

Final Office Action mailed Jun. 15, 2007, for U.S. Appl. No. 11/145,159, filed Jun. 3, 2005.

Notice of Allowance mailed Oct. 10, 2007, for U.S. Appl. No. 11/145,159, filed Jun. 3, 2005.

Notice of Allowance mailed Jan. 23, 2008, for U.S. Appl. No. 11/145,159, filed Jun. 3, 2005 (Supplemental).

(56) References Cited

OTHER PUBLICATIONS

Office Action mailed Mar. 21, 2008, for U.S. Appl. No. 11/634,354, filed Dec. 4, 2006.
Office Action mailed Sep. 16, 2008, for U.S. Appl. No. 11/634,354, filed Dec. 4, 2006.
Notice of Allowance mailed Mar. 20, 2009, for U.S. Appl. No. 11/634,354, filed Dec. 4, 2006.
Notice of Allowance mailed Jun. 22, 2009, for U.S. Appl. No. 11/634,354, filed Dec. 4, 2006.
Office Action mailed Oct. 24, 2008, for U.S. Appl. No. 12/001,618, filed Dec. 11, 2007.
Notice of Allowance mailed May 29, 2009, for U.S. Appl. No. 12/001,618, filed Dec. 11, 2007.
Office Action mailed Jan. 19, 2007, for U.S. Appl. No. 11/145,280, filed Jun. 3, 2005.
Office Action mailed Apr. 17, 2007, for U.S. Appl. No. 11/145,280, filed Jun. 3, 2005.
Notice of Allowance and Examiner's Amendment mailed Sep. 11, 2007, for U.S. Appl. No. 11/145,280, filed Jun. 3, 2005.
Office Action mailed Aug. 7, 2009, for U.S. Appl. No. 12/005,117, filed Dec. 20, 2007.
Notice of Allowance mailed Dec. 16, 2009, for U.S. Appl. No. 12/005,117, filed Dec. 20, 2007.
Office Action mailed Jan. 25, 2010, for U.S. Appl. No. 12/005,120, filed Dec. 20, 2007.
Notice of Allowance mailed Jan. 25, 2010, for U.S. Appl. No. 12/005,120, filed Dec. 20, 2007.
Office Action mailed Jun. 3, 2008, for U.S. Appl. No. 12/008,473, filed Jan. 10, 2008.
Notice of Allowance mailed Oct. 15, 2008, for U.S. Appl. No. 12/008,473, filed Jan. 10, 2008.
Office Action mailed May 4, 2010, for U.S. Appl. No. 12/347,807, filed Dec. 31, 2008.
Office Action mailed Oct. 18, 2010, for U.S. Appl. No. 12/347,807, filed Dec. 31, 2008.
Notice of Allowance mailed Feb. 17, 2011, for U.S. Appl. No. 12/347,807, filed Dec. 31, 2008.
Office Action mailed Dec. 1, 2009, (later vacated) for U.S. Appl. No. 12/364,453, filed Feb. 2, 2009.
Office Action mailed Apr. 1, 2010, for U.S. Appl. No. 12/364,453, filed Feb. 2, 2009.
Office Action mailed Aug. 30, 2010, for U.S. Appl. No. 12/364,453, filed Feb. 2, 2009.
Notice of Allowance mailed Jan. 6, 2011, for U.S. Appl. No. 12/364,453, filed Feb. 2, 2009.
Office Action mailed Apr. 28, 2010, for U.S. Appl. No. 12/489,146, filed Jun. 22, 2009.
Notice of Allowance mailed Oct. 12, 2010, for U.S. Appl. No. 12/489,146, filed Jun. 22, 2009.
Office Action mailed Jun. 11, 2012, for U.S. Appl. No. 12/581,810, filed Oct. 19, 2009.
Office Action mailed Jun. 11, 2012, for U.S. Appl. No. 12/726,978, filed Mar. 18, 2010.
Notice of Allowance and Notice of Allowability mailed Aug. 14, 2012, for U.S. Appl. No. 12/726,978, filed Mar. 18, 2010.
Office Action mailed Apr. 30, 2012, for U.S. Appl. No. 12/904,960, filed Oct. 14, 2010.
Notice of Allowance and Notice of Allowability mailed Jul. 27, 2012, for U.S. Appl. No. 12/904,960, filed Oct. 14, 2010.
Office Action mailed Mar. 27, 2012, for U.S. Appl. No. 12/941,971, filed Nov. 8, 2010.
Office Action mailed May 18, 2012, for U.S. Appl. No. 13/010,419, filed Jan. 20, 2011.
Notice of Allowance mailed Feb. 7, 2012, for U.S. Appl. No. 13/010,419, filed Jan. 20, 2011.
Office Action mailed Sep. 22, 2011, for U.S. Appl. No. 13/095,101, filed Apr. 27, 2011.
Notice of Allowance mailed Dec. 27, 2011, for U.S. Appl. No. 13/095,101, filed Apr. 27, 2011.
Office Action mailed May 18, 2012, for U.S. Appl. No. 13/440,936, filed Apr. 5, 2012.
Office Action mailed Aug. 30, 2012, for U.S. Appl. No. 12/581,808, filed Oct. 19, 2009.
Non-Final Office Action mailed Nov. 23, 2012 for U.S. Appl. No. 13/473,503.
Notice of Allowance mailed Nov. 14, 2012 for U.S. Appl. No. 12/581,810.
Final Office Action mailed Sep. 27, 2012 for U.S. Appl. No. 12/941,971.
Final Office Action mailed Nov. 15, 2012 for U.S. Appl. No. 13/440,936.
Office Action mailed Feb. 20, 2013, for U.S. Appl. No. 12/581,808, filed Oct. 19, 2009.

* cited by examiner

LEVODOPA PRODRUG MESYLATE HYDRATE

This application is a divisional application of U.S. patent application Ser. No. 12/581,810, filed on Oct. 19, 2009, now allowed, which claims the benefit under 35 U.S.C. §119(e) of U.S. Provisional Patent Application Ser. No. 61/106,937, filed on Oct. 20, 2008, each of which is incorporated by reference in its entirety.

Disclosed herein is a crystalline hydrate of a levodopa prodrug mesylate salt, pharmaceutical compositions containing the hydrate, methods of making the hydrate, and the use of the levodopa prodrug mesylate, hydrate for treating diseases or disorders such as Parkinson's disease.

Parkinson's disease is a disabling, progressive illness that affects one in 1,000 people and generally occurs in people over the age of 50 years. Patients with Parkinson's disease have a deficiency of the neurotransmitter dopamine in the brain as a result of nigrostriatal pathway disruption caused by degeneration of the substantia nigra. Levodopa (L-dopa or L-3,4-dihydroxyphenylalanine), an immediate precursor of dopamine, is the most commonly prescribed drug for treatment of this disease.

Following oral administration, levodopa is rapidly absorbed via an amino acid transporter present in the upper small intestine. Due to the narrow distribution of this transporter system, the window available for levodopa absorption is limited and the extent of absorption can depend on the rate at which the drug passes through the upper gastrointestinal tract. Intestinal metabolism of levodopa is the major source of first pass loss of the drug. Approximately 35% of an administered dose of levodopa reaches the systemic circulation as intact levodopa after oral administration in patients (Sasahara, *J. Pharm. Sci* 1990, 69, 261). Once absorbed, levodopa is rapidly metabolized to dopamine by L-aromatic amino acid decarboxylase (AADC) enzymes in the peripheral tissues (e.g., intestines and liver). For this reason, levodopa is normally co-administered with a decarboxylase enzyme inhibitor such as carbidopa or benserazide. When administered with carbidopa, the plasma concentration of intact levodopa increases and thus more levodopa becomes available to be transported into the central nervous system where it is converted to dopamine. Carbidopa and benserazide do not cross the blood-brain barrier to a significant extent and therefore do not inhibit the required conversion of levodopa to dopamine in the brain.

Levodopa prodrugs designed to be absorbed from both the small and large intestines have been described in Xiang et al., U.S. Pat. No. 7,323,585, U.S. Pat. No. 7,342,131, U.S. Patent Application Publication No. 2008/0103200, U.S. Pat. No. 7,534,813, U.S. Patent Application Publication No. 2008/0171789, and U.S. Patent Application Publication No. 2008/0214663, each of which is incorporated by reference in its entirety. These levodopa prodrugs can achieve an oral bioavailability of levodopa that is at least two times greater than the oral bioavailability of levodopa when orally administered on an equivalent molar basis. More specifically, Xiang et al., U.S. Pat. No. 7,342,131 and U.S. Pat. No. 7,534,813 disclose the compound (2R)-2-phenylcarbonyloxypropyl (2S)-2-amino-3-(3,4-dihydroxyphenyl)propanoate hydrochloride in both amorphous and crystalline forms (see Example 8 of Xiang et al.). Crystalline (2R)-2-phenylcarbonyloxypropyl (2S)-2-amino-3-(3,4-dihydroxyphenyl)propanoate mesylate 1:

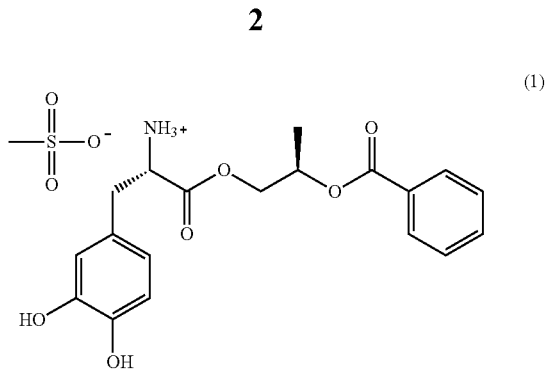

is described by Xiang et al., U.S. Pat. No. 7,563,821. The prodrugs described by Xiang et al. can be efficaciously incorporated into sustained release formulations to provide sustained systemic exposure to levodopa upon oral administration to a patient.

A crystalline hydrate of (2R)-2-phenylcarbonyloxypropyl (2S)-2-amino-3-(3,4-dihydroxyphenyl)propanoate mesylate has been characterized.

In a first aspect, the compound (2R)-2-phenylcarbonyloxypropyl (2S)-2-amino-3-(3,4-dihydroxyphenyl)propanoate mesylate, hydrate is provided.

In a second aspect, crystalline (2R)-2-phenylcarbonyloxypropyl (2S)-2-amino-3-(3,4-dihydroxyphenyl)propanoate mesylate, hydrate is provided.

In a third aspect, pharmaceutical compositions comprising at least one pharmaceutically acceptable vehicle and a therapeutically effective amount of (2R)-2-phenylcarbonyloxypropyl (2S)-2-amino-3-(3,4-dihydroxyphenyl)propanoate mesylate, hydrate or crystalline form thereof are provided.

In a fourth aspect, methods of treating a disease in a patient comprising administering to a patient in need of such treatment a therapeutically effective amount of (2R)-2-phenylcarbonyloxypropyl (2S)-2-amino-3-(3,4-dihydroxyphenyl)propanoate mesylate, hydrate or crystalline form thereof are provided.

In a fifth aspect, methods of synthesizing (2R)-2-phenylcarbonyloxypropyl (2S)-2-amino-3-(3,4-dihydroxyphenyl)propanoate mesylate, hydrate are provided comprising processing (2R)-2-phenylcarbonyloxypropyl (2S)-2-amino-3-(3,4-dihydroxyphenyl)propanoate mesylate by high shear wet granulation using a water content ranging from about 10 wt-% to about 20 wt-% to provide granules comprising (2R)-2-phenylcarbonyloxypropyl (2S)-2-amino-3-(3,4-dihydroxyphenyl)propanoate mesylate, hydrate.

In a sixth aspect, methods of synthesizing (2R)-2-phenylcarbonyloxypropyl (2S)-2-amino-3-(3,4-dihydroxyphenyl)propanoate mesylate, hydrate are provided comprising dissolving (2R)-2-phenylcarbonyloxypropyl (2S)-2-amino-3-(3,4-dihydroxyphenyl)propanoate mesylate in a solvent comprising water to provide a solution; wherein the water activity in the solvent is greater than 0.6 and crystallizing (2R)-2-phenylcarbonyloxypropyl (2S)-2-amino-3-(3,4-dihydroxyphenyl)propanoate mesylate, hydrate.

In a seventh aspect, methods of modulating dopamine levels in a patient are provided comprising administering to the patient a pharmaceutical composition comprising (2R)-2-phenylcarbonyloxypropyl (2S)-2-amino-3-(3,4-dihydroxyphenyl)propanoate mesylate, hydrate and a pharmaceutically acceptable vehicle.

In an eighth aspect, oral dosage forms are provided comprising (2R)-2-phenylcarbonyloxypropyl (2S)-2-amino-3-(3,4-dihydroxyphenyl)propanoate mesylate, hydrate.

These and other features provided by the present disclosure are set forth herein.

The skilled artisan will understand that the drawings, described herein, are for illustration purposes only. The drawings are not intended to limit the scope provided by the present disclosure.

Figure 1:
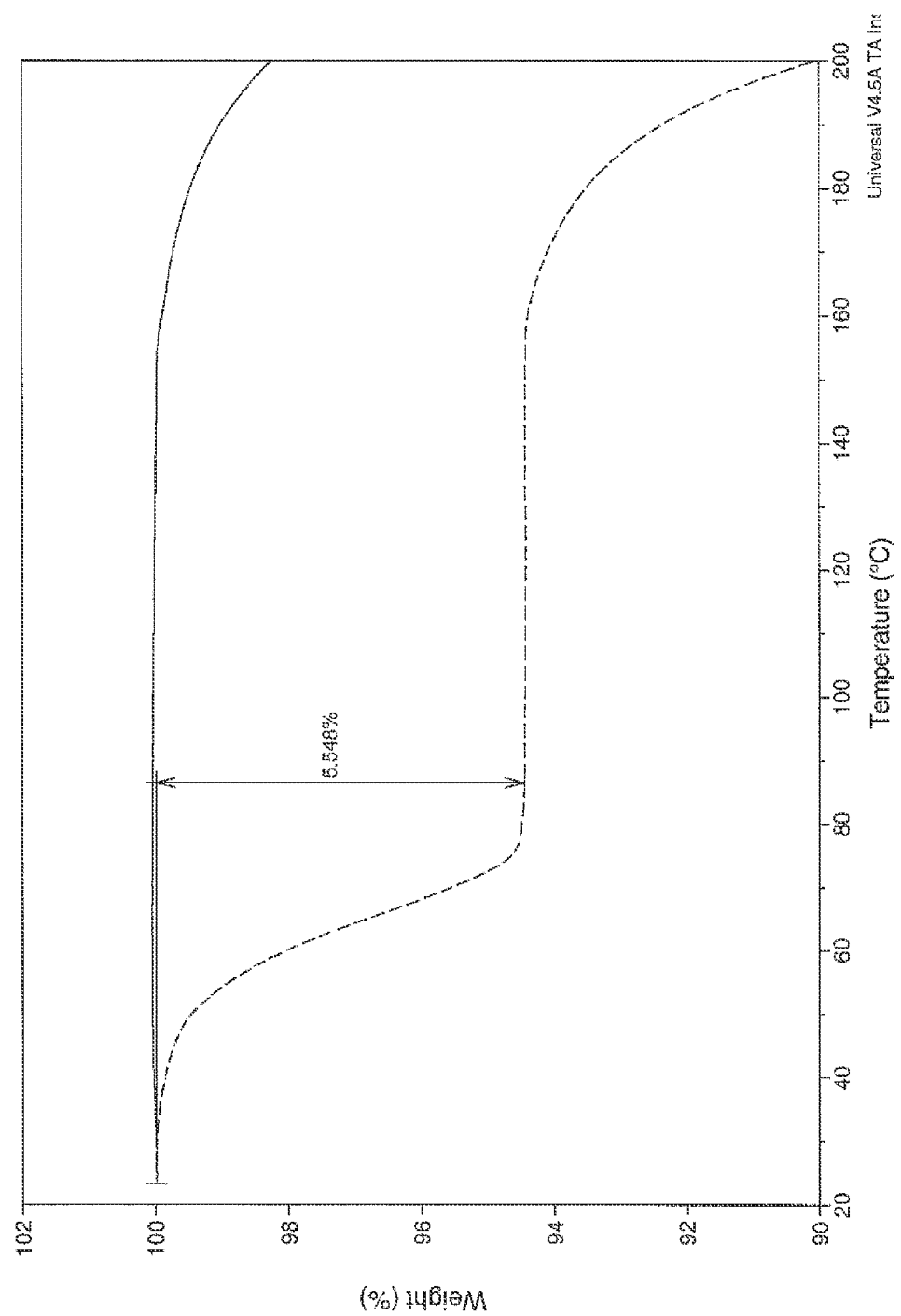
FIG. 1 shows thermogravimetric scans of anhydrous (2R)-2-phenylcarbonyloxypropyl (2S)-2-amino-3-(3,4-dihydroxyphenyl)propanoate mesylate (solid line) and (2R)-2-phenylcarbonyloxypropyl (2S)-2-amino-3-(3,4-dihydroxyphenyl)propanoate mesylate, hydrate (dashed line).

"Bioavailability" refers to the amount of a drug that reaches the systemic circulation of a patient following administration of the drug or prodrug thereof to the patient and may be determined by evaluating, for example, the plasma or blood concentration-versus-time profile for the drug. Parameters useful in characterizing a plasma or blood concentration-versus-time curve include the area under the curve (AUC), the time to maximum concentration ($T_{max}$), and the maximum drug concentration ($C_{max}$), where $C_{max}$ is the maximum concentration of a drug in the plasma or blood of a patient following administration of a dose of the drug or prodrug thereof to the patient, and $T_{max}$ is the time to the maximum concentration ($C_{max}$) of a drug in the plasma or blood of a patient following administration of a dose of the drug or prodrug thereof to the patient.

As used herein, the abbreviation "b.v." or "bv" means "by volume". Particularly, when referencing a mixture of more than one fluid, the term % b.v. means the percentage of one fluid in the total volume. As a non-limiting example a mixture of methanol and water that is 10% b.v. water comprises 10 units of water and 90 units of methanol.

"Crystalline" means having a regularly repeating arrangement of molecules, which is maintained over long range or external face planes.

"Compositional purity" in reference to (2R)-2-phenylcarbonyloxypropyl (2S)-2-amino-3-(3,4-dihydroxyphenyl)propanoate mesylate, hydrate means the percent of (2R)-2-phenylcarbonyloxypropyl (2S)-2-amino-3-(3,4-dihydroxyphenyl)propanoate mesylate, hydrate in a composition relative to the total amount of anhydrous (2R)-2-phenylcarbonyloxypropyl (2S)-2-amino-3-(3,4-dihydroxyphenyl)propanoate mesylate and (2R)-2-phenylcarbonyloxypropyl (2S)-2-amino-3-(3,4-dihydroxyphenyl)propanoate mesylate, hydrate in the composition.

"Disease" refers to a disease, disorder, condition, symptom, or indication.

"Hydrate" means associated with water.

"Hydrate of crystalline (2R)-2-phenylcarbonyloxypropyl (2S)-2-amino-3-(3,4-dihydroxyphenyl)propanoate mesylate" or "crystalline (2R)-2-phenylcarbonyloxypropyl (2S)-2-amino-3-(3,4-dihydroxyphenyl)propanoate mesylate, hydrate" refers to a crystalline compound in which anhydrous (2R)-2-phenylcarbonyloxypropyl (2S)-2-amino-3-(3,4-dihydroxyphenyl)propanoate mesylate is hydrated with one or more water molecules, including fractional water molecules. For example, crystalline (2R)-2-phenylcarbonyloxypropyl (2S)-2-amino-3-(3,4-dihydroxyphenyl)propanoate mesylate hydrate may contain from about 1 to about 2 moles of water, including fractional moles of water, per mole of (2R)-2-phenylcarbonyloxypropyl (2S)-2-amino-3-(3,4-dihydroxyphenyl)propanoate mesylate. In certain embodiments, crystalline (2R)-2-phenylcarbonyloxypropyl (2S)-2-amino-3-(3,4-dihydroxyphenyl)propanoate mesylate, hydrate incorporates from about 1.3 to about 1.7 moles of water, per mole of (2R)-2-phenylcarbonyloxypropyl (2S)-2-amino-3-(3,4-dihydroxyphenyl)propanoate mesylate, and in certain embodiments, about 1.5 moles of water per mole of (2R)-2-phenylcarbonyloxypropyl (2S)-2-amino-3-(3,4-dihydroxyphenyl)

propanoate mesylate (i.e., (2R)-2-phenylcarbonyloxypropyl (2S)-2-amino-3-(3,4-dihydroxyphenyl)propanoate mesylate, sesqui-hydrate).

In certain embodiments, crystalline (2R)-2-phenylcarbonyloxypropyl (2S)-2-amino-3-(3,4-dihydroxyphenyl)propanoate mesylate, hydrate may contain from about 5.1 wt-% to about 5.9 wt-% water, in certain embodiments, from about 5.3 wt-% to about 5.7 wt-% water and in certain embodiments, about 5.5 wt-% water (i.e., (2R)-2-phenylcarbonyloxypropyl (2S)-2-amino-3-(3,4-dihydroxyphenyl)propanoate mesylate, sesqui-hydrate).

"Diastereomeric purity" refers to the percent of one diastereomer of a compound relative to all other diastereomers of the compound in a composition containing more than one diastereomer of the compound. For example, a composition is indicated as having a diastereomeric purity of about 97% of (2R)-2-phenylcarbonyloxypropyl (2S)-2-amino-3-(3,4-dihydroxyphenyl)propanoate mesylate, hydrate when about 97% of the 2-phenylcarbonyloxypropyl-2-amino-3-(3,4-dihydroxyphenyl)propanoate mesylate, hydrate in the composition is the (2R)-2-phenylcarbonyloxypropyl (2S)-2-amino-3-(3,4-dihydroxyphenyl)propanoate mesylate, hydrate diastereomer and about 3% of the 2-phenylcarbonyloxypropyl-2-amino-3-(3,4-dihydroxyphenyl)propanoate mesylate, hydrate in the composition comprises one or more of the other isomers such as the (2R)-(2R)-, the (2S)-(2R)-, and/or the (2S)-(2S)-isomers. In certain embodiments, the diastereomeric purity of a composition is, for example, greater than or at least about 90%, at least about 91%, at least about 92%, at least about 93%, at least about 94%, at least about 95%, at least about 96%, at least about 97%, at least about 98%, or at least about 99% (2R)-2-phenylcarbonyloxypropyl (2S)-2-amino-3-(3,4-dihydroxyphenyl)propanoate mesylate, hydrate.

"Levodopa prodrug mesylate" refers to (2R)-2-phenylcarbonyloxypropyl (2S)-2-amino-3-(3,4-dihydroxyphenyl)propanoate mesylate and crystalline form thereof.

"Levodopa prodrug mesylate, hydrate" refers to (2R)-2-phenylcarbonyloxypropyl (2S)-2-amino-3-(3,4-dihydroxyphenyl)propanoate mesylate, hydrate and crystalline form thereof.

"Parkinson's disease" is a clinical syndrome comprising bradykinesia (slowness and poverty of movement), muscular rigidity, resting tremor (which usually abates during voluntary movement), and an impairment of postural balance leading to disturbance of gait and falling. Other symptoms include gait and posture disturbances such as shuffling, decreased arm swing, turning "en bloc," stooped, forward-reflexed posture, festination, gait freezing and dystonia; speech and swallowing disturbances such as hypophonia, festinating speech, drooling, non-motor causes of speech/language disturbance in both expressive and receptive language, and dysphagia; as well as fatigue, masked facies, micorpgraphia, impaired fine motor dexterity and coordination, impaired gross motor coordination, and poverty of movement. Non-motor mood disturbances associated with Parkinson's disease include mood disturbances such as depression; cognitive disturbances such as slowed reaction time, executive dysfunction, dementia, memory loss, and medication effects; sleep disturbances such as excessive daytime somnolence, insomnia, and disturbances in REM sleep; sensation disturbances such as impair visual perception, dizziness and fainting, impaired proprioception, reduction or loss of sense of smell, and pain; and autonomic disturbances such as oily skin and seborrheic dermatitis, urinary incontinence, constipation and gastric dysmotility, altered sexual function, and weight loss. The Unified Parkinson's disease Rating scale is the primary clinical tool used for the diagnosis of Parkinson's disease.

"Patient" includes animals and mammals, for example humans.

"Pharmaceutical composition" refers to a composition comprising (2R)-2-phenylcarbonyloxypropyl (2S)-2-amino-3-(3,4-dihydroxyphenyl)propanoate mesylate, hydrate or crystalline form thereof and at least one pharmaceutically acceptable vehicle with which (2R)-2-phenylcarbonyloxypropyl (2S)-2-amino-3-(3,4-dihydroxyphenyl)propanoate mesylate, hydrate is administered to a patient. A pharmaceutical composition may further comprise anhydrous (2R)-2-phenylcarbonyloxypropyl (2S)-2-amino-3-(3,4-dihydroxyphenyl)propanoate mesylate or crystalline form thereof.

"Pharmaceutically acceptable" refers to approved or approvable by a regulatory agency of a federal or a state government, listed in the U.S. Pharmacopoeia, or listed in other generally recognized pharmacopoeia for use in mammals, including humans.

"Pharmaceutically acceptable vehicle" refers to a pharmaceutically acceptable diluent, a pharmaceutically acceptable adjuvant, a pharmaceutically acceptable excipient, a pharmaceutically acceptable carrier, or a combination of any of the foregoing with which (2R)-2-phenylcarbonyloxypropyl (2S)-2-amino-3-(3,4-dihydroxyphenyl)propanoate mesylate, hydrate or crystalline form thereof can be administered to a patient and which does not destroy the pharmacological activity thereof and which is nontoxic when administered in doses sufficient to provide a therapeutically effective amount of the compound.

"Prodrug" refers to a derivative of a drug molecule that requires a transformation within the body to release the active drug. Prodrugs are frequently, although not necessarily, pharmacologically inactive until converted to the parent drug. A carboxyl-containing drug may be converted to, for example, an ester of either simple alkyl or acyloxyalkyl prodrug, which may be hydrolyzed in vivo to provide the carboxyl-containing drug. Prodrugs for drugs with functional groups different than those listed above are well known to those skilled in the art. (2R)-2-Phenylcarbonyloxypropyl (2S)-2-amino-3-(3,4-dihydroxyphenyl)propanoate mesylate, hydrate is a prodrug of L-dopa (levodopa).

"Promoiety" refers to a group bonded to a drug, typically to a functional group of the drug, via bond(s) that are cleavable under specified conditions of use. The bond(s) between the drug and promoiety may be cleaved by enzymatic or non-enzymatic means. Under the conditions of use, for example following administration to a patient, the bond(s) between the drug and promoiety may be cleaved to release the parent drug. The cleavage of the promoiety may proceed spontaneously, such as via a hydrolysis reaction, or may be catalyzed or induced by another agent, such as by an enzyme, by light, by acid, or by a change of or exposure to a physical or environmental parameter, such as a change of temperature, pH, etc. The agent may be endogenous to the conditions of use, such as an enzyme present in the systemic circulation to which the prodrug is administered or the acidic conditions of the stomach or the agent may be "Treating" or "treatment" of any disease or disorder refers to arresting or ameliorating a disease, disorder, or at least one of the clinical symptoms of a disease or disorder, reducing the risk of acquiring a disease, disorder, or at least one of the clinical symptoms of a disease or disorder, reducing the development of a disease, disorder or at least one of the clinical symptoms of the disease or disorder, or reducing the risk of developing a disease or disorder or at least one of the clinical symptoms of a disease or disorder. "Treating" or "treatment" also refers to inhibiting the disease or disorder, either physically, (e.g., stabilization of a discernible symptom), physiologically, (e.g., stabilization of a physical parameter), or both, and to inhibiting at least one physical parameter which may or may not be discernible to the patient. In certain embodiments, "treating" or "treatment" refers to delaying the onset of the disease or disorder or at least one or more symptoms thereof in a patient which may be exposed to or predisposed to a disease or disorder even though that patient does not yet experience or display symptoms of the disease or disorder.

"Therapeutically effective amount" refers to the amount of a compound that, when administered to a subject for treating a disease or disorder, or at least one of the clinical symptoms of a disease or disorder, is sufficient to affect such treatment of the disease, disorder, or symptom. A "therapeutically effective amount" can vary depending, for example, on the compound, the disease, disorder, and/or symptoms of the disease or disorder, severity of the disease, disorder, and/or symptoms of the disease or disorder, the age, weight, and/or health of the patient to be treated, and the judgment of the prescribing physician. An appropriate amount in any given instance can be readily ascertained by those skilled in the art or capable of determination by routine experimentation.

Reference is now be made in detail to certain embodiments of compounds, compositions, and methods. The disclosed embodiments are not intended to be limiting of the claims. To the contrary, the claims are intended to cover all alternatives, modifications, and equivalents of the disclosed embodiments.

The levodopa prodrug, (2R)-2-phenylcarbonyloxypropyl (2S)-2-amino-3-(3,4-dihydroxyphenyl)propanoate mesylate 1:

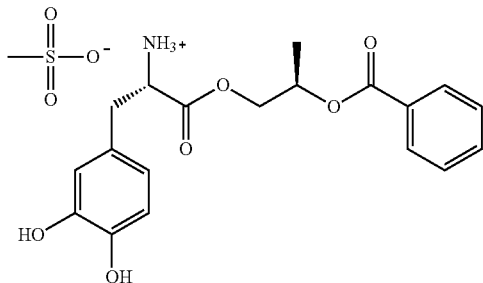

and crystalline form thereof are disclosed by Xiang et al., U.S. Pat. No. 7,563,821. Anhydrous (2R)-2-phenylcarbonyloxypropyl (2S)-2-amino-3-(3,4-dihydroxyphenyl)propanoate mesylate 1 can be prepared via synthetic methods disclosed by Xiang et al., U.S. Pat. No. 7,563,821 and illustrated in Scheme 1.

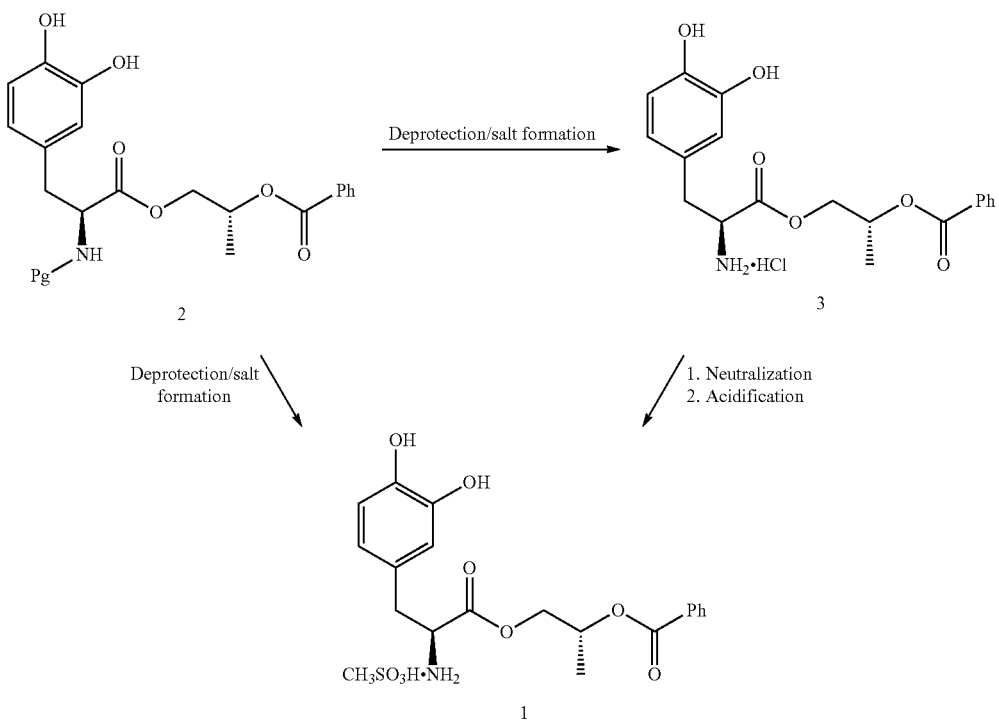

Starting materials useful for preparing these compounds and intermediates thereof are commercially available or can be prepared by well-known synthetic methods. Methods of synthesizing carboxyl ester levodopa prodrugs are also described in Xiang et al., U.S. Pat. No. 7,323,585, U.S. Pat. No. 7,342,131, U.S. Pat. No. 7,534,813, U.S. Patent Application Publication No. 2008/0103200, U.S. Patent Application Publication No. 2008/0171789, and U.S. Patent Application Publication No. 2008/0214663, each of which is incorporated by reference in its entirety. Other methods for synthesizing anhydrous (2R)-2-phenylcarbonyloxypropyl (2S)-2-amino-3-(3,4-dihydroxyphenyl)propanoate mesylate will be readily apparent to one skilled in the art. Accordingly, the method presented in Scheme 1 is illustrative rather than comprehensive.

For example, anhydrous (2R)-2-phenylcarbonyloxypropyl (2S)-2-amino-3-(3,4-dihydroxyphenyl)propanoate mesylate 1 can be prepared from the corresponding appropriately protected (2R)-2-phenylcarboxyloxypropyl (2S)-2-amino-3-(3, 4-dihydroxyphenyl)propanoate precursor 2 via a direct or an indirect route as shown in Scheme 1.

When Pg is Boc (tert-butoxycarbonyl), treatment of precursor 2 with an appropriate acid such as hydrochloric acid in an organic solvent in which precursor 2 is soluble such as, for example, dioxane, dichloromethane, tetrahydrofuran, or mixtures of any of the foregoing at room temperature, followed by solvent removal and crystallization of the resulting residue using an appropriate solvent such as acetonitrile, can provide the hydrochloride salt 3. Other appropriate acids include volatile acids such as trifluoroacetic acid and hydrogen bromide. Conversion of the hydrochloride salt 3 to the corresponding anhydrous mesylate salt 1 can be accomplished by neutralizing the hydrochloride salt with an appropriate base such as sodium bicarbonate ($NaHCO_3$) or potassium bicarbonate ($KHCO_3$) in an appropriate solvent such as water/dichloromethane (DCM), separating DCM from the water, and adding methanesulfonic acid to the DCM solution. The anhydrous mesylate salt 1 can precipitate from the DCM solution.

In certain embodiments, precursor 2 can be directly converted to the anhydrous mesylate salt 1 by treating precursor 2 with an excess of methanesulfonic acid, e.g., about 1.1-100 equivalents, in an organic solvent in which precursor 2 is soluble such as dioxane, dichloromethane, ethylacetate, methyl tert-butyl ether, tetrahydrofuran, or mixtures of any of the foregoing at a temperature from about 20° C. to about 100° C. The anhydrous mesylate salt 1 can then be precipitated out in a non-polar solvent such as methyl tert-butyl ether (MTBE), dichloromethane, or mixtures of the foregoing.

In certain embodiments, precursor 2 can be converted to anhydrous mesylate salt 1 using a one-pot procedure by treating precursor 2 with an excess of hydrogen chloride in dioxane to produce the deprotected hydrochloride salt 3, and then adding methanesulfonic acid to convert the hydrochloride salt 3 to the anhydrous mesylate salt 1.

Anhydrous mesylate salt 1 can be crystallized from a solvent in which the mesylate salt 1 is soluble and in which the solubility of anhydrous mesylate salt 1 is temperature dependent, such as isopropanol, methanol/MTBE, 1% water in isopropanol, 1% water in acetonitrile, or 3% water in ethylacetate, to provide crystalline anhydrous mesylate salt 1. In certain embodiments, the solvent used for crystallizing anhydrous mesylate salt 1 can be selected from acetonitrile, methanol, ethanol, isopropanol, MTBE, dioxane, acetone, ethylacetate, ethylformate, hexane, dichloromethane, and mixtures of any of the foregoing. In certain solvent mixtures comprising two solvents, the ratio of the two solvents can range from about 1:10 to about 10:1. In certain embodiments, the solvent can further comprise less than about 10% water by volume, and in certain embodiments, less than about 5% water by volume. In certain embodiments, the solvent used for crystallizing anhydrous mesylate salt 1 can comprise a mixture of methanol and MTBE in which the ratio (v/v) of methanol to MTBE is from about 1:5 to about 1:7. In certain embodiments, the solvent used for crystallizing anhydrous mesylate salt 1 can comprise from about 1% to about 4% by volume water in isopropanol.

To prepare crystalline anhydrous mesylate salt 1, a solvent in which the solubility of anhydrous mesylate salt 1 is temperature dependent and anhydrous mesylate salt 1, can be heated to provide a solution. In certain embodiments, the solvent can be heated to a temperature up to the reflux temperature, and in certain embodiments, up to a temperature less than about 75° C. In certain embodiments, the concentration of anhydrous mesylate salt 1 in the solution is less than about 500 mg/mL and in certain embodiments ranges from about 50 mg/mL to about 200 mg/mL. The temperature of the solution can then be changed to decrease the solubility of anhydrous mesylate salt 1 in the solvent. For example, the temperature of the solution can be decreased to room temperature (e.g., about 25° C.), and in certain embodiments to about 0° C. The time to cool the solution can be selected to optimize the yield, compositional purity, and/or optical purity of crystalline anhydrous mesylate salt 1. In some embodiments, the solution can be cooled to a first temperature and crystalline anhydrous mesylate salt 1 isolated, and the solution cooled further in a second crystallization and additional crystalline anhydrous mesylate salt 1 isolated. Crystalline anhydrous mesylate salt 1 can be isolated from the solvent by filtration. The filter cake can be washed in an appropriate solvent, such as, for example, a low boiling point solvent that minimizes the amount of residue remaining in crystalline anhydrous mesylate salt 1. Examples of appropriate wash solvents include acetonitrile, methanol, ethanol, isopropanol, MTBE, dioxane, acetone, ethylacetate, ethylformate, hexane, dichloromethane, and mixtures of any of the foregoing. One skilled in the art can appreciate that other methods can be used to crystallize anhydrous mesylate salt 1, including, for example, methods comprising stirring and/or seeding.

In certain embodiments, crystalline anhydrous mesylate salt 1 obtained via any of the methods disclosed herein is characterized by an X-ray powder diffraction having characteristic scattering angles measured using Cu—$K_\alpha$ radiation (°2θ) at least at 4.7°±0.2°, 5.0°±0.2°, 8.5°±0.2°, 9.6°±0.2°, 13.6°±0.2°, 15.0°±0.2°, 17.0°±0.2°, 17.4°±0.2°, 17.7°±0.2°, 19.1°±0.2°, 19.5°±0.2°, 20.0°±0.2°, 20.4±0.2°, 21.1°±0.2°, 22.3°±0.2°, 22.9°±0.2°, 23.1°±0.2°, 23.3°±0.2°, 24.3°±0.2°, 25.0°±0.2°, 25.3°±0.2°, 25.7°±0.2°, 25.8°±0.2°, 26.9°±0.2°, 27.3°±0.2°, 28.2°±0.2°, 30.1°±0.2°, 30.5°±0.2°, 32.0°±0.2°, 33.8°±0.2°, 34.3°±0.2°, 37.6°±0.2°, and 38.4°±0.2°. In certain embodiments, crystalline anhydrous mesylate salt 1 obtained via any of the methods disclosed herein is characterized by an X-ray powder diffraction pattern having characteristic scattering angles measured using Cu—$K_\alpha$ radiation (°2θ) at least at 5.0°±0.2°, 8.5°±0.2°, 13.6°±0.2°, 15.0°±0.2°, 17.0°±0.2°, 17.7°±0.2°, 20.4°±0.2°, 21.1°±0.2°, 25.0°±0.2°, 25.8°±0.2°, 28.2°±0.2°, 30.1°±0.2°, and 37.6°±0.2°.

In certain embodiments, crystalline anhydrous levodopa mesylate is characterized by an X-ray powder diffraction pattern having characteristic scattering angles measured using Cu—$K_\alpha$ radiation (°2θ) at least at 5.0°±0.2°, 8.6°±0.2°, 9.6°±0.2°, 13.6°±0.2° 17.1°±0.2°, 20.4°±0.2°, 25.7°±0.2°, and 28.3°±0.2°. In certain embodiments, crystalline anhydrous levodopa mesylate is characterized by an X-ray powder diffraction pattern having characteristic scattering angles measured using Cu—$K_\alpha$ radiation (°2θ) at least at 5.0°±0.2°, 8.6°±0.2°, 9.6°±0.2°, 13.6°±0.2°, 17.1°±0.2°, 17.5°±0.2°, 17.7°±0.2°, 19.2°±0.2°, 19.5°±0.2°, 20.4°±0.2°, 21.2°±0.2°, 25.1°±0.2°, 25.7°±0.2°, 26.0°±0.2°, 28.3°±0.2°, 33.9°±0.2°, 37.7°±0.2°, and 38.4°±0.2°. In certain embodiments, crystalline anhydrous levodopa mesylate is characterized by an X-ray powder diffraction pattern having characteristic scattering angles measured using Cu—$K_\alpha$ radiation (°2θ) at least at 5.0°±0.2°, 8.6°±0.2°, 9.6°±0.2°, 10.2°±0.2°, 13.6°±0.2°, 15.0°±0.2°, 17.1°±0.2°, 17.5°±0.2°, 17.7°±0.2°, 19.2°±0.2°, 19.5°±0.2°, 20.4°±0.2°, 21.2°±0.2°, 25.1°±0.2°, 25.3°±0.2°, 25.7°±0.2°, 26.0°±0.2°, 26.9°±0.2°, 27.3°±0.2°, 28.3°±0.2°, 30.5°±0.2°, 33.9°±0.2°, 34.3°±0.2°, 35.2°±0.2°, 37.7°±0.2°, and 38.4°±0.2°.

In certain embodiments, formation and crystallization of anhydrous mesylate salt 1 can be performed in a one-pot procedure at about room temperature, e.g., 25° C. For example, after deprotection and neutralization, (2R)-2-phenylcarbonyloxypropyl (2S)-2-amino-3-(3,4-dihydroxyphenyl)propanoate can be dissolved in a solvent such as ethylacetate, isopropanol/dichloromethane, or isopropanol/ethylacetate and treated with about 0.9-1.2 equivalents of methanesulfonic acid at about room temperature. Anhydrous mesylate salt 1 can crystallize from the solution with or without stirring or seeding.

As an example of a one-pot procedure for preparing crystalline anhydrous (2R)-2-phenylcarbonyloxypropyl (2S)-2-amino-3-(3,4-dihydroxyphenyl)propanoate mesylate, a solution of (2R)-2-phenylcarbonyloxypropyl (2S)-2-(tert-butoxycarbonyl)amino-3-(3,4-dihydroxyphenyl)propanoate in a first solvent in which it is soluble is prepared. Examples of suitable solvents include dichloromethane and dioxane. The tert-butoxycarbonyl group is deprotected by adding an acid to provide (2R)-2-phenylcarbonyloxypropyl (2S)-2-amino-3-(3,4-dihydroxyphenyl)propanoate acid salt. Suitable acids are not limited to volatile acids. Examples of suitable acids for deprotecting the tert-butoxycarbonyl group include hydrochloric acid, methanesulfonic acid, trifluoroacetic acid, and hydrogen bromide. After deprotection, the first solvent can be removed and water added to the (2R)-2-phenylcarbonyloxypropyl (2S)-2-amino-3-(3,4-dihydroxyphenyl)propanoate acid salt. The (2R)-2-phenylcarbonyloxypropyl (2S)-2-amino-3-(3,4-dihydroxyphenyl)propanoate acid salt can be neutralized with a base such as NaHCO$_3$ or KHCO$_3$ to provide (2R)-2-phenylcarbonyloxypropyl (2S)-2-amino-3-(3,4-dihydroxyphenyl)propanoate. (2R)-2-Phenylcarbonyloxypropyl (2S)-2-amino-3-(3,4-dihydroxyphenyl)propanoate can then be extracted with a second solvent such as methyl tert-butylether, dichloromethane, ethylacetate, or a mixture of ethylacetate and isopropanol. Methanesulfonic acid can be added to the extracted (2R)-2-phenylcarbonyloxypropyl (2S)-2-amino-3-(3,4-dihydroxyphenyl)propanoate to convert the (2R)-2-phenylcarbonyloxypropyl (2S)-2-amino-3-(3,4-dihydroxyphenyl)propanoate to crystalline anhydrous (2R)-2-phenylcarbonyloxypropyl (2S)-2-amino-3-(3,4-dihydroxyphenyl)propanoate mesylate. Crystalline anhydrous (2R)-2-phenylcarbonyloxypropyl (2S)-2-amino-3-(3,4-dihydroxyphenyl)propanoate mesylate can then be isolated from the second solvent by filtration.

One skilled in the art will appreciate that the methods provided by the present disclosure can be used to prepare anhydrous (2R)-2-phenylcarbonyloxypropyl (2S)-2-amino-3-(3,4-dihydroxyphenyl)propanoate mesylate 1 or crystalline form thereof having high compositional and diastereomeric purity. For example, in certain embodiments, the compositional purity of anhydrous levodopa mesylate salt 1 can be at least about 95%, in certain embodiments, at least about 97%, in certain embodiments, at least about 98%, and in certain embodiments, can be at least about 99%, and in certain embodiments, the diastereomeric purity can be at least about 95%, in certain embodiments, at least about 97%, in certain embodiments, at least about 98%, and in certain embodiments, at least about 99%.

Crystalline (2R)-2-phenylcarbonyloxypropyl (2S)-2-amino-3-(3,4-dihydroxyphenyl)propanoate mesylate, hydrate is formed from crystalline anhydrous (2R)-2-phenylcarbonyloxypropyl (2S)-2-amino-3-(3,4-dihydroxyphenyl)propanoate mesylate as a result of thermodynamic and kinetic equilibria of the two crystal forms with water in the environment.

Crystalline (2R)-2-phenylcarbonyloxypropyl (2S)-2-amino-3-(3,4-dihydroxyphenyl)propanoate mesylate, hydrate may be formed from a solvent containing anhydrous (2R)-2-phenylcarbonyloxypropyl (2S)-2-amino-3-(3,4-dihydroxyphenyl)propanoate mesylate and having a water activity greater than about 0.6, and in certain embodiments, greater than about 0.7, wherein the water activity is determined at room temperature (about 25° C.). In certain embodiments, the solvent may be a mixture of an alcohol and water, and in certain embodiments, a mixture of isopropanol and water. In certain embodiments, the solvent comprises isopropanol and at least about 7%-bv water. At room temperature (about 25° C.) a mixture of isopropanol and about 7 vol-% to about 10 vol-% water has a water activity ranging from about 0.6 to about 0.7. Crystalline (2R)-2-phenylcarbonyloxypropyl (2S)-2-amino-3-(3,4-dihydroxyphenyl)propanoate mesylate, hydrate may be prepared from other solvents containing (2R)-2-phenylcarbonyloxypropyl (2S)-2-amino-3-(3,4-dihydroxyphenyl)propanoate mesylate and at a temperature of about 25° C. providing the water activity of the mixture is greater than about 0.6 or greater than about 0.7. At higher temperatures, the critical water activity will be higher.

Figure 5:
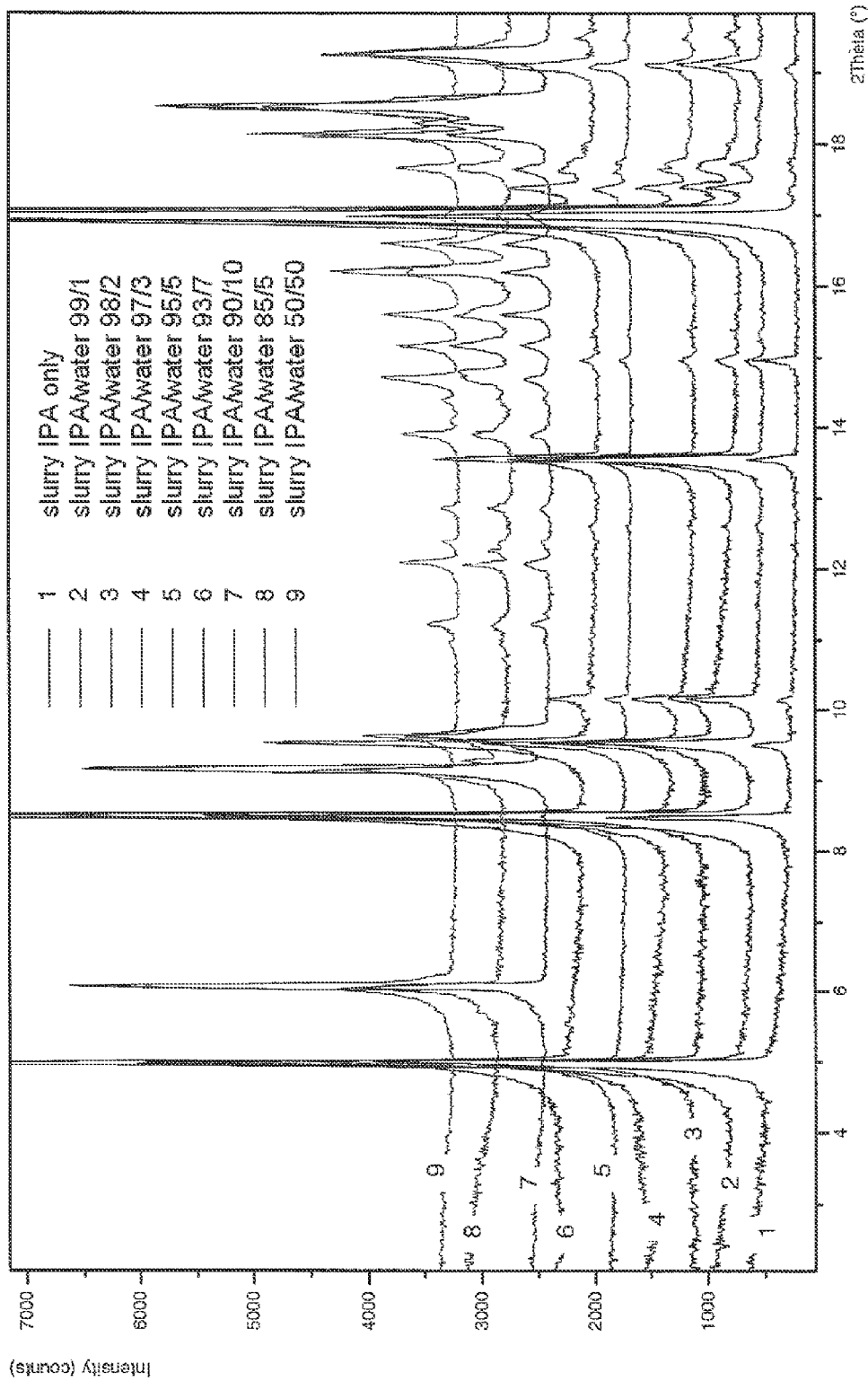
FIG. 5 shows X-ray powder diffraction patterns of anhydrous (2R)-2-phenylcarbonyloxypropyl (2S)-2-amino-3-(3,4-dihydroxyphenyl)propanoate mesylate (patterns 1-6) or (2R)-2-phenylcarbonyloxypropyl (2S)-2-amino-3-(3,4-dihydroxyphenyl)propanoate mesylate, hydrate (patterns 7-9) crystallized from isopropanol/water mixtures containing different amounts of water.

X-ray powder diffraction patterns of crystalline (2R)-2-phenylcarbonyloxypropyl (2S)-2-amino-3-(3,4-dihydroxyphenyl)propanoate mesylate prepared from isopropanol solutions at about 25° C. having different water content are shown in FIG. 5. Above a water content greater than about 10 vol-%, crystalline (2R)-2-phenylcarbonyloxypropyl (2S)-2-amino-3-(3,4-dihydroxyphenyl)propanoate mesylate, hydrate crystallizes from the solution, whereas at lower water content, crystalline anhydrous (2R)-2-phenylcarbonyloxypropyl (2S)-2-amino-3-(3,4-dihydroxyphenyl)propanoate mesylate is formed.

Crystalline (2R)-2-phenylcarbonyloxypropyl (2S)-2-amino-3-(3,4-dihydroxyphenyl)propanoate mesylate, hydrate may also be produced during high shear wet granulation processing of crystalline anhydrous (2R)-2-phenylcarbonyloxypropyl (2S)-2-amino-3-(3,4-dihydroxyphenyl)propanoate mesylate. For example, crystalline (2R)-2-phenylcarbonyloxypropyl (2S)-2-amino-3-(3,4-dihydroxyphenyl)propanoate mesylate, hydrate can be formed during high shear wet granulation processing of a mixture containing crystalline anhydrous (2R)-2-phenylcarbonyloxypropyl (2S)-2-amino-3-(3,4-dihydroxyphenyl)propanoate mesylate and an amount of vehicle using a water content greater than about 10 wt-%, greater than about 12 wt-%, and in certain embodiments, greater than about 15 wt-%. In certain embodiments, the amount of water used during high shear wet granulation processing can range from about 10 wt-% to about 20 wt-%, and in certain embodiments, about 15 wt-%. In certain embodiments, the water content can be greater than about 20 wt-%.

Figure 4:
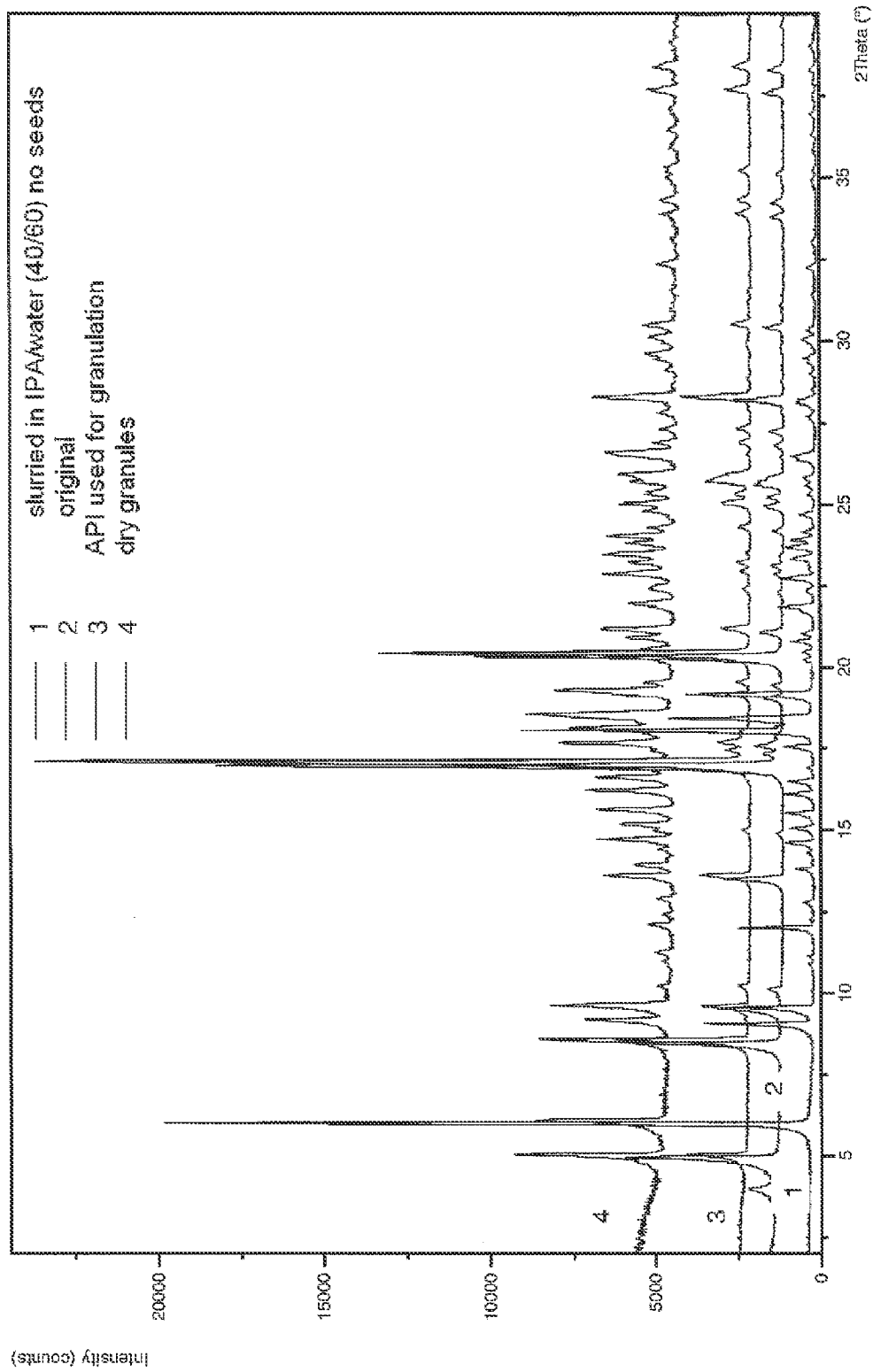
FIG. 4 shows X-ray powder diffraction patterns of anhydrous (2R)-2-phenylcarbonyloxypropyl (2S)-2-amino-3-(3,4-dihydroxyphenyl)propanoate mesylate (patterns 2 and 3), (2R)-2-phenylcarbonyloxypropyl (2S)-2-amino-3-(3,4-dihydroxyphenyl)propanoate mesylate, hydrate prepared by crystallization from isopropanol/water (40/60) (pattern 1), and for dry granules prepared by high shear wet granulation (pattern 4).

The amount of vehicle used to form granules comprising (2R)-2-phenylcarbonyloxypropyl (2S)-2-amino-3-(3,4-dihydroxyphenyl)propanoate mesylate, hydrate can be less than about 10 wt-%, less than about 5 wt-%, and in certain embodiments, less than about 1 wt-%. X-ray powder diffraction patterns of granules comprising a mixture of anhydrous (2R)-2-phenylcarbonyloxypropyl (2S)-2-amino-3-(3,4-dihydroxyphenyl)propanoate mesylate and (2R)-2-phenylcarbonyloxypropyl (2S)-2-amino-3-(3,4-dihydroxyphenyl)propanoate mesylate, hydrate prepared by high shear wet granulation using a water content of about 15 wt-% are shown in FIG. 4.

Crystalline anhydrous (2R)-2-phenylcarbonyloxypropyl (2S)-2-amino-3-(3,4-dihydroxyphenyl)propanoate mesylate can also convert to crystalline (2R)-2-phenylcarbonyloxypropyl (2S)-2-amino-3-(3,4-dihydroxyphenyl)propanoate mesylate, hydrate in the presence of water vapor. For example, crystalline anhydrous (2R)-2-phenylcarbonyloxypropyl (2S)-2-amino-3-(3,4-dihydroxyphenyl)propanoate mesylate converts to the hydrate within 24 hours at a temperature of about 25° C. and a humidity of at least about 60% RH.

One skilled in the art will appreciate that although (2R)-2-phenylcarbonyloxypropyl (2S)-2-amino-3-(3,4-dihydroxyphenyl)propanoate mesylate, hydrate is disclosed, a sample of (2R)-2-phenylcarbonyloxypropyl (2S)-2-amino-3-(3,4-dihydroxyphenyl)propanoate mesylate, hydrate can have various compositional and diastereomeric purities. In certain embodiments, (2R)-2-phenylcarbonyloxypropyl (2S)-2-amino-3-(3,4-dihydroxyphenyl)propanoate mesylate, hydrate or crystalline form thereof can exhibit a compositional purity of at least about 90%, at least about 91%, at least about 92%, at least about 93%, at least about 94%, at least about 95%, at least about 96%, at least about 97%, at least about 98%, at least about 99%, and in certain embodiments, in excess of at least about 99%. In certain embodiments, (2R)-2-phenylcarbonyloxypropyl (2S)-2-amino-3-(3,4-dihydroxyphenyl)propanoate mesylate, hydrate or crystalline form thereof can exhibit a diastereomeric purity of at least about 90%, at least about 91%, at least about 92%, at least about 93%, at least about 94%, at least about 95%, at least about 96%, at least about 97%, at least about 98%, at least about 99%, and in certain embodiments, in excess of at least about 99%.

Furthermore, crystalline (2R)-2-phenylcarbonyloxypropyl (2S)-2-amino-3-(3,4-dihydroxyphenyl)propanoate mesylate may comprise a combination of anhydrous and hydrated forms.

In certain embodiments, (2R)-2-phenylcarbonyloxypropyl (2S)-2-amino-3-(3,4-dihydroxyphenyl)propanoate mesylate, hydrate is a crystalline form. In certain embodiments, crystalline (2R)-2-phenylcarbonyloxypropyl (2S)-2-amino-3-(3,4-dihydroxyphenyl)propanoate mesylate, hydrate exhibits an X-ray powder diffraction pattern substantially as shown in any one of FIGS. 4, 5, 7, and 8.

In certain embodiments, crystalline levodopa mesylate, hydrate is characterized by an X-ray powder diffraction pattern having characteristic scattering angles measured using Cu—K$_\alpha$ radiation (°2θ) at least at 6.0°±0.2°, 9.1°±0.2°, 9.6°±0.2°, 12.0°±0.2°, 13.8°±0.2°, 14.6°±0.2°, 15.1°±0.2°, 15.6°±0.2°, 16.1°±0.2°, 16.6°±0.2°, 17.6°±0.2°, 18.5°±0.2°, and 19.2°±0.2°.

In certain embodiments, crystalline levodopa mesylate, hydrate is characterized by an X-ray powder diffraction pattern having characteristic scattering angles measured using Cu—K$_\alpha$ radiation (°2θ) at least at 6.0°±0.2°, 9.1°±0.2°, 9.6°±0.2°, 12.0°±0.2°, 13.8°±0.2°, 14.6°±0.2°, 15.1°±0.2°, 15.6°±0.2°, 16.1°±0.2°, 16.6°±0.2°, 17.6°±0.2°, 18.5°±0.2°, 19.2°±0.2°, 20.8°±0.2°, 21.9°±0.2°, 22.8°±0.2°, 23.4°±0.2°, 23.7°±0.2°, 23.9°±0.2°, and 26.5°±0.2°.

In certain embodiments, crystalline levodopa mesylate, hydrate is characterized by an X-ray powder diffraction pattern having characteristic scattering angles measured using Cu—K$_\alpha$ radiation (°2θ) at least at 6.0°±0.2°, 9.1°±0.2°, 9.6°±0.2°, 11.2°±0.2°, 12.0°±0.2°, 12.8°±0.2°, 13.8°±0.2°, 14.3°±0.2°, 14.6°±0.2°, 15.1°±0.2°, 15.6°±0.2°, 16.1°±0.2°, 16.6°±0.2°, 17.6°±0.2°, 18.5°±0.2°, 18.7°±0.2°, 19.2°±0.2°, 20.5°±0.2°, 20.8°±0.2°, 21.1°±0.2°, 21.9°±0.2°, 22.8°±0.2°, 23.4°±0.2°, 23.7°±0.2°, 23.9°±0.2°, 24.7°±0.2°, 26.5°±0.2°, 28.2°±28.3°±0.2°, and 29.5°±0.2°.

One skilled in the art will recognize that slight variations in the observed °2θ diffraction angles can be expected based on, for example, the specific diffractometer employed, the analyst, and the sample preparation technique. Greater variation can be expected for the relative peak intensities. Comparison of diffraction patterns can be based primarily on observed °2θ diffraction angles with lesser importance attributed to relative peak intensities.

Figure 2:
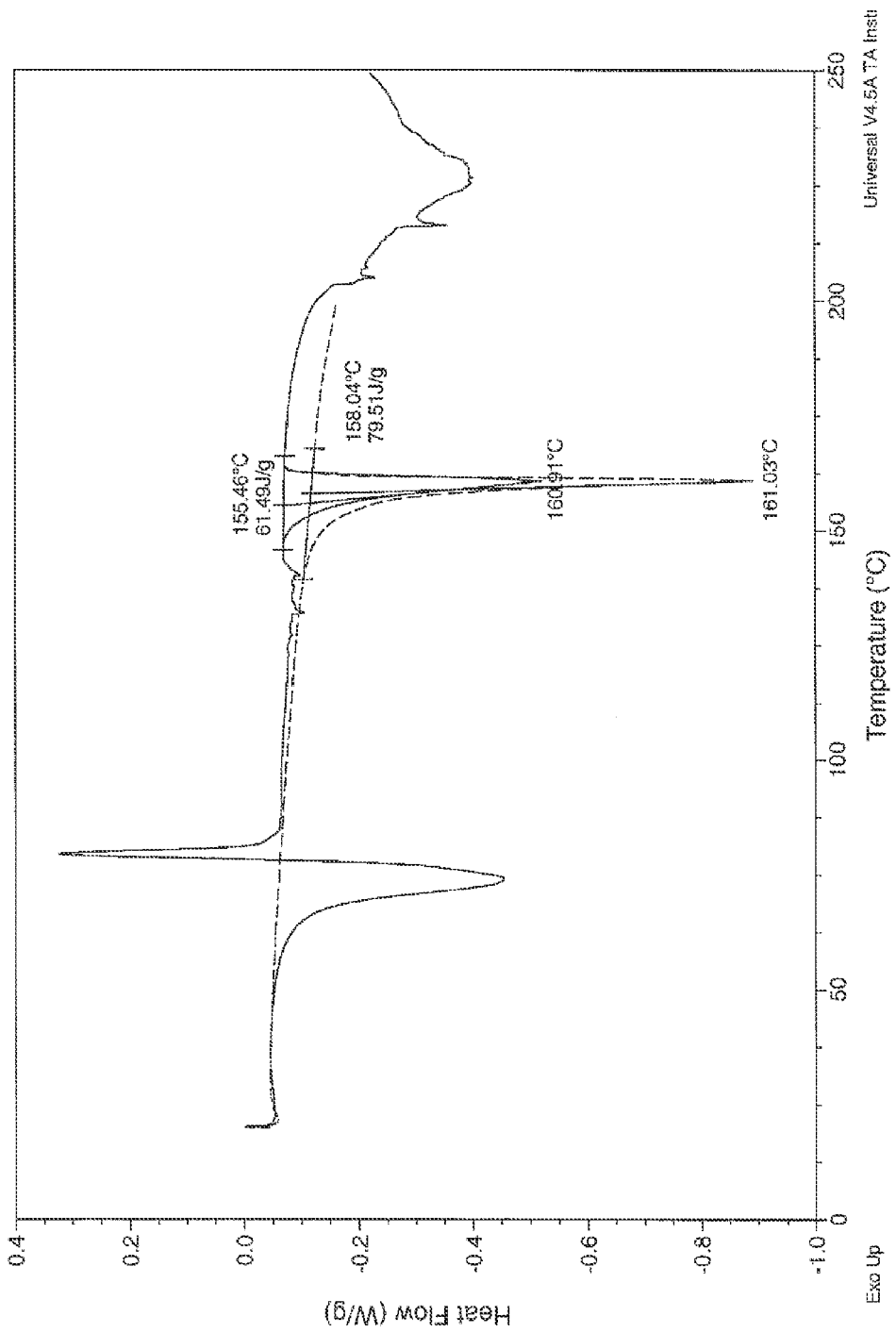
FIG. 2 shows differential scanning calorimetry scans of anhydrous (2R)-2-phenylcarbonyloxypropyl (2S)-2-amino-3-(3,4-dihydroxyphenyl)propanoate mesylate (dashed line) and (2R)-2-phenylcarbonyloxypropyl (2S)-2-amino-3-(3,4-dihydroxyphenyl)propanoate mesylate, hydrate (solid line).

In certain embodiments, crystalline (2R)-2-phenylcarbonyloxypropyl (2S)-2-amino-3-(3,4-dihydroxyphenyl)propanoate mesylate, hydrate is characterized by a differential scanning calorimetry (DSC) thermogram having an endotherm at about 75° C. representing dehydration followed by an exotherm at about 80° C. representing recrystallization to the anhydrous form. The anhydrous form then exhibits an endotherm at about 161° C. An example of a DSC thermogram of crystalline (2R)-2-phenylcarbonyloxypropyl (2S)-2-amino-3-(3,4-dihydroxyphenyl)propanoate mesylate, hydrate is shown in FIG. 2.

In certain embodiments, crystalline (2R)-2-phenylcarbonyloxypropyl (2S)-2-amino-3-(3,4-dihydroxyphenyl)propanoate mesylate, hydrate comprises from about 1.2 moles water to about 1.8 moles water, from about 1.4 moles water to about 1.6 moles water, and in certain embodiments, about 1.5 moles water per mole of (2R)-2-phenylcarbonyloxypropyl (2S)-2-amino-3-(3,4-dihydroxyphenyl)propanoate mesylate.

In certain embodiments, crystalline (2R)-2-phenylcarbonyloxypropyl (2S)-2-amino-3-(3,4-dihydroxyphenyl)propanoate mesylate, hydrate comprises from about 5.1 wt-% water to about 5.9 wt-% water, from about 5.4 wt-% water to about 5.6 wt-% water, and in certain embodiments, about 5.5 wt-% water.

In certain embodiments, crystalline (2R)-2-phenylcarbonyloxypropyl (2S)-2-amino-3-(3,4-dihydroxyphenyl)propanoate mesylate, hydrate is stable, e.g., does not absorb moisture and/or convert to another polymorphic form under typical pharmaceutical processing and/or storage conditions.

The physical properties and characteristics of crystalline (2R)-2-phenylcarbonyloxypropyl (2S)-2-amino-3-(3,4-dihydroxyphenyl)propanoate mesylate, hydrate prepared by methods provided by the present disclosure are consistent with that of a single polymorph.

Pharmaceutical compositions provided by the present disclosure may comprise a therapeutically effective amount of (2R)-2-phenylcarbonyloxypropyl (2S)-2-amino-3-(3,4-dihydroxyphenyl)propanoate mesylate, hydrate, and in certain embodiments, in purified form, together with a suitable amount of one or more pharmaceutically acceptable vehicles, so as to provide a composition for proper administration to a patient. Other examples of suitable pharmaceutical vehicles are described in the art.

Pharmaceutical compositions comprising (2R)-2-phenylcarbonyloxypropyl (2S)-2-amino-3-(3,4-dihydroxyphenyl) propanoate mesylate, hydrate may be manufactured by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable vehicles, which facilitate processing of levodopa prodrug mesylate or crystalline form thereof and one or more pharmaceutically acceptable vehicles into formulations that can be used pharmaceutically. Proper formulation is dependent upon the route of administration chosen. Pharmaceutical compositions provided by the present disclosure may take the form of solutions, suspensions, emulsion, tablets, pills, pellets, capsules, capsules containing liquids, powders, sustained-release formulations, suppositories, emulsions, aerosols, sprays, suspensions, or any other form suitable for use.

In certain embodiments, (2R)-2-phenylcarbonyloxypropyl (2S)-2-amino-3-(3,4-dihydroxyphenyl)propanoate mesylate, hydrate may be incorporated into pharmaceutical compositions to be administered orally. Oral administration of such pharmaceutical compositions may result in uptake of the (2R)-2-phenylcarbonyloxypropyl (2S)-2-amino-3-(3,4-dihydroxyphenyl)propanoate mesylate, hydrate throughout the intestine and entry into the systemic circulation. Such compositions may be prepared in a manner known in the pharmaceutical art and comprise (2R)-2-phenylcarbonyloxypropyl (2S)-2-amino-3-(3,4-dihydroxyphenyl)propanoate mesylate, hydrate and at least one pharmaceutically acceptable vehicle. Pharmaceutical compositions may include a therapeutically effective amount of (2R)-2-phenylcarbonyloxypropyl (2S)-2-amino-3-(3,4-dihydroxyphenyl)propanoate mesylate, hydrate, in some embodiments, in purified form, together with a decarboxylase inhibitor such as carbidopa or benserazide, and/or a COMT inhibitor such as entacapone and tolecapone, and a suitable amount of a pharmaceutically acceptable vehicle.

(2R)-2-Phenylcarbonyloxypropyl (2S)-2-amino-3-(3,4-dihydroxyphenyl)propanoate mesylate, hydrate may be administered to a patient in a therapeutically effective amount. It will be understood, however, that the amount of (2R)-2-phenylcarbonyloxypropyl (2S)-2-amino-3-(3,4-dihydroxyphenyl)propanoate mesylate, hydrate actually administered will be determined by a physician, in the light of the relevant circumstances, including the condition to be treated, the chosen route of administration, the actual compound administered, the age, weight, and response of the individual patient, the disease being treated, the severity of the patient's symptoms, and the like.

(2R)-2-Phenylcarbonyloxypropyl (2S)-2-amino-3-(3,4-dihydroxyphenyl)propanoate mesylate, hydrate may be used with a number of different dosage forms, which can be adapted to provide sustained release of (2R)-2-phenylcarbonyloxypropyl (2S)-2-amino-3-(3,4-dihydroxyphenyl)propanoate mesylate, hydrate upon oral administration. Sustained release refers to release of a therapeutic or preventive amount of a drug or an active metabolite thereof over a period of time that is longer than that of a conventional formulation of the drug. For oral formulations, sustained release typically means release of the drug within the gastrointestinal tract lumen over a time period ranging, for example, from about 2 to about 30 hours, and in certain embodiments, over a time period ranging from about 4 to about 24 hours. Sustained release formulations achieve therapeutically effective concentrations of the drug in the systemic circulation over a prolonged period of time relative to that achieved by oral administration of a conventional formulation of the drug. Sustained release oral dosage forms are known in the art.

Regardless of the specific form of sustained release oral dosage form used, (2R)-2-phenylcarbonyloxypropyl (2S)-2-amino-3-(3,4-dihydroxyphenyl)propanoate mesylate, hydrate may be released from a dosage form such as an orally administered dosage form, over a sufficient period of time to provide prolonged therapeutic concentrations of levodopa in the blood of a patient enabling administration of the dosage form on only a once or twice per day basis. Following oral administration, dosage forms comprising (2R)-2-phenylcarbonyloxypropyl (2S)-2-amino-3-(3,4-dihydroxyphenyl)propanoate mesylate, hydrate can provide a therapeutic or prophylactic concentration of levodopa in the plasma and/or blood of a patient for a time period of at least about 4 hours, in certain embodiments, for at least about 8 hours, for at least about 12 hours, for at least about 16 hours, for at least about 20 hours, and in certain embodiments, for at least about 24 hours following oral administration of the dosage form to the patient. A therapeutically or prophylactically effective concentration of levodopa in the blood and/or plasma of a patient can depend on a number of factors including, for example, the disease being treated, the severity of the disease, the weight of the patient, and the health of the patient.

In certain embodiments, (2R)-2-phenylcarbonyloxypropyl (2S)-2-amino-3-(3,4-dihydroxyphenyl)propanoate mesylate, hydrate or pharmaceutical compositions thereof may be administered twice per day, in certain embodiments, once per day, and in certain embodiments at intervals greater than once per day.

In certain embodiments, an oral dosage form comprises (2R)-2-phenylcarbonyloxypropyl (2S)-2-amino-3-(3,4-dihydroxyphenyl)propanoate mesylate, hydrate; and in certain embodiments, a combination of (2R)-2-phenylcarbonyloxypropyl (2S)-2-amino-3-(3,4-dihydroxyphenyl)propanoate mesylate, hydrate and anhydrous (2R)-2-phenylcarbonyloxypropyl (2S)-2-amino-3-(3,4-dihydroxyphenyl)propanoate mesylate. In certain embodiments, the amount of (2R)-2-phenylcarbonyloxypropyl (2S)-2-amino-3-(3,4-dihydroxyphenyl)propanoate mesylate, hydrate in the oral dosage form is at least about 75 wt-%, at least about 80 wt-%, at least about 85 wt-%, and in certain embodiments, at least about 90 wt-%. In certain embodiments, the combined amount of (2R)-2-phenylcarbonyloxypropyl (2S)-2-amino-3-(3,4-dihydroxyphenyl)propanoate mesylate, hydrate and anhydrous (2R)-2-phenylcarbonyloxypropyl (2S)-2-amino-3-(3,4-dihydroxyphenyl)propanoate mesylate in the oral dosage form is at least about 75 wt-%, at least about 80 wt-%, at least about 85 wt-%, and in certain embodiments, at least about 90 wt-%.

Pharmaceutical compositions provided by the present disclosure may be administered for therapeutic or prophylactic treatments. A therapeutic amount is an amount sufficient to treat a disease or symptom of a disease, or otherwise prevent, hinder, retard, or reverse the progression of disease or undesirable symptom of a disease. In prophylactic applications, pharmaceutical compositions provided by the present disclosure may be administered to a patient susceptible to or otherwise at risk of a particular disease or infection. Hence, a prophylactically effective amount is an amount sufficient to prevent, hinder or retard a disease state or its symptoms.

An appropriate dosage of the pharmaceutical composition may be determined according to any one of several well-established protocols. For example, animal studies, such as studies using mice or rats, may be used to determine an appropriate dose of a pharmaceutical compound. The results from animal studies can be extrapolated to determine doses for use in other species, such as for example, humans. For example, the efficacy of (2R)-2-phenylcarbonyloxypropyl (2S)-2-amino-3-(3,4-dihydroxyphenyl)propanoate mesylate, hydrate and compositions thereof for treating Parkinson's disease may be assessed using animal models of Parkinson's disease and in clinical studies. Animal models of Parkinson's disease are known (O'Neil et al., *CNS Drug Rev.* 2005, 11(1), 77-96; Faulkner et al., *Ann. Pharmacother.* 2003, 37(2), 282-6; Van Blercom et al., *Clin Neuropharmacol.* 2004, 27(3), 124-8; Cho et al., *Biochem. Biophys. Res. Commun.* 2006, 341, 6-12; and Emborg, *J. Neuro. Meth.* 2004, 139, 121-143).

Levodopa prodrugs are precursors of dopamine. Thus, levodopa prodrug mesylate, hydrate provided by the present disclosure may be administered to a patient suffering from any disease or disorder for which the parent drug, levodopa, is known or hereafter discovered to be therapeutically effective. Levodopa prodrug mesylate, hydrate may be administered to a patient, such as a human, to treat a disease or disorder such as Parkinson's disease. The methods comprise administering to a patient in need of such treatment a therapeutically effective amount of levodopa prodrug mesylate, hydrate. In therapeutic methods provided by the present disclosure, a therapeutically effective amount of levodopa prodrug mesylate, hydrate may be administered to a patient suffering from a disease such as Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, or excessive daytime sleepiness. In prophylactic methods provided by the present disclosure a therapeutically effective amount of levodopa prodrug mesylate, hydrate may be administered to a patient at risk of developing a disease such as Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, or excessive daytime sleepiness.

Levodopa is well known to be effective in treating Parkinson's disease (see Fahn et al., *N Engl J Med* 2004, 351(24), 2498-2508).

Low doses of levodopa given as adjunctive treatment with typical antipsychotic drugs improves the clinical outcome in schizophrenia (see Jaskiw and Popli, *Psychopharmacology* 2004, 171, 365-374) and suggests an enhanced effect on negative symptoms and cognitive impairment without worsening of psychotic symptoms (Alpert and Friedhoff, *Am J Psychiatry* 1980, 135, 1329-32; Bruno and Bruno, *Acta Psychiatr Scand,* 1966, 42, 264-71; Buchanan et al., *Aust N Z J Psychiatry* 1975, 9, 269-71; Gerlach and Luhdorf, *Psychopharmacologia* 1975, 44, 105-110; Inanaga et al., *Folia Psychiatr Neurol Jpn* 1975, 29, 123-43; and Kay and Opler, *Int J Psychiat Med* 1985-86, 15, 293-98).

Levodopa has been shown to be effective in treating cognitive impairment disorders such as cognitive dysfunction in patients with Parkinson's disease (Kulisevsky, *Drugs Aging* 2000, 16(5), 365-79) and improving word learning in healthy patients (Knecht et al., *Ann. Neurol* 2004, 56(1), 20-6).

Levodopa has been shown to be effective in treating restless legs syndrome (Ondo and Jankovic, *Neurology* 1996, 47, 14354; and von Scheele, *Lancet* 1986, 2(8504), 426-7).

Studies suggest that levodopa can be useful in treating periodic movement disorders such as tardive dyskinesia (Rascol and Fabre, *Clinical Neuropharmacology* 2001, 24(6), 313-323; Soares and McGrath, *Schizophr Res* 1999, 39(1), 1-16; and Ebadi and Srnivasan, *Pharmacological Reviews* 1996, 47(4), 575-604), dystonia (Jankovic, *Lancet Neurol* 2006, 5, 864-72), and motor recovery after stroke (Scheidtmann et al., *The Lancet,* 2001, 358, 787-790; and Floel et al., *Neurology* 2005, 65(3), 4724).

Tardive dyskinesia is a type of dyskinesia that is distinct from levodopa-induced dyskinesia (Rascol and Fabre, *Clinical Neuropharmacology* 2001, 24(6), 313-323). Levodopa-induced dyskinesia is usually associated with the treatment of Parkinson's disease. Tardive dyskinesia is a type of dyskinesia that is typically induced by neuroleptics, i.e. drugs used for treating psychotic disorders. For example, Soares and McGrath, *Schizophr Res* 1999, 39(1), 1-16 disclose that levodopa can be used to treat tardive dyskinesia.

Levodopa has shown effectiveness in treating rigidity associated with Huntington's disease (Racette and Perlmutter, *J Neurol Neurosurg Psychiatry* 1998, 65(4), 577-9).

The use of levodopa for treating hypertension is disclosed, for example, by Doggrell, *Expert Opin Investig Drugs* 2002, 11(5), 631-44. Low dose levodopa can be used to induce diuresis and naturesis, which can be useful in treating hypertension.

The use of levodopa for treating excessive daytime sleepiness, especially excessive daytime sleepiness associated with Parkinson's disease is disclosed, for example, by O'Sulleabhaim and Dewey, *Arch Neurol* 2002, 59(6), 986-989. Levodopa has also been shown to be effective in treating excessive daytime sleepiness in patients with narcolepsy (Boivin and Montplaisir, *Neurology* 1991, 41, 1267-1269) and hypersomnia (Silber, *Neurologic Clinics* 2001, 19(1), 173-86; Paus et al., *Movement Disorders* 2003, 18(6), 659-667; Hogl et al., *Movement Disorders* 2003, 18(3), 319-323; and O'Suilleabhain and Dewey, *Arch Neurol* 2002, 59, 986-989).

In certain embodiments, levodopa prodrug mesylate, hydrate or pharmaceutical composition thereof may be co-administered with another therapeutic agent or drug, such as a decarboxylase inhibitor such as carbidopa or benserazide, which may act as a protectant to inhibit or prevent premature decarboxylation of the levodopa prodrug mesylate, hydrate and/or the levodopa metabolite. Levodopa prodrug mesylate hydrate may be delivered from the same dosage form as the L-aromatic amino acid decarboxylase inhibitor or from a different dosage form. Levodopa prodrug mesylate, hydrate may be administered at the same time as, prior to, or subsequent to, the administration of a decarboxylase inhibitor. Levodopa prodrug mesylate, hydrate together with a decarboxylase inhibitor can be administered to a patient, such as a human, to treat a disease such as Parkinson's disease.

In certain embodiments, levodopa prodrug mesylate or pharmaceutical composition thereof together with at least one decarboxylase inhibitor may be used to treat a disease for which levodopa is known or believed to be effective in treating. In certain embodiments, levodopa prodrug mesylate, hydrate or pharmaceutical composition thereof may be useful for the treatment of Parkinson's disease. When used to treat Parkinson's disease, levodopa prodrug mesylate, hydrate or pharmaceutical composition thereof may be administered or applied in combination with a decarboxylase inhibitor such as carbidopa and/or benserazide. Additionally, the therapeutic effectiveness of the above combinations may be enhanced by co-administration of another pharmaceutically active agent such as a catechol-O-methyltransferase (COMT) inhibitor such as entacapone and/or tolecapone. Further, in certain embodiments, levodopa prodrug mesylate, hydrate or pharmaceutical composition thereof may be administered to a patient, such as a human, together with (i) a decarboxylase inhibitor such as carbidopa or benserazide, (ii) a COMT inhibitor such as entacopone or tolecapone, or (iii) a combination of a decarboxylase inhibitor such as carbidopa or benserazide and a COMT inhibitor such as entacopone or tolecapone, to treat a disease or disorder such as Parkinson's disease.

(2R)-2-Phenylcarbonyloxypropyl (2S)-2-amino-3-(3,4-dihydroxyphenyl)propanoate mesylate, hydrate may be included in a pharmaceutical composition and/or dosage form adapted for oral administration, although (2R)-2-phenylcarbonyloxypropyl (2S)-2-amino-3-(3,4-dihydroxyphenyl)propanoate mesylate, hydrate may also be administered by any other convenient mute, such as for example, by injection, infusion, inhalation, transdermal, or absorption through epithelial or mucosal membranes (e.g., oral, rectal, and/or intestinal mucosa).

(2R)-2-Phenylcarbonyloxypropyl (2S)-2-amino-3-(3,4-dihydroxyphenyl)propanoate mesylate, hydrate or pharmaceutical compositions thereof may provide therapeutic or prophylactic plasma and/or blood concentrations of levodopa following oral administration to a patient. The carboxyl ester promoiety of (2R)-2-phenylcarbonyloxypropyl (2S)-2-amino-3-(3,4-dihydroxyphenyl)propanoate mesylate, hydrate may be cleaved in vivo either chemically and/or enzymatically to release the parent drug, levodopa. One or more enzymes present in the stomach, intestinal lumen, intestinal tissue, blood, liver, brain, or any other suitable tissue of a patient may enzymatically cleave the promoiety of the administered compounds. For example, the carboxyl ester promoiety of (2R)-2-phenylcarbonyloxypropyl (2S)-2-amino-3-(3,4-dihydroxyphenyl)propanoate mesylate, hydrate may be cleaved prior to absorption from the gastrointestinal tract (e.g., within the stomach or intestinal lumen) and/or after absorption from the gastrointestinal tract (e.g., in intestinal tissue, blood, liver, or other suitable tissue of a mammal). In certain embodiments, (2R)-2-phenylcarbonyloxypropyl (2S)-2-amino-3-(3,4-dihydroxyphenyl)propanoate mesylate, hydrate may be actively transported across the intestinal endothelium by organic cation transporters expressed throughout the gastrointestinal tract including the small intestine and colon. Levodopa may remain conjugated to the carboxyl ester promoiety during transit across the intestinal mucosal barrier to prevent or minimize presystemic metabolism. In certain embodiments, (2R)-2-phenylcarbonyloxypropyl (2S)-2-amino-3-(3,4-dihydroxyphenyl)propanoate mesylate, hydrate is essentially not metabolized to levodopa within gastrointestinal enterocytes, but is metabolized to levodopa within the systemic circulation, for example in the plasma. In such embodiments, (2R)-2-phenylcarbonyloxypropyl (2S)-2-amino-3-(3,4-dihydroxyphenyl)propanoate mesylate may be absorbed into the systemic circulation from the small and large intestines either by active transport, passive diffusion, or by both active and passive processes. Cleavage of the promoiety from (2R)-2-phenylcarbonyloxypropyl (2S)-2-amino-3-(3,4-dihydroxyphenyl)propanoate mesylate, hydrate after absorption from the gastrointestinal tract may allow the levodopa prodrug mesylate, hydrate to be absorbed into the systemic circulation either by active transport, passive diffusion, or by both active and passive processes. The mechanism of cleavage is not important to the present embodiments. For example, the carboxyl ester promoiety can be cleaved after absorption from the gastrointestinal tract, for example, in intestinal tissue, blood, liver, or other suitable tissue of a mammal.

(2R)-2-Phenylcarbonyloxypropyl (2S)-2-amino-3-(3,4-dihydroxyphenyl)propanoate mesylate, hydrate may be administered to achieve therapeutically effective levodopa plasma concentrations and using a similar dosing regimen as described in the art for levodopa. For example, (2R)-2-phenylcarbonyloxypropyl (2S)-2-amino-3-(3,4-dihydroxyphenyl)propanoate mesylate, hydrate can be useful in treating Parkinson's disease by administration of (2R)-2-phenylcarbonyloxypropyl (2S)-2-amino-3-(3,4-dihydroxyphenyl)propanoate mesylate, hydrate together with a decarboxylase inhibitor such as carbidopa, in certain embodiments by the oral route, to a mammalian subject in need of the treatment. In a human subject weighing about 70 kg, (2R)-2-phenylcarbonyloxypropyl (2S)-2-amino-3-(3,4-dihydroxyphenyl)propanoate mesylate, hydrate can be administered at a dose over time having an equivalent weight of levodopa from about 10 mg to about 10 g per day, and in certain embodiments, an equivalent weight of levodopa from about 100 mg to about 3 g per day. Accordingly, a dose of (2R)-2-phenylcarbonyloxypropyl (2S)-2-amino-3-(3,4-dihydroxyphenyl)propanoate mesylate, hydrate can be administered at a dose over time from about 20 mg to about 20 g per day, and in certain embodiments, from about 200 mg to about 7 g per day. A dose of (2R)-2-phenylcarbonyloxypropyl (2S)-2-amino-3-(3,4-dihydroxyphenyl)propanoate mesylate, hydrate taken at any one time can have an equivalent weight of levodopa from about 10 mg to about 3 g, and in certain embodiments, from about 100 mg to about 2 g. A dose of (2R)-2-phenylcarbonyloxypropyl (2S)-2-amino-3-(3,4-dihydroxyphenyl)propanoate mesylate, hydrate taken at any one time can be from about 20 mg to about 7 g, and in certain embodiments, from about 200 mg to about 5 g. A dose can be adjusted by one skilled in the art based on several factors, including, for example, the body weight and/or condition of the subject treated, the dose of the decarboxylase inhibitor being administered, the severity of the disease being treated, the incidence of side effects, the manner of administration, and the judgment of the prescribing physician. Appropriate doses and regimens may be determined by methods known to one skilled in the art.

(2R)-2-Phenylcarbonyloxypropyl (2S)-2-amino-3-(3,4-dihydroxyphenyl)propanoate mesylate, hydrate may be assayed in vitro and in vivo for the desired therapeutic or prophylactic activity prior to use in humans. In vivo assays may also be used to determine whether administration of (2R)-2-phenylcarbonyloxypropyl (2S)-2-amino-3-(3,4-dihydroxyphenyl)propanoate mesylate, hydrate is therapeutically effective. (2R)-2-Phenylcarbonyloxypropyl (2S)-2-amino-3-(3,4-dihydroxyphenyl)propanoate mesylate, hydrate may also be demonstrated to be effective and safe using animal model systems.

In certain embodiments, a therapeutically effective dose of (2R)-2-phenylcarbonyloxypropyl (2S)-2-amino-3-(3,4-dihydroxyphenyl)propanoate mesylate, hydrate may provide therapeutic benefit without causing substantial toxicity. Toxicity of (2R)-2-phenylcarbonyloxypropyl (2S)-2-amino-3-(3, 4-dihydroxyphenyl)propanoate mesylate, hydrate may be determined using standard pharmaceutical procedures and may be ascertained by one skilled in the art. The dose ratio between toxic and therapeutic effect is the therapeutic index. A dosage of (2R)-2-phenylcarbonyloxypropyl (2S)-2-amino-3-(3,4-dihydroxyphenyl)propanoate mesylate, hydrate may be within a range capable of establishing and maintaining a therapeutically effective circulating plasma and/or blood concentration of levodopa that exhibits little or no toxicity.

In addition to the use of (2R)-2-phenylcarbonyloxypropyl (2S)-2-amino-3-(3,4-dihydroxyphenyl)propanoate mesylate, hydrate and compositions comprising (2R)-2-phenylcarbonyloxypropyl (2S)-2-amino-3-(3,4-dihydroxyphenyl)propanoate mesylate, hydrate provided by the present disclosure for treating Parkinson's disease, levodopa prodrugs mesylate, hydrate and compositions thereof may also be useful for treating other dopamine-related diseases. Dopamine-related diseases can be characterized by either insufficient or excessive functional dopaminergic activity in the central nervous system. Examples of other dopamine-related diseases include, but are not limited to, affective disorders such as depression and attention deficit disorder; psychotic disorders such as schizophrenia and manic depression; cognitive impairment disorders such as mild cognitive impairment; movement disorders such as restless legs syndrome, periodic limb movement disorders, tardive dyskinesia, hypertension, Huntington's disease, and Tourette's syndrome; addictive disorders such as alcohol addiction or abuse, nicotine addiction or abuse, and drug addiction and abuse; congestive heart failure; and excessive daytime sleepiness. For the treatment of these and other dopamine-related diseases, (2R)-2-phenylcarbonyloxypropyl (2S)-2-amino-3-(3,4-dihydroxyphenyl)propanoate mesylate, hydrate may be co-administered with an additional active agent such as, for example, a decarboxylase inhibitor and/or a COMT inhibitor. Therapeutically effective doses for treating dopamine-related diseases may be determined by methods disclosed herein for the treatment of Parkinson's disease and/or by methods known in the art. (2R)-2-Phenylcarbonyloxypropyl (2S)-2-amino-3-(3,4-dihydroxyphenyl)propanoate mesylate, hydrate or pharmaceutical compositions thereof may also be used to modulate dopamine levels in a patient.

In certain embodiments, (2R)-2-phenylcarbonyloxypropyl (2S)-2-amino-3-(3,4-dihydroxyphenyl)propanoate mesylate, hydrate may be used in combination therapy with at least one other therapeutic agent. Pharmaceutical compositions provided by the present disclosure may include, in addition to (2R)-2-phenylcarbonyloxypropyl (2S)-2-amino-3-(3,4-dihydroxyphenyl)propanoate mesylate, hydrate one or more therapeutic agents effective for treating the same or different disease, disorder, or condition.

Methods provided by the present disclosure include administration of (2R)-2-phenylcarbonyloxypropyl (2S)-2-amino-3-(3,4-dihydroxyphenyl)propanoate mesylate, hydrate or pharmaceutical compositions thereof and one or more other therapeutic agents, provided that the combined administration does not inhibit the therapeutic efficacy of (2R)-2-phenylcarbonyloxypropyl (2S)-2-amino-3-(3,4-dihydroxyphenyl)propanoate mesylate, hydrate or levodopa and/or does not produce adverse combination effects.

(2R)-2-Phenylcarbonyloxypropyl (2S)-2-amino-3-(3,4-dihydroxyphenyl)propanoate mesylate, hydrate and another therapeutic agent or agents may act additively or synergistically. In certain embodiments, pharmaceutical compositions provided by the present disclosure can be administered concurrently with the administration of another therapeutic agent, which may be contained in the same pharmaceutical composition as, or in a different composition from that containing (2R)-2-phenylcarbonyloxypropyl (2S)-2-amino-3-(3,4-dihydroxyphenyl)propanoate mesylate, hydrate. In certain embodiments, (2R)-2-phenylcarbonyloxypropyl (2S)-2-amino-3-(3,4-dihydroxyphenyl)propanoate mesylate, hydrate may be administered prior or subsequent to administration of another therapeutic agent. In certain embodiments of combination therapy, the combination therapy can comprise alternating between administering a composition provided by the present disclosure and a composition comprising another therapeutic agent, e.g., to minimize adverse side effects associated with a particular drug. When (2R)-2-phenylcarbonyloxypropyl (2S)-2-amino-3-(3,4-dihydroxyphenyl)propanoate mesylate, hydrate is administered concurrently with another therapeutic agent that can potentially produce adverse side effects including, but not limited to, toxicity, the therapeutic agent may advantageously be administered at a dose that falls below the threshold at which the adverse side effect is elicited.

In certain embodiments, (2R)-2-phenylcarbonyloxypropyl (2S)-2-amino-3-(3,4-dihydroxyphenyl)propanoate mesylate, hydrate may further be administered together with one or more compounds that enhance, modulate, and/or control the release, bioavailability, therapeutic efficacy, therapeutic potency, and/or stability of (2R)-2-phenylcarbonyloxypropyl (2S)-2-amino-3-(3,4-dihydroxyphenyl)propanoate mesylate, hydrate and/or levodopa. For example, to enhance therapeutic efficacy levodopa prodrug mesylate hydrate may be co-administered with one or more active agents to increase the absorption or diffusion of (2R)-2-phenylcarbonyloxypropyl (2S)-2-amino-3-(3,4-dihydroxyphenyl)propanoate mesylate, hydrate and/or levodopa through the gastrointestinal tract, or to modify degradation of the (2R)-2-phenylcarbonyloxypropyl (2S)-2-amino-3-(3,4-dihydroxyphenyl)propanoate mesylate, hydrate and/or levodopa in the systemic circulation. In certain embodiments, (2R)-2-phenylcarbonyloxypropyl (2S)-2-amino-3-(3,4-dihydroxyphenyl)propanoate mesylate, hydrate may be co-administered with an active agent having pharmacological effects that enhance the therapeutic efficacy of levodopa after being released from (2R)-2-phenylcarbonyloxypropyl (2S)-2-amino-3-(3,4-dihydroxyphenyl)propanoate mesylate, hydrate. In certain embodiments, (2R)-2-phenylcarbonyloxypropyl (2S)-2-amino-3-(3,4-dihydroxyphenyl)propanoate mesylate, hydrate may be co-administered with an active agent having pharmacological effects that enhance the therapeutic efficacy of dopamine after being released from levodopa.

In certain embodiments, (2R)-2-phenylcarbonyloxypropyl (2S)-2-amino-3-(3,4-dihydroxyphenyl)propanoate mesylate, hydrate or pharmaceutical compositions comprising (2R)-2-phenylcarbonyloxypropyl (2S)-2-amino-3-(3,4-dihydroxyphenyl)propanoate mesylate, hydrate may be administered to a patient together with another compound for treating Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, or excessive daytime sleepiness.

Examples of drugs useful for treating Parkinson's disease include amantadine, baclofen, biperiden, benztropine, orphenadrine, procyclidine, trihexyphenidyl, levodopa, carbidopa, andropinirole, apomorphine, benserazide, bromocriptine, budipine, cabergoline, eliprodil, eptastigmine, ergoline, galanthamine, lazabemide, lisuride, mazindol, memantine, mofegiline, pergolide, piribedil, pramipexole, propentofylline, rasagiline, remacemide, ropinirole, selegiline, spheramine, terguride, entacapone, and tolcapone.

Examples of drugs useful for treating mood disorders such as depression include tricyclic antidepressants such as amitriptyline, amoxapine, clomipramine, desipramine, doxepin, imipramine, maprotiline, nortriptyline, protriptyline, and trimipramine; selective serotonin reuptake inhibitors such as citalopram, escitalopram, fluoxetine, fluvoxamine, paroxetine, and sertraline; serotonin-noradrenaline reuptake inhibitors such as venlafaxine, duloxetine, sibutramine, and milnacipran; monoamine oxidase inhibitors such as phenelzine and tranylcypromine; and psychostimulants such as dextroamphetamine and methylphenidate. Other antidepressants include benmoxine, butriptyline, dosulepin, imipramine, kitanserin, lofepramine, medifoxamine, mianserin, mirtazapine, viloxazine, cotinine, nisoxetine, reboxetine, tianeptine, acetaphenazine, binedaline, brofaromine, cericlamine, clovoxamine, iproniazid, isocarboxazid, moclobemide, phenyhydrazine, selegiline, sibutramine, ademetionine, adrafinil, amesergide, amisulpride, amperozide, benactyzine, bupropion, caroxazone, gepirone, idazoxan, metralindole, minaprine, nefazodone, nomifensine, ritanserin, roxindole, S-adenosylmethionine, escitalopram, tofenacin, trazodone, tryptophan, zalospirone, and Saint John's wort. (2R)-2-Phenylcarbonyloxypropyl(2S)-2-amino-3-(3,4-dihydroxyphenyl)propanoate mesylate, hydrate and pharmaceutical compositions thereof may also be used in conjunction with psychotherapy or electroconvulsive therapy to treat mood disorders such as depression.

Examples of drugs useful for treating attention deficit disorder include atomoxetine, bupropion, dexmethylphenidate, dextroamphetamine, metamphetamine, methylphenidate, and pemoline.

Examples of drugs for treating schizophrenia include aripiprazole, loxapine, mesoridazine, quetiapine, reserpine, thioridazine, trifluoperazine, and ziprasidone. The use of levodopa prodrugs in combination with at least one antipsychotic agent in an amount that is effective for treating a positive symptom of schizophrenia is disclosed in Tran, U.S. Patent Application Publication No. 2008/0070984, which is incorporated by reference herein in its entirety. The at least one antipsychoitic agent can be chosen from, for example, chlorpromazine, haloperidol, fluphenazine, loxapine, mesoridazine, molindone, perphenazine, pimozide, raclopride, remoxipride, thioridazine, thiothixene, and trifluoperazine.

Examples of drugs useful for treating manic depression include carbamazepine, clonazepam, clonidine, valproic acid, verapamil, lamotrigine, gabapentin, topiramate, lithium, clozapine, olanzapine, risperidone, quetiapine, ziprasidone, clonazepam, lorazepam, zolipidem, St. John's wort, and omega-3 fatty acids.

Examples of drugs useful for treating cognitive or memory disorders include antipsychotic drugs such as chlorpromazine, fluphenazine, haloperidol, loxapine, mesoridazine, molindone, perphenazine, pimozide, thioridazine, thiothixene, trifluoperazine, aripiprazole, clozapine, olanzapine, quetiapine, risperidone, and ziprasidone; sedatives such as diazepam and lorazepam; benzodiazepines such as alprazolam, chlordiazepoxide, clonazepam, clorazepate, diazepam, lorazepam, and oxazepam; nonsteroidal anti-inflammatory drugs such as aceclofenac, acetaminophen, alminoprofen, amfenac, aminopropylon, amixetrine, aspirin, benoxaprofen, bromfenac, bufexamac, carprofen, celecoxib, choline, salicylate, cinchophen, cinmetacin, clopriac, clometacin, diclofenac, diflunisal, etodolac, fenoprofen, flurbiprofen, ibuprofen, indomethacin, indoprofen, ketoprofen, ketorolac, mazipredone, meclofenamate, nabumetone, naproxen, parecoxib, piroxicam, pirprofen, rofecoxib, sulindac, tolfenamate, tolmetin, and valdecoxib; acetylcholinesterase inhibitors such as donepezil, galantamine, rivastigmine, physostigmine, and tacrine; and N-methyl-D-aspartate (NMDA) receptor blockers such as memantine.

Examples of drugs useful for treating restless legs syndrome include dopaminergics such as levodopa, pergolide mesylate, pramipexole, and rinirole hydrochloride, benzodiazepines such as clonazepam and diazepam, opioids such as codeine, propoxyphene, and oxycodone, and anticonvulsants such as gabapentin, prebabalin, and carbamazepine.

Examples of drugs useful for treating movement disorders such as tardive dyskinesia include reserpine, tetrabenazine, and vitamin E.

Examples of drugs useful for treating Huntington's disease include antipsychotics such as haloperidol, chlorpromazine, and olanzapine; antidepressants such as fluoxetine, sertraline hydrochloride, and nortriptyline; tranquilizers such as benzodiazepines, paroxetine; venlafaxin, and beta-blockers; mood-stabilizers such as lithium, valproate, and carbamazepine; and *Botulinum* toxin.

Examples of drugs useful for treating Tourette's syndrome include haloperidol, pergolide, and pimozide.

Examples of drugs useful for treating hypertension include acebutolol, amiloride, amlodipine, atenolol, benazepril, betaxolol, bisoprolol, candesartan captopril, careolol, carvedilol, chlorothiazide, chlorthalidone, clonidine, diltiazem, doxazosin, enalapril, eplerenone, eprosartan, felodipine, fosinopril, furosemide, guanabenz, guanethidine, guanfacine, hydralazine, hydrochlorothiazide, indapamide, irbesartan, isradipine, labetalol, lisinopril, losartan, methyldopa, metolazone, metoprolol, minoxidil, moexipril, nadolol, nicardipine, nifedipine, nisoldipine, nitroglycerin, olmesartan, perindopril, pindolol, prazosin, propranolol, quinapril, ramipril, reserpine, spironolactone, telmisartan, terazosin, timolol, torsemide, trandolapril, valsartan, and verapamil.

Examples of drugs useful for treating alcohol addiction or abuse include disulfiram, naltrexone, clonidine, methadone, 1-α-acetylmethadol, buprenorphine, and bupropion.

Examples of drugs useful for treating narcotic addiction or abuse include buprenorphine, tramadol, methadone, and naltrexone.

Examples of drugs useful for treating nicotine addiction or abuse include bupropion, clonidine, and nicotine.

Examples of drugs useful for treating congestive heart failure include alllopurinol, amiloride, amlodipine, benazepril, bisoprolol, carvedilol, digoxin, enalapril, eplerenone, fosinopril, furosemide, hydrochlorothiazide, hydralazine, isosorbide dinitrate, isosorbide mononitrate, lisinopril, metoprolol, moexipril, nesiritide, nicardipine, nifedipine, nitroglycerin, perindopril, prazosin, quinapril, ramipril, spironolactone, torsemide, trandolapril, triamcinolone, and valsartan.

Examples of drugs useful for treating excessive daytime sleepiness include dextroamphetamine, methylphenidate, modafinil, and sodium oxybate.

The following examples describe in detail preparation of (2R)-2-phenylcarbonyloxypropyl (2S)-2-amino-3-(3,4-dihydroxyphenyl)propanoate mesylate, hydrate, pharmaceutical compositions thereof, and uses thereof. It will be apparent to one skilled in the art that many modifications, both to materials and methods, may be practiced without departing from the scope of the disclosure. Examples 11 and 12 are prophetic.

Example 1

(2R)-2-Phenylcarbonyloxypropyl (2S)-2-Amino-3-(3,4-dihydroxyphenyl)propanoate Mesylate, Anhydrous (1)

Step A: (2S)-3-(3,4-Dihydroxyphenyl)-2-[(tert-butoxycarbonyl)amino]propanoic acid, tetrabutylammonium salt (1a)

A solution of N-Boc-(L)-Dopa (175 g, 0.59 mol) in methanol (1 L) was cautiously mixed with a methanolic solution of tetrabutylammonium hydroxide (1.0 M, 0.55 L) at 0° C. for 30 min. The mixture was then concentrated under reduced pressure and dried by azeotroping twice with toluene. The residue was crystallized after cooling at 4° C. for 16 h. The resulting crystalline solid was washed with acetone (400 mL×3), collected on a Buchner funnel, and then dried under high vacuum to afford 245 g (83% yield) of the title compound 1a. $^1$H NMR (400 MHz, DMSO-d$_6$): δ 0.94 (t, J=7.6 Hz, 12H), 1.30 (m, 17H), 1.60 (m, 8H), 3.18 (m, 8H), 4.58 (m, 1H), 5.68 (d, J=5.6 Hz, 1H), 6.30 (d, J=7.6 Hz, 1H), 6.46 (d, J=8.0 Hz, 1H), 6.51 (s, 1H), 8.85 (s, 1H); 8.94 (s, 1H).

Step B: (1R)-2-Bromo-1-methylethyl benzoate (1b)

A solution of (2R)-propylene glycol (20.0 g, 262.8 mmol), benzaldehyde (33.4 mL, 328.6 mmol, 1.25 eq) and p-toluenesulfonic acid (2.5 g, 0.05 eq) in benzene (200 mL) was refluxed for 8 h after which water was removed using a Dean-Stark apparatus. The cooled solution was diluted with diethyl ether (100 mL), washed with aqueous NaOH (15%, 100 mL), brined (100 mL) and dried over $Na_2SO_4$. After filtration, removal of solvent under reduced pressure gave 44 g of crude benzaldehyde (2R)-propylene glycolacetal as an oil.

To a solution of the above crude benzaldehyde (2R)-propylene glycolacetal (10.0 g, 60.9 mmol) in hexane (100 mL) was added N-bromosuccinamide (NBS) (11.9 g, 67 mmol, 1.1 eq). The resulting mixture was stirred overnight at room temperature. The suspension was filtered through Celite and the filtrate was diluted with hexane (300 mL), washed with saturated $NaHCO_3$ (100 mL) and brine (100 mL), and dried over $Na_2SO_4$. After filtration, removal of the solvent under reduced pressure gave the title compound 1b (quantitative yield) as an oil. $^1H$ NMR (400 MHz, $CDCl_3$): δ 1.48 (d, J=6.4 Hz, 3H), 3.58 (m, 2H), 5.31 (m, 1H), 7.43 (t, J=7.6 Hz, 2H), 7.53 (t, J=7.6 Hz, 1H), 8.05 (d, J=7.2 Hz, 2H).

Step C: (2R)-2-Phenylcarbonyloxypropyl (2S)-2-(tert-butoxycarbonyl)amino-3-(3,4-dihydroxyphenyl) propanoate (1c)

A suspension of (1R)-2-bromo-1-methylethyl benzoate 1b (4.98 g, 20.6 mmol), (2S)-3-(3,4-dihydroxyphenyl)-2-[(tert-butoxycarbonyl)amino]propanoic acid, tetrabutylammonium salt 1a (7.3 g, 25 mmol), and cesium bicarbonate (4.85 g, 25 mmol) in N,N-dimethylacetamide (100 mL) was stirred at 55° C. for 16 h. The solvent was evaporated under vacuum. Ethyl acetate was added to the residue and the resulting solution was washed with water, then 5% $NaHCO_3$ and brine, and dried over $Na_2SO_4$. After removing the solvent under reduced pressure, chromatography (silica gel, 30% ethyl acetate in hexane) of the residue gave 6.3 g (68% yield) of the title compound 1c as a white solid. $^1H$ NMR (400 MHz, $CD_3OD$): δ 1.25 (s, 9H), 1.40 (d, J=6.4 Hz, 3H), 2.99 (dd, J=7.6, 14.4 Hz, 1H), 3.10 (dd, J=5.6, 14.4 Hz, 1H), 4.24 (dd, J=5.6, 7.4 Hz, 1H), 4.38 (dd, J=6.8, 11.6 Hz, 1H), 4.52 (dd, J=3.2, 11.6 Hz, 1H), 5.40 (m, 1H), 6.53 (dd, J=2.2, 8.4 Hz, 1H), 6.66 (d, J=2.2 Hz, 1H), 6.69 (d, J=8.4 Hz, 1H), 7.47 (t, J=7.6 Hz, 2H), 7.60 (t, J=7.6 Hz, 1H), 8.02 (d, J=7.6 Hz, 2H). MS (ESI) m/z 360.15 $(M+H)^+$ and 358.09 $(M-H)^-$.

Method 1

Step D: (2R)-2-Phenylcarbonyloxypropyl (2S)-2-amino-3-(3,4-dihydroxyphenyl)propanoate hydrochloride (1d)

A solution of (2R)-2-phenylcarbonyloxypropyl (2S)-2-(tert-butoxycarbonyl)amino-3-(3,4-dihydroxyphenyl)propanoate 1c (6.3 g, 13.7 mmol) in 50 mL of 4N HCl in dioxane was stirred at room temperature for 30 min. The mixture was concentrated to dryness under reduced pressure. The resulting residue was dissolved in ca. 20 mL of anhydrous acetonitrile and 4 mL of ether. The solution was refrigerated, and the resulting white precipitate was filtered, washed with ether, and dried under vacuum to afford 4.7 g (87% yield) of the hydrochloride salt 1d as a white solid. $^1H$ NMR (400 MHz, $CD_3OD$): δ 1.40 (d, J=6.4 Hz, 3H), 2.99 (dd, J=7.6, 14.4 Hz, 1H), 3.10 (dd, J=5.6, 14.4 Hz, 1H), 4.24 (dd, J=6, 8 Hz, 1H), 4.38 (dd, J=6.8, 11.6 Hz, 1H), 4.52 (dd, J=3.2, 11.6 Hz, 1H), 5.40 (m, 1H), 6.52 (dd, J=2.2, 8.4 Hz, 1H), 6.66 (d, J=2.2 Hz, 1H), 6.69 (d, J=8.2 Hz, 1H), 7.47 (t, J=7.6 Hz, 2H), 7.60 (t, J=7.6 Hz, 1H), 8.02 (d, J=7.6 Hz, 2H). MS (ESI) m/z 360.15 $(M+H)^+$ and 358.09 $(M-H)^-$.

Step E: (2R)-2-Phenylcarbonyloxypropyl (2S)-2-amino-3-(3,4-dihydroxyphenyl)propanoate mesylate, anhydrous (1)

A solution of $NaHCO_3$ (9.87 g, 117.5 mmol) in water (80 mL) was slowly added to a solution of hydrochloride salt 1d (31.0 g, 78.3 mmol) in water (300 mL). The resulting aqueous suspension was extracted with ethyl acetate (EtOAc) (2×400 mL). The combined EtOAc extract was washed with water, then brine, and dried through $MgSO_4$. Methanesulfonic acid (6.04 mL, 93.12 mmol) was slowly added to the ethyl acetate (EtOAc) solution while stirred. White precipitate formed as soon as the addition of methanesulfonic acid was complete. The suspension was stirred for another 30 min and then filtered. The filter cake was washed three times with ethyl acetate (EtOAc) and vacuum dried overnight to afford 35.4 g (quantitative yield) of anhydrous mesylate salt 1 as a white solid. $^1H$ NMR (400 MHz, $CD_3OD$): δ 1.40 (d, J=6.4 Hz, 3H), 2.70 (s, 3H), 2.98 (dd, J=7.8, 14.6 Hz, 1H), 3.10 (dd, J=5.6, 14.4 Hz, 1H), 4.24 (dd, J=5.8, 7.8 Hz, 1H), 4.38 (dd, J=6.8, 12.0 Hz, 1H), 4.52 (dd, J=3.4, 11.8 Hz, 1H), 5.40 (dp, J=3.2, 6.4 Hz, 1H), 6.52 (dd, J=2.2, 8.2 Hz, 1H), 6.67 (d, J=2.2 Hz, 1H), 6.69 (d, J=8.0 Hz, 1H), 7.47 (t, J=7.6 Hz, 2H), 7.60 (br t, J=7.4 Hz, 1H), 8.01 (d, J=7.6 Hz, 2H). MS (ESI) m/z 360.07 $(M+H)^+$ and 358.01 $(M-H)^-$.

Method 2

Methanesulfonic acid (3.9 mL, 60.1 mmol) was slowly added to a solution of (2R)-2-phenylcarbonyloxypropyl (2S)-2-(tert-butoxycarbonyl)amino-3-(3,4-dihydroxyphenyl)propanoate 1c (11.0 g, 22.1 mmol) in 1,4-dioxane (30 mL) while stirred at room temperature. The mixture was stirred for 2 h. The solution was slowly added to methyl tert-butyl ether (MTBE) (600 mL) with vigorous stirring. The resulting suspension was filtered. The filter cake was washed three times with methyl tert-butyl ether and air dried to afford 5.48 g (54% yield) of anhydrous mesylate salt 1 as an off-white solid.

Method 3

A solution of (2R)-2-phenylcarbonyloxypropyl (2S)-2-(tert-butoxycarbonyl)amino-3-(3,4-dihydroxyphenyl)propanoate is (10.5 g, 21.1 mmol) in 34 mL (6.0 eq) of 4.0 N HCl/1,4-dioxane was stirred at room temperature for 1 h. Methanesulfonic acid (1.48 mL, 22.8 mmol) was slowly added to the reaction mixture while stirred at room temperature. The solution was concentrated under vacuum to afford the anhydrous mesylate salt 1 as a brown solid.

Example 2

Preparation of Crystalline Anhydrous (2R)-2-Phenylcarbonyloxypropyl (2S)-2-Amino-3-(3,4-dihydroxyphenyl)propanoate Mesylate (1)

Anhydrous mesylate salt 1 (10.0 g, 22.0 mmol) was dissolved in 200 mL of isopropanol at 70° C. and the resulting solution was cooled to room temperature. Filtration afforded 5.8 g (58% yield) of the crystalline anhydrous mesylate salt 1 as a white crystalline solid (m.p. 160.5-161.3° C.). Other solvents and methods useful for crystallizing anhydrous (2R)-2-phenylcarbonyloxypropyl (2S)-2-amino-3-(3,4-dihydroxyphenyl)propanoate mesylate 1 are disclosed in Xiang et al., U.S. Pat. No. 7,563,821, which is incorporated by reference its entirety.

Example 3

Preparation of Crystalline (2R)-2-Phenylcarbonyloxypropyl (2S)-2-Amino-3-(3,4-dihydroxyphenyl)propanoate Mesylate, Hydrate Method 1—High Shear Wet Granulation Anhydrous (2R)-2-phenylcarbonyloxypropyl (2S)-2-amino-3-(3,4-dihydroxyphenyl)propanoate mesylate (138.6 g) and hydroxypropylmethyl cellulose (1.4 g) (HPMC E4M, Dow Chemical) were weighed and sieved through an 18-mesh screen. The screened materials were placed into a high shear wet granulator (KG-5 high sheer blender, 5 L bowl, Key International) and pre-blended for 2 min. Water was weighed out (USP, 9.8 g, 7 wt-%). The material was blended for ca. 10-20 min at an impeller speed of 250 rpm and a chopper speed of 2,000 rpm, and a water spray rate of 2 g/min. After granulation the wet granules were milled through a 16-mesh screen with a brush. The milled wet granules were placed in a dryer (UniGlatt Fluid Bed Dryer, Glatt GmbH) and dried for 24 min at an inlet temperature of 65° C. with airflow adjusted at 8-10 SCFM. The dried granules were milled by manually pressing the granules through a 0.055 R screen. As shown by X-ray powder diffraction analysis, the granules comprised a combination of the anhydrous and hydrated forms of (2R)-2-phenylcarbonyloxypropyl (2S)-2-amino-3-(3,4-dihydroxyphenyl)propanoate mesylate (FIG. 4).

Using similar processing conditions and 15 wt-% water, the granules contain predominantly crystalline (2R)-2-phenylcarbonyloxypropyl (2S)-2-amino-3-(3,4-dihydroxyphenyl)propanoate mesylate, hydrate (not shown).

Method 2—Crystallization from Alcohol/Water

Anhydrous (2R)-2-phenylcarbonyloxypropyl (2S)-2-amino-3-(3,4-dihydroxyphenyl)propanoate mesylate (1 g) was suspended in ca. 1 mL isopropanol/water mixture (40/60 v/v). The suspension was stirred at 700 rpm at 25° C. The solid completely dissolved with time (ca. 2 h) and then gradually precipitated out as (2R)-2-phenylcarbonyloxypropyl (2S)-2-amino-3-(3,4-dihydroxyphenyl)propanoate mesylate, hydrate.

Example 4

X-Ray Powder Diffraction (XRPD) Analysis

X-ray powder diffraction (XRPD) analysis was performed using a PANalytical X'Pert Pro X-ray diffractometer. The X-ray source was Cu-k$_{\alpha 1}$ with output voltage of 45 kV and current of 40 mA. The instrument employed para-focusing Bragg-Brentano geometry with incident divergence and scattering slits set at 1/16° and 1/8°, respectively. 0.04-mm radius soller slits were used for both the incident and diffracted beams to remove axial divergence. Powder samples (9-12 mg) were gently pressed onto a single crystal silicon sample holder to form a smooth surface, and samples were spun at 8 sec/revolution throughout the data acquisition process. The samples were scanned from 2° to 40° (2θ) with a step size of 0.017° (2θ°) and a scan speed of 0.067°/sec. Data acquisition was controlled and analyzed with X'Pert Data Collector Software (version 2.2d) and X'Pert Data Viewer (version 1.2c), respectively.

Representative XRPD diffraction patterns of crystalline anhydrous (2R)-2-phenylcarbonyloxypropyl (2S)-2-amino-3-(3,4-dihydroxyphenyl)propanoate mesylate and crystalline (2R)-2-phenylcarbonyloxypropyl (2S)-2-amino-3-(3,4-dihydroxyphenyl)propanoate mesylate, hydrate are shown in FIGS. 4, 5, 7, and 8.

Example 5

Differential Scanning Calorimetry

Differential scanning calorimetry was performed using a TA Instruments Q2000 DSC equipped with a refrigeration cooling system. Samples were loaded into T$_{zero}$ aluminum pans with crimpled lids. A pinhole was made at the center of the lid to prevent pressure buildup during heating. Following equilibration at 20° C., sample pans were heated under a nitrogen atmosphere at a rate of 2° C./min to a final temperature of 200° C. Data acquisition was controlled using a Thermal Advantage Release 4.9.1. The data was analyzed with Universal Analysis 2000 software (version 4.5A).

Crystalline anhydrous (2R)-2-phenylcarbonyloxypropyl (2S)-2-amino-3-(3,4-dihydroxyphenyl)propanoate mesylate prepared from ethanol/water according to Example 2 exhibited a melt transition beginning at about 158.0° C., with a peak maximum at about 161.0° C. and having a ΔH of about 79.51 J/g (FIG. 2, dashed line).

Crystalline (2R)-2-phenylcarbonyloxypropyl (2S)-2-amino-3-(3,4-dihydroxyphenyl)propanoate mesylate, hydrate prepared from isopropanol/water according to Example 3, Method 2 exhibited an endothermic/exothermic transition at about 75° C., which is consistent with dehydration and recrystallization of anhydrous (2R)-2-phenylcarbonyloxypropyl (2S)-2-amino-3-(3,4-dihydroxyphenyl)propanoate mesylate (FIG. 2, solid line). At higher temperatures, the anhydrous (2R)-2-phenylcarbonyloxypropyl (2S)-2-amino-3-(3,4-dihydroxyphenyl)propanoate mesylate exhibited a melt transition beginning at about 155.5° C., with a peak maximum at about 160.9° C., and having a ΔH of about 61.5 J/g (FIG. 2, dashed line).

Example 6

Thermogravimetric Analysis of Crystalline (2R)-2-Phenylcarbonyloxypropyl (2S)-2-Amino-3-(3,4-dihydroxyphenyl)propanoate Mesylate, Hydrate Thermogravimetric analyses were performed using a TA Instruments Q5000 thermogravimetric analyzer equipped with a refrigerated cooling system. Samples were loaded into platinum sample pans, inserted into the thermogravimetric furnace, and heated to 200° C. at a rate of 2° C./minute under a nitrogen atmosphere. Data acquisition was controlled by Thermal Advantage Release 4.9.1. The data was analyzed using Universal Analysis 2000 software (version 4.5A).

Thermogravimetric analysis of crystalline (2R)-2-phenylcarbonyloxypropyl (2S)-2-amino-3-(3,4-dihydroxyphenyl)propanoate mesylate, hydrate crystallized from propanol/water according to Example 3, Method 2 showed about 5.5% weight loss from 25° C. to 80° C. The weight loss between 25° C. and 80° C. can be attributed to hydrate water loss: As determined by Karl-Fisher analysis, the water content of the anhydrous form was about 0.5 wt-% and the water content of the hydrate was about 5.6 wt-%. A monohydrate corresponds to a water content of about 3.8 wt-% and a dihydate to a water content of about 7.3 wt-%. A sesqui-hydrate (1.5 moles water to 1 mole of compound) corresponds to a water content of about 5.6 wt-%.

Example 7

Water Sorption/Desorption

Figure 3:
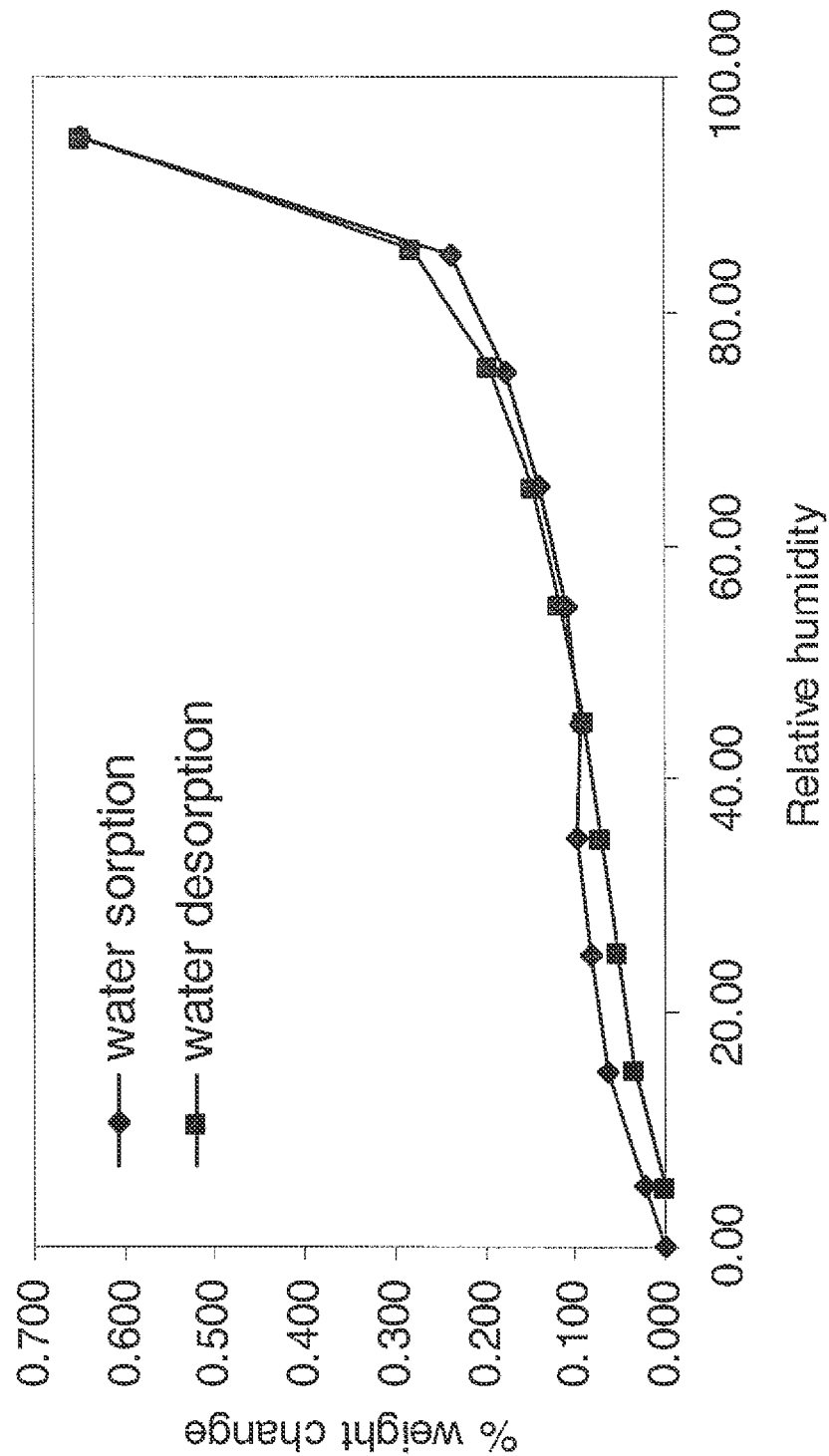
FIG. 3 shows the sorption and desorption of water from (2R)-2-phenylcarbonyloxypropyl (2S)-2-amino-3-(3,4-dihydroxyphenyl)propanoate mesylate, hydrate at about 25° C. as a function of percent relative humidity (% RH).

The hygroscopicity of (2R)-2-phenylcarbonyloxypropyl (2S)-2-amino-3-(3,4-dihydroxyphenyl)propanoate mesylate, hydrate was evaluated during one vapor sorption-desorption cycle using a VTI SGA-100 dynamic vapor sorption analyzer. (2R)-2-Phenylcarbonyloxypropyl (2S)-2-amino-3-(3,4-dihydroxyphenyl)propanoate mesylate, hydrate was first dried at 25° C. for 180 min under a nitrogen atmosphere. The material was considered equilibrated when the weight change during 2 min was less than 0.01%. To evaluate the vapor sorption-desorption at 25° C., the dried (2R)-2-phenylcarbonyloxypropyl (2S)-2-amino-3-(3,4-dihydroxyphenyl)propanoate mesylate, hydrate was exposed to a humidity cycle ramped (and deramped) from 5% RH to 95% RH at 10% RH intervals. At each humidity interval, the material was equilibrated as determined by a less than 0.01% weight change during 5 min. FIG. 3 shows the humidity-dependent reversible sorption and desorption of water vapor by (2R)-2-phenylcarbonyloxypropyl (2S)-2-amino-3-(3,4-dihydroxyphenyl)propanoate mesylate, hydrate.

Example 8

Interconversion of the Anhydrous and Hydrated Crystalline Forms of (2R)-2-Phenylcarbonyloxypropyl (2S)-2-amino-3-(3,4-dihydroxyphenyl)propanoate Mesylate The anhydrous and hydrated crystalline forms of (2R)-2-phenylcarbonyloxypropyl (2S)-2-amino-3-(3,4-dihydroxyphenyl)propanoate mesylate interconvert depending on the water content of the environment.

Figure 7:
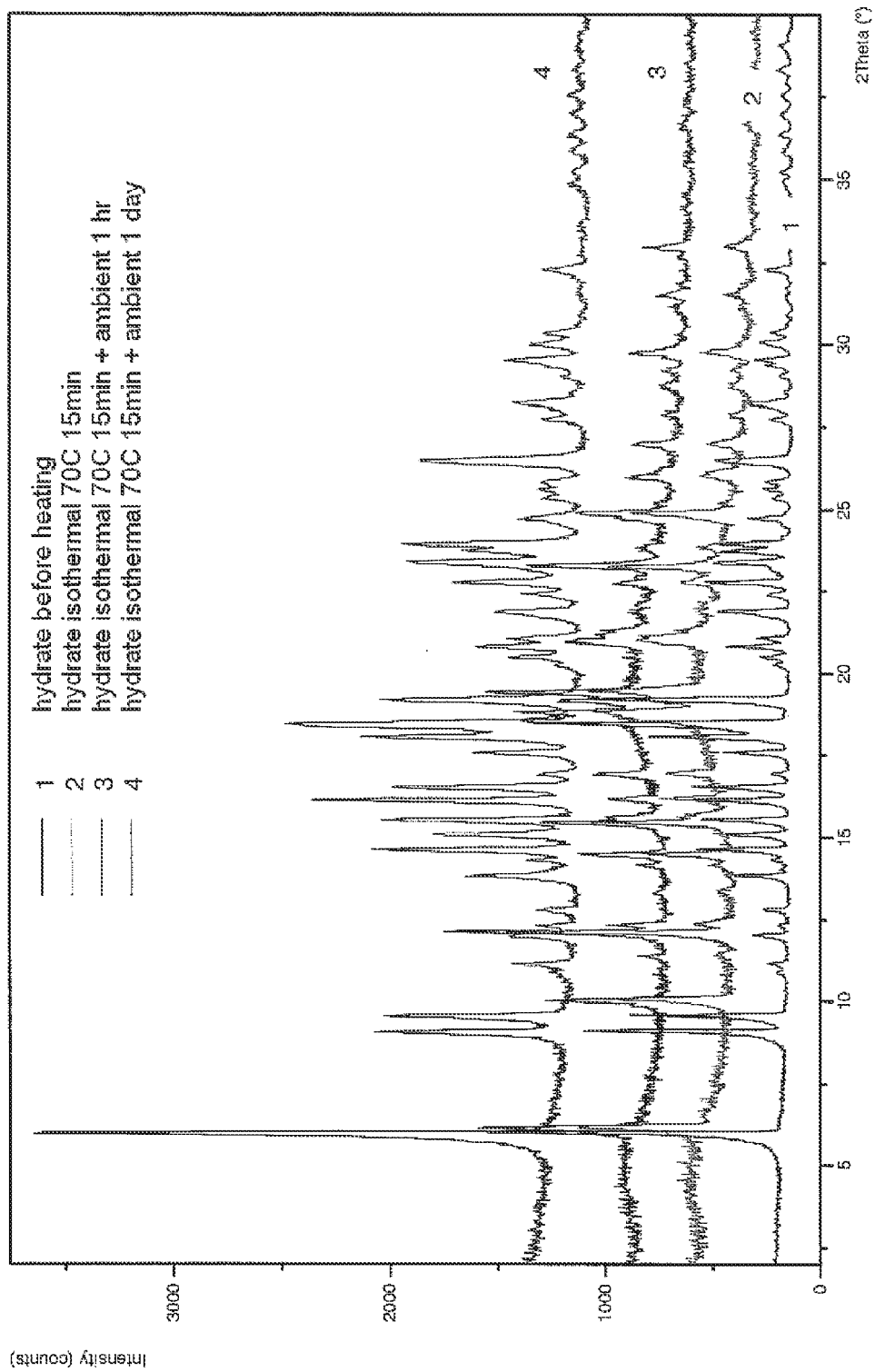
FIG. 7 shows X-ray powder diffraction patterns of (2R)-2-phenylcarbonyloxypropyl (2S)-2-amino-3-(3,4-dihydroxyphenyl)propanoate mesylate, hydrate before (pattern 1) and after (pattern 2) heating at 70° C., and after exposure to room temperature (25° C.) and humidity (40-60% RH) for 1 hour (pattern 3) and for 24 hours (pattern 4).

When heated from room temperature (25° C.) to 70° C. at a rate of 2° C./min and then held at 70° C. for 15 min, crystalline (2R)-2-phenylcarbonyloxypropyl (2S)-2-amino-3-(3,4-dihydroxyphenyl)propanoate mesylate, hydrate (pattern 1) is converted to a transient/metastable crystalline form (patterns 2 and 3) as shown in FIG. 7. When left at room temperature and humidity for 1 day, the transient/metastable crystalline form reverts to crystalline (2R)-2-phenylcarbonyloxypropyl (2S)-2-amino-3-(3,4-dihydroxyphenyl)propanoate mesylate, hydrate (pattern 4).

Figure 8:
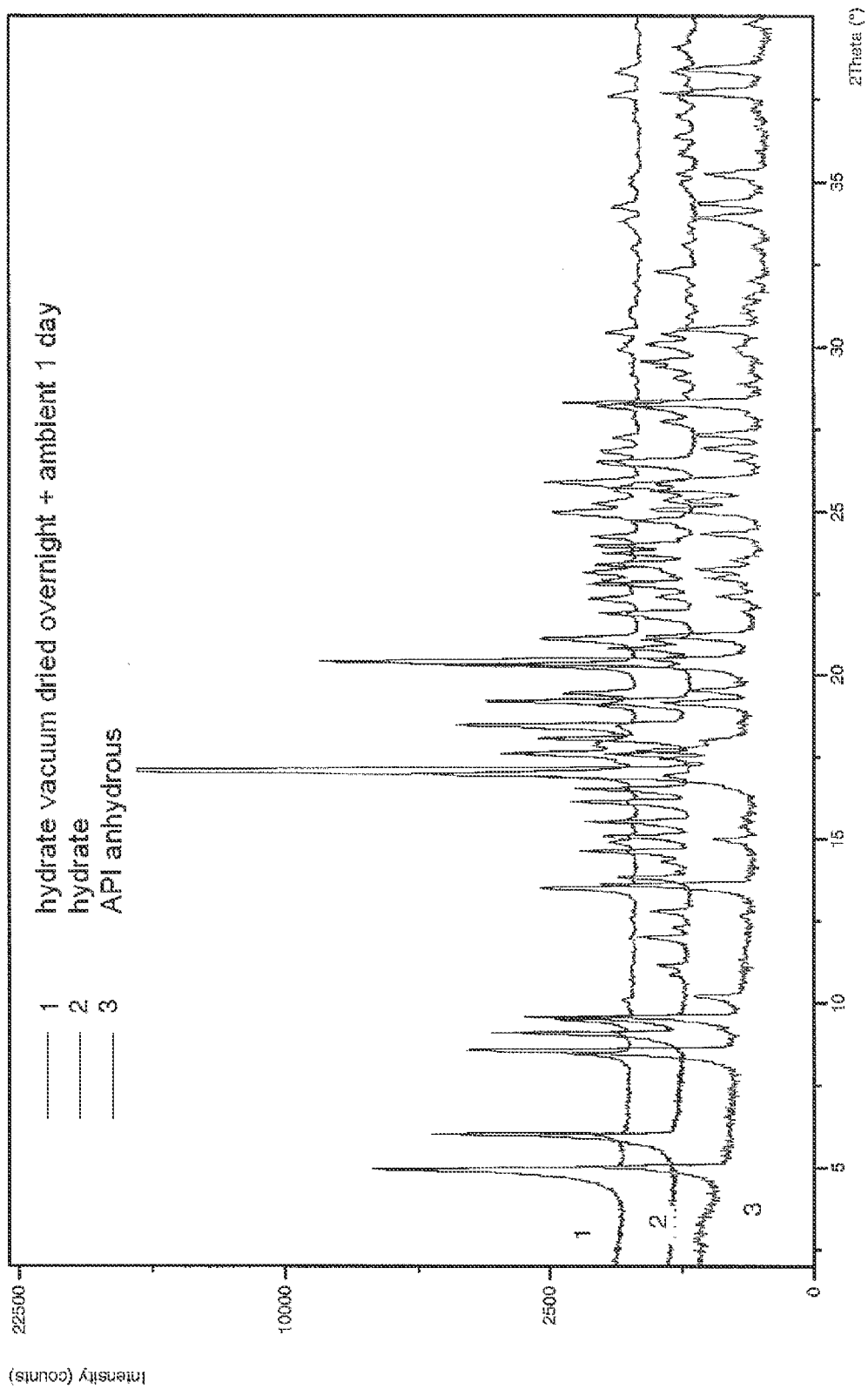
FIG. 8 shows X-ray powder diffraction patterns of anhydrous (2R)-2-phenylcarbonyloxypropyl (2S)-2-amino-3-(3,4-dihydroxyphenyl)propanoate mesylate (pattern 3) and (2R)-2-phenylcarbonyloxypropyl (2S)-2-amino-3-(3,4-dihydroxyphenyl)propanoate mesylate, hydrate before (pattern 2) and after overnight vacuum drying and exposure to room temperature (25° C.) and humidity (40-60% RH) for 1 day (pattern 1).

When crystalline (2R)-2-phenylcarbonyloxypropyl (2S)-2-amino-3-(3,4-dihydroxyphenyl)propanoate mesylate, hydrate (pattern 2) is vacuum dried overnight and then maintained at room temperature and humidity (25° C. and 40-60% RH) for one day, a mixture of crystalline anhydrous and hydrate forms (pattern 1) are observed as shown in FIG. 8.

Figure 6:
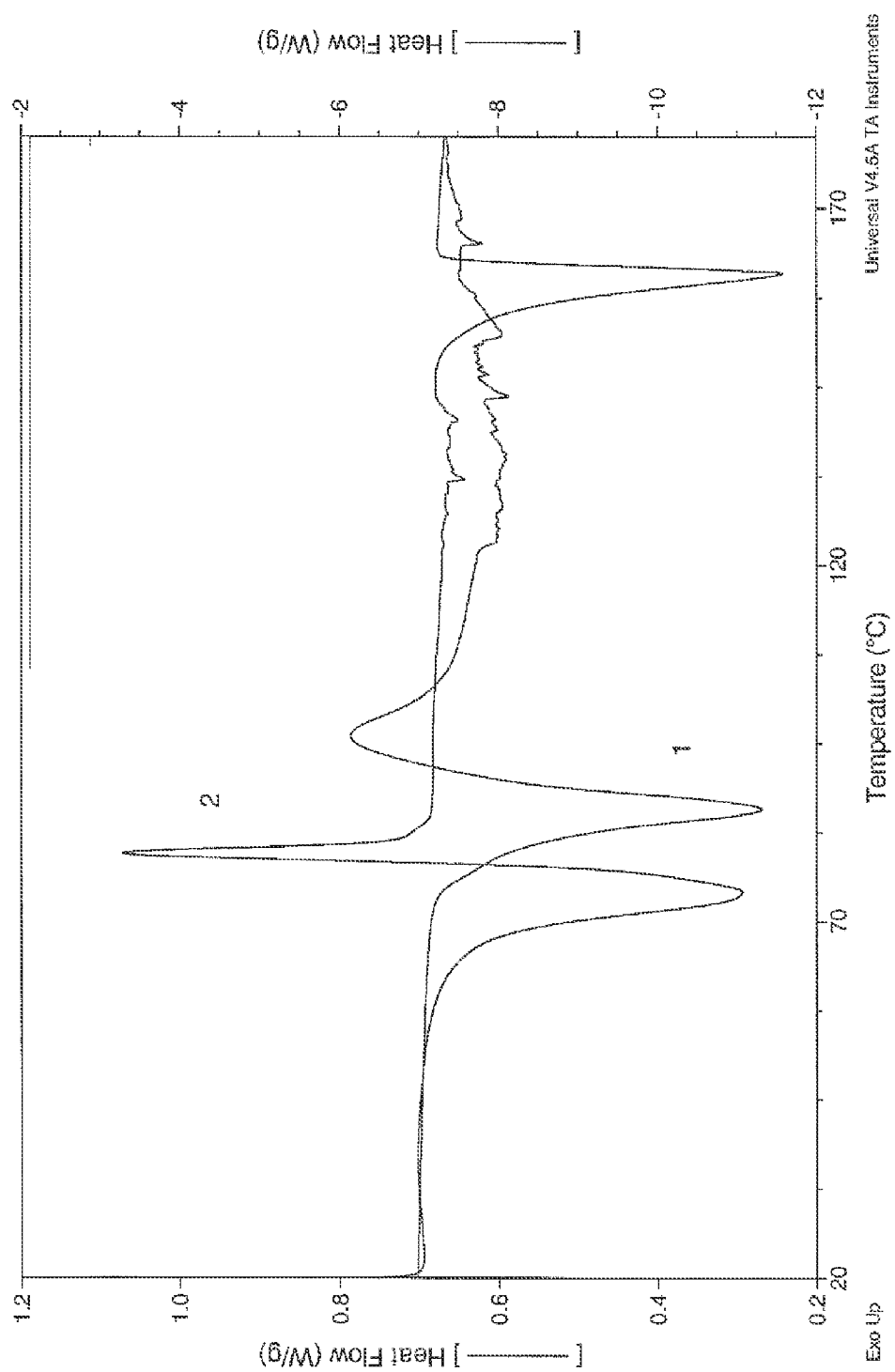
FIG. 6 shows differential scanning calorimetry curves for (2R)-2-phenylcarbonyloxypropyl (2S)-2-amino-3-(3,4-dihydroxyphenyl)propanoate mesylate, hydrate obtained with a temperature ramp of 2° C./min (scan 2) or 20° C./min (scan 1).

As shown in the differential scanning calorimetry scan of FIG. 6, the propensity of the hydrate to recrystallize can depend on the rate of dehydration. A DSC of crystalline (2R)-2-phenylcarbonyloxypropyl (2S)-2-amino-3-(3,4-dihydroxyphenyl)propanoate mesylate, hydrate ramped at 2° C./min shows dehydration of the hydrate and recrystallization to the anhydrous form in the endotherm/exotherm between about 65° C. to about 80° C., and the melt transition of the anhydrous form beginning at about 150° C. A DSC ramped at 20° C./min exhibits an endotherm beginning at about 70° C. and without a strong exotherm characteristic of recrystallization and without a melt transition at higher temperatures, indicating that the anhydrous form failed to recrystallize under these conditions.

Example 9

Sustained Release Tablet Formulations

Different crystalline forms of a compound can have different solid state physical properties that can have an impact on the processability of the compound, the rate of dissolution of the compound from a dosage from, and the stability of the compound. New forms of a pharmaceutically useful compound can provide new opportunities to improve the performance characteristics of a pharmaceutical product and can enlarge the repertoire of materials that a formulation scientist has available for designing, for example, a pharmaceutical dosage form of a drug with a targeted release profile or other desired characteristics. Crystalline (2R)-2-phenylcarbonyloxypropyl (2S)-2-amino-3-(3,4-dihydroxyphenyl)propanoate mesylate, hydrate can be used to provide oral dosage forms with high drug loading, such as a drug loading of at least about 75 wt-% of the total weight of the oral dosage form.

(2R)-2-Phenylcarbonyloxypropyl (2S)-2-amino-3-(3,4-dihydroxyphenyl)propanoate mesylate, hydrate granules prepared according to Example 3, Method 2 (100.5 g) were transferred to a V-shell, 0.5-quart blender, hydroxypropylmethyl cellulose (11.3 g) (HPMC K100M, Dow) was added, and the mixture blended for 6 min. Magnesium stearate (1.13 g) (NF, Mallinckrodt non-bovine) was sieved through a 20-mesh screen, added to the blender, and the contents blended for 5 min. Tablets were prepared from the blend using a Beta press equipped with a 5/16-in standard concave tool and pressed to a hardness of 9-15 kP.

Figure 9:
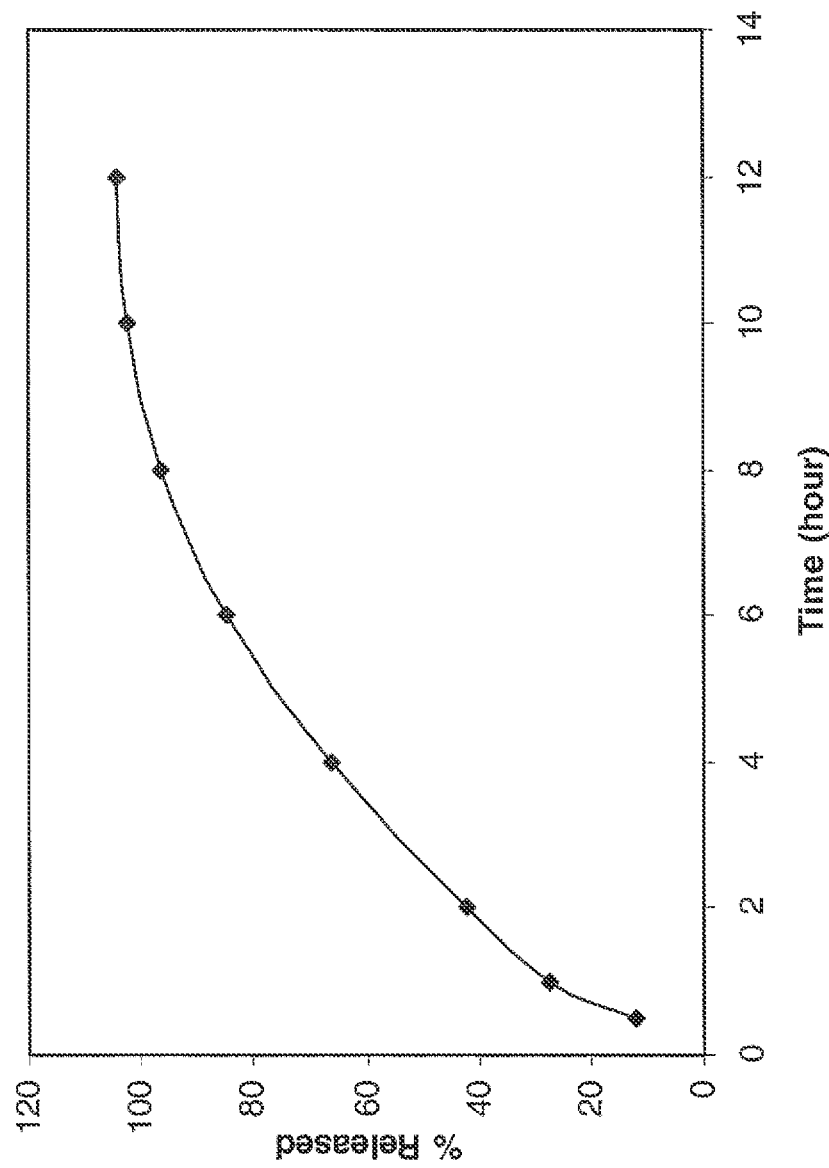
FIG. 9 shows a dissolution profile for sustained release oral table dosage forms comprising (2R)-2-phenylcarbonyloxypropyl (2S)-2-amino-3-(3,4-dihydroxyphenyl)propanoate mesylate, hydrate.

Dissolution profiles for tablets were determined using USP Apparatus 2 (paddles) at a stirring speed of 50 rpm, a temperature of 37° C.±0.5° C. in 900 mL of 0.1N HCl, pH 1.2. Dissolution profiles for the tablets containing 10 wt-% hydroxypropylmethyl cellulose (HPMC K100M, Dow Chemical) prepared according to the above procedure are shown in FIG. 9.

Example 10

Uptake of Levodopa Prodrugs Following Administration of Levodopa Prodrugs and Carbidopa in Rats Sustained release oral dosage forms, which release drug slowly over periods of about 6 to about 24 hours, generally release a significant proportion of the dose within the colon. Thus, drugs suitable for use in such dosage forms should be colonically absorbed. This experiment was conducted to assess the uptake and resultant plasma/blood levels of levodopa, following intracolonic administration of levodopa prodrug mesylate with co-administration of carbidopa (intracolonically, intraperitoneally, or orally), and thereby determine the suitability of levodopa prodrug mesylate for use in an oral sustained release dosage form. Bioavailability of levodopa following co-administration of levodopa prodrug mesylate and carbidopa was calculated relative to oral co-administration of levodopa and carbidopa.

Step A: Administration Protocol

Rats were obtained commercially and were pre-cannulated in the both the ascending colon and the jugular vein. Animals were conscious at the time of the experiment. All animals were fasted overnight and until 4 hours post-dosing of levodopa prodrug. Carbidopa was administered as a solution in water or citrate buffer either orally, intraperitoneally, or intracolonically at a dose equivalent to 25 mg of carbidopa per kg animal weight. Either at the same time or 1 hour after carbidopa dosing, levodopa HCl salt or (2R)-2-phenylcarbonyloxypropyl (2S)-2-amino-3-(3,4-dihydroxyphenyl)propanoate mesylate 1 was administered as a solution (in water) directly into the colon via the cannula at a dose equivalent to 75 mg of levodopa per kg. Blood samples (0.3 mL) were obtained from the jugular cannula at intervals over 8 hours and were immediately quenched with sodium metabisulfite to prevent oxidation of levodopa and levodopa prodrug. Blood was then further quenched with methanol/perchloric acid to prevent hydrolysis of the levodopa prodrug. Blood samples were analyzed as described below.

Step B: Sample Preparation for Colonically Absorbed Drug

Methanol/perchloric acid (300 μL) was added to blank 1.5 mL Eppendorf tubes. Rat blood (300 μL) was collected into EDTA tubes containing 75 μL of sodium metabisulfite at different times and vortexed to mix. A fixed volume of blood (100 μL) was immediately added into the Eppendorf tube and vortexed to mix. Ten microliters of a levodopa standard stock solution (0.04, 0.2, 1, 5, 25, and 100 μg/mL) and 10 μL of the 10% sodium metabisulfite solution was added to 80 μL of blank rat blood to make up calibration standards (0.004, 0.02, 0.1, 0.5, 2.5, and 10 μg/mL). Methanol/perchloric acid (300 μL of 50/50) was then added to each tube followed by the addition of 20 μL of p-chlorophenylalanine. The samples were vortexed and centrifuged at 14,000 rpm for 10 min. The supernatant was analyzed by LC/MS/MS.

Step C: LC/MS/MS Analysis

An API 4000 LC/MS/MS spectrometer equipped with Agilent 1100 binary pumps and a CTC HTS-PAL autosampler were used in the analysis. A Zorbax XDB C8 4.6×150 mm column was used during the analysis. The mobile phases were (A) 0.1% formic acid, and (B) acetonitrile with 0.1% formic acid. The gradient condition was: 5% B for 0.5 min, then to 98% B in 3 min, then maintained at 98% B for 2.5 min. The mobile phase was then returned to 2% B for 2 min. A TurboIonSpray source was used on the API 4000. The analysis was done in positive ion mode and the MRM transition for each analyte was optimized using standard solution. Five (5) μL of each sample was injected. Non-compartmental analysis was performed using WinNonlin software (v.3.1 Professional Version, Pharsight Corporation, Mountain View, Calif.) on individual animal profiles. Summary statistics on major parameter estimates was performed for $C_{max}$ (peak observed concentration following dosing), $T_{max}$ (time to maximum concentration is the time at which the peak concentration was observed), $AUC_{(0-t)}$ (area under the serum concentration-time curve from time zero to last collection time, estimated using the log-linear trapezoidal method), $AUC_{(0-\infty)}$ (area under the blood concentration time curve from time zero to infinity, estimated using the log-linear trapezoidal method to the last collection time with extrapolation to infinity), and $t_{1/2,z}$ (terminal half-life).

Maximum concentrations of levodopa in the blood ($C_{max}$ values) and the area under blood concentration versus time curve (AUC) values after intracolonic dosing of (2R)-2-phenylcarbonyloxypropyl (2S)-2-amino-3-(3,4-dihydroxyphenyl)propanoate mesylate 1 with carbidopa were significantly higher (>2-fold) than those achieved for colonic administration of levodopa with carbidopa.

Intracolonic co-administration of levodopa and carbidopa results in very low relative bioavailability of levodopa (i.e., only 3% of orally co-administered levodopa and carbidopa). By comparison, co-administration of (2R)-2-phenylcarbonyloxypropyl (2S)-2-amino-3-(3,4-dihydroxyphenyl)propanoate mesylate 1 with carbidopa exhibited improved relative bioavailability of levodopa by at least 2-fold. The data demonstrates that certain levodopa prodrugs can be formulated as compositions suitable for effective sustained oral release and uptake of levodopa prodrug mesylate and/or levodopa from the colon.

Similar procedures can be used to assess the oral and colonic bioavailability of levodopa administered as (2R)-2-phenylcarbonyloxypropyl (2S)-2-amino-3-(3,4-dihydroxyphenyl)propanoate mesylate, hydrate.

Example 11

Use of Crystalline (2R)-2-Phenylcarbonyloxypropyl (2S)-2-Amino-3-(3,4-dihydroxyphenyl)propanoate Mesylate, Hydrate for Treating Parkinson's Disease The following clinical study may be used to assess the efficacy of (2R)-2-phenylcarbonyloxypropyl (2S)-2-amino-3-(3,4-dihydroxyphenyl)propanoate mesylate, hydrate in treating Parkinson's disease.

Patients with idiopathic PD fulfilling the Queen Square Brain Bank criteria (Gibb et al., *J Neurol Neurosurg Psychiatry* 1988, 51, 745-752) with motor fluctuations and a defined short duration levodopa response (1.5-4 hours) are eligible for inclusion. Clinically relevant peak dose dyskinesias following each morning dose of their current medication are a further pre-requisite. Patients are also required to have been stable on a fixed dose of treatment for a period of at least one month prior to starting the study. Patients are excluded if their current drug regime includes slow-release formulations of levodopa, COMT inhibitors, selegiline, anticholinergic drugs, or other drugs that could potentially interfere with gastric absorption (e.g. antacids). Other exclusion criteria include patients with psychotic symptoms or those on antipsychotic treatment patients with clinically relevant cognitive impairment, defined as MMS (Mini Mental State) score of less than 24 (Folstein et al., *J Psychiatr Res* 1975, 12, 189-198), risk of pregnancy, Hoehn & Yahr stage 5 in off-status, severe, unstable diabetes mellitus, and medical conditions such as unstable cardiovascular disease or moderate to severe renal or hepatic impairment. Full blood count, liver, and renal function blood tests are taken at baseline and after completion of the study.

A randomized, double-blind, and cross-over study design are used. Each patient is randomized to the order in which either LD/DC or one of the two dosages of test compound is administered in a single-dose challenge in double-dummy fashion in three consecutive sessions. Randomization is by computer generation of a treatment number allocated to each patient according to the order of entry into the study.

Patients are admitted to a hospital for an overnight stay prior to administration of (2R)-2-phenylcarbonyloxypropyl (2S)-2-amino-3-(3,4-dihydroxyphenyl)propanoate mesylate, hydrate the next morning on three separate occasions at weekly intervals. After withdrawal of all anti-parkinsonian medication from midnight the previous day (2R)-2-phenylcarbonyloxypropyl (2S)-2-amino-3-(3,4-dihydroxyphenyl)

propanoate mesylate, hydrate is administered at exactly the same time in the morning in each patient under fasting conditions.

Patients are randomized to the order of the days on which they receive placebo or (2R)-2-phenylcarbonyloxypropyl (2S)-2-amino-3-(3,4-dihydroxyphenyl)propanoate mesylate, hydrate. The pharmacokinetics of crystalline mesylate hydrate may be assessed by monitoring plasma levodopa concentration over time. Prior to administration, a 22 G intravenous catheter is inserted in a patient's forearm. Blood samples of 5 mL each are taken at baseline and at 15, 30, 45, 60, 75, 90, 105, 120, 140, 160, 180, 210, and 240 minutes after administering (2R)-2-phenylcarbonyloxypropyl (2S)-2-amino-3-(3,4-dihydroxyphenyl)propanoate mesylate, hydrate or until a full off-state has been reached if this occurs earlier than 240 minutes after drug ingestion. Samples are centrifuged immediately at the end of each assessment and stored deep frozen until assayed. Plasma levodopa and 3-O-methyl-Dopa levels are assessed by high-pressure liquid chromatography (HPLC). On the last assessment additional blood may be drawn for assessment of hematology, blood sugar, liver, and renal function.

For clinical assessment, motor function is assessed using UPDRS (United Parkinson's Disease Rating Scale) motor score and BrainTest (Giovanni et al., *J Neurol Neurosurg Psychiatry* 1999, 67, 624-629), which is a tapping test performed with a patient's more affected hand on the keyboard of a laptop computer. These tests are carried out at baseline and then immediately following each blood sampling until the patient reaches their full on-stage, and thereafter at 3 intervals of 20 min, and 30 min intervals until the patient reaches their baseline off-status. Once a patient reaches their full on-state, video recordings are performed three times at 20 min intervals. The following mental and motor tasks, which have been shown to increase dyskinesia (Duriff et al., *Mov Disord* 1999, 14, 242-245), are monitored during each video session: (1) sitting still for 1 minute; (2) performing mental calculations; (3) putting on and buttoning a coat; (4) picking up and drinking from a cup of water; and (5) walking. Videotapes are scored using, for example, versions of the Goetz Rating Scale and the Abnormal Involuntary Movements Scale to document a possible increase in test compound induced dyskinesia.

Actual occurrence and severity of dyskinesia can be measured with a Dyskinesia Monitor (Manson et al., *J Neurol Neurosurg Psychiatry* 2000, 68, 196-201). The device is taped to a patient's shoulder on their more affected side. The monitor records during the entire time of a challenging session and provides a measure of the frequency and severity of occurring dyskinesias.

Results can be analyzed using appropriate statistical methods.

Example 12

Clinical Trial to Determine the Pharmacokinetics and Safety of (2R)-2-Phenylcarbonyloxypropyl (2S)-2-amino-3-(3,4-dihydroxyphenyl)propanoate Mesylate, Hydrate An open-label, single-center, randomized, 3-treatment, 3-period, single-dose clinical study can be used to assess the PK and safety of pharmaceutical compositions comprising of (2R)-2-phenylcarbonyloxypropyl (2S)-2-amino-3-(3,4-dihydroxyphenyl)propanoate mesylate, hydrate (administered with Lodosyn® (carbidopa)) compared with Sinemet® (L-dopa and carbidopa) in healthy adult subjects. Treatments are administered in both fasted and fed conditions.

Prior to initial dosing on Day −1 of Period 1, 24 subjects are randomized to one of two parallel groups using a 1:1 allocation. Subjects assigned to Group 1 are randomized to one of two 2-period sequences (AB or BA) to examine formulation effect in the fasted state. Subjects assigned to Group 2 are randomized to one of two 2-period sequences (AB or BA) to examine formulation effect in the fed state. Subjects will receive Treatment C in the third period in either the fasted (Group 1) or the fed (Group 2) state. Subjects will also receive 50 mg (2×25 mg) Lodosyn® tablets at −24, −12, 12 and 24 hours post Treatments A-C.

Subjects in Group 1 (Fasted) receive Treatment A: 2×SR2 Tablets (sustained release tablet 2 comprising (2R)-2-phenylcarbonyloxypropyl (2S)-2-amino-3-(3,4-dihydroxyphenyl)propanoate mesylate, hydrate)+50 mg (2×25 mg) Lodosyn® Tablets; Treatment B: 2×SR3 Tablets (sustained release tablet 3 comprising (2R)-2-phenylcarbonyloxypropyl (2S)-2-amino-3-(3,4-dihydroxyphenyl)propanoate mesylate, hydrate)+50 mg (2×25 mg) Lodosyn® Tablets; and Treatment C: 200 mg (2×25/100 mg) Sinemet® Tablets. Subjects in treatment Group 2 (Fed) receive Treatment A: 2×SR2 Tablets+50 mg (2×25 mg) Lodosyn® Tablets; Treatment B: 2×SR3 Tablets+50 mg (2×25 mg) Lodosyn® Tablets; and Treatment C: 200 mg (2×25/100 mg) Sinemet® Tablets.

Subjects begin screening within 16 days of checking into the clinic for Period 1. For Period 1-3, subjects check into the clinic on Day −2, and remain on site until check out (Day 2, 36 hours post-dose) after the last blood draw. Periods 1 through 3 last approximately 3 weeks, during which subjects are confined to the clinic for approximately 4 days (Day −2 thru Day 2) during each Period, for a total of 12 days of confinement. Following discharge from Periods 1 and 2, subjects complete a washout period of approximately 1 week, which starts on Day 1 after administration of the morning Treatment. A final follow-up visit occurs 5-7 days after clinic discharge for Period 3.

All subjects fast overnight on Day −1 for approximately 10 hours. Fasted treatments (Treatments A, B and C for Group 1) are administered following the 10-hour overnight fast. Fed treatments (Treatments A, B, and C for Group 2) are administered within 10 minutes of completion of a high fat breakfast (ca. 50% calories from fat; ca. 800-1000 total kcals). Lodosyn® tablets at −24, −12 (pre-dose to Day 1), 12, and 24 hours post Treatments A-C are administered following a moderate fat meal.

Blood and urine are collected at intervals up to 36 hours post-dose beginning on Day 1 of each period.

On Day 1, subjects dosing under fed conditions are served a high-fat (ca. 50 percent of total caloric content of the meal) and high-calorie (ca. 800 to 1000 calories) meal for breakfast (e.g., 2 eggs fried in butter, 2 strips bacon, 2 slices of wheat toast with butter, 4 ounces of hash brown potatoes, and 9 ounces of whole milk), ca. 30 minutes prior to dosing. The test meal is to derive approximately 150, 250, and 500-600 calories from protein, carbohydrate, and fat, respectively. Subjects must consume the entire meal. Within 10 minutes of consumption of the high fat breakfast, subjects receive the dose of the study drug with 240 mL of non-carbonated water. All other meals (dinner on Day −2, breakfast, lunch, and dinner on Day −1, lunch and dinner of Day 1 and breakfast, lunch and dinner on Day 2) are standardized clinic meals (approximately 30% calories from fat). Subjects may be served an optional snack after dinner.

Blood (4 mL per sample) is taken from subjects for estimation of pharmacokinetic parameters. Blood samples are quenched for determination of concentrations of (2R)-2-phenylcarbonyloxypropyl (2S)-2-amino-3-(3,4-dihydroxyphenyl)propanoate mesylate, of (2R)-2-phenylcarbonyloxypropyl (2S)-2-amino-3-(3,4-dihydroxyphenyl)propanoate, levodopa, 3-O-methyldopa, carbidopa, and other metabolites. The following PK parameters are estimated using non-compartmental methods: peak concentration ($C_{max}$), time to peak concentration ($T_{max}$), concentration at 12 hr post-dose ($C_{12}$), terminal elimination rate constant (Kel) and half-life ($T_{max}$), and area under the concentration-time curve (AUC).

Urine is collected and analyzed for determination of concentrations of levodopa and other metabolites. The following are estimated: the amount of the analyte excreted in urine during each collection interval ($Ae_{(0-t)}$), the amount of the analyte excreted in urine during the 36-hour post-dose interval ($Ae_{(0-36)}$), and the cumulative percentage of dose excreted in urine up to 36 hours post-dose (% dose excreted).

Data from all study periods can be analyzed using appropriate statistical methods.

Example 13

Figure 10:
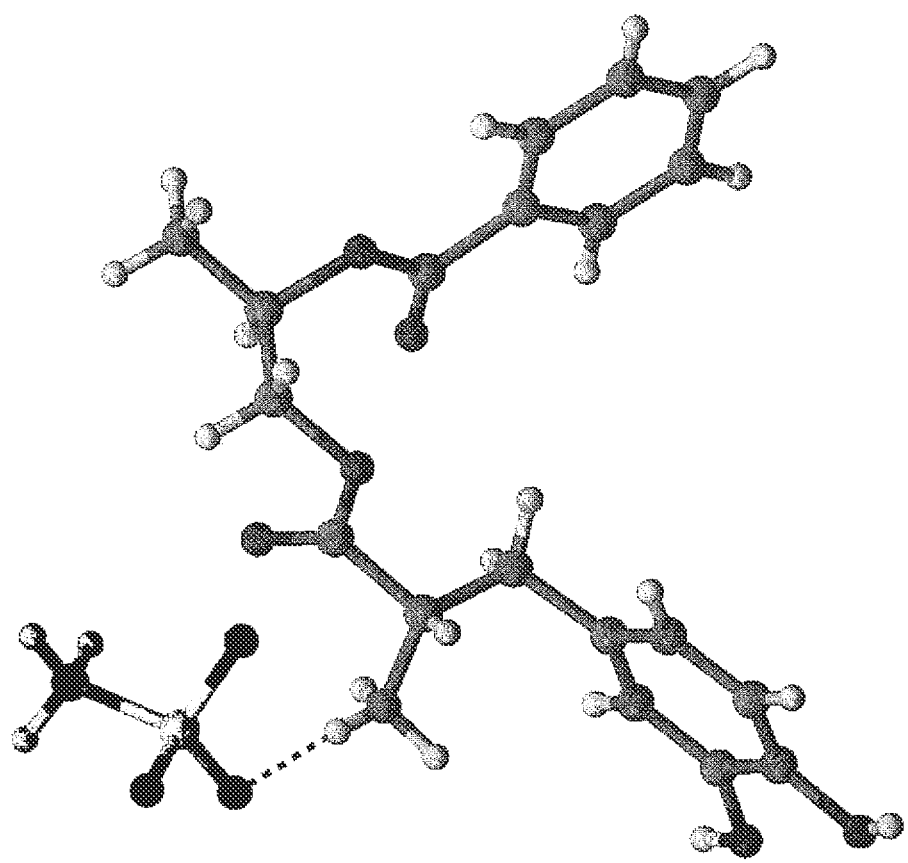
FIG. 10 shows the molecular structure and conformation of anhydrous (2R)-2-phenylcarbonyloxypropyl (2S)-2-amino-3-(3,4-dihydroxyphenyl)propanoate mesylate.
Figure 11:
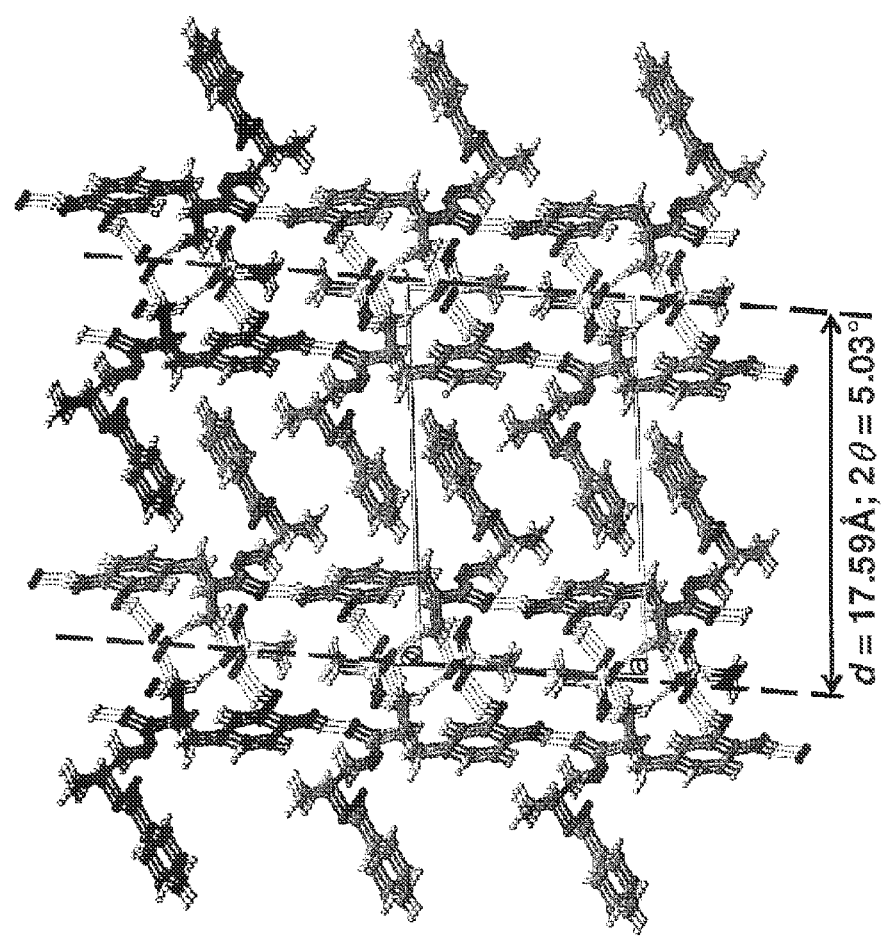
FIG. 11 shows the layered crystal structure of anhydrous (2R)-2-phenylcarbonyloxypropyl (2S)-2-amino-3-(3,4-dihydroxyphenyl)propanoate mesylate.

Crystal Structures of Anhydrous and Hydrate Forms of (2R)-2-Phenylcarbonyloxypropyl (2S)-2-amino-3-(3,4-dihydroxyphenyl)propanoate mesylate Crystal structures of anhydrous and hydrate forms were determined to evaluate the molecular structures, conformations, overall packing and arrangements of groups at the possible crystal faces. The X-ray data was collected at $-173°$ C. The anhydrous form of (2R)-2-phenylcarbonyloxypropyl (2S)-2-amino-3-(3,4-dihydroxyphenyl)propanoate mesylate crystallizes in the chiral space group $P2_1$ (Table 1) with one molecule in the asymmetric unit. The structure of the asymmetric unit with the conformation of the drug molecule is shown in FIG. 10. The mesylate anion and the —$NH_3^+$ group of the drug are connected to each other through strong charge-assisted N—H . . . O hydrogen bonds. In addition, the hydroxyl groups of the catechol moiety are bonded to the mesylate anion and the ester carbonyl groups through N—H . . . O hydrogen bonds. This packing leads to an overall layered structure with distinct hydrogen bonding domains and domains containing aromatic groups (FIG. 11). The structure exhibits a packing fraction of 0.681 and inter-connected cavities down the b-axis in the vicinity of aromatic domains.

TABLE 1

Crystal data for anhydrous levodopa prodrug mesylate.

| Formula | $C_{19}H_{22}NO_6:CH_3O_3S$ |
|---|---|
| Crystal System | Monoclinic |
| Space group | $P2_1$ (No. 4) |
| a, b, c [Å] | 10.4410(4), 5.9120(2), 17.6530(8) |
| α, β, γ [°] | 90, 94.826(2), 90 |
| V [Å$^3$] | 1085.81(7) |
| Z | 2 |
| $D_{calc}$ [g cm$^{-3}$] | 1.393 |

Figure 12:
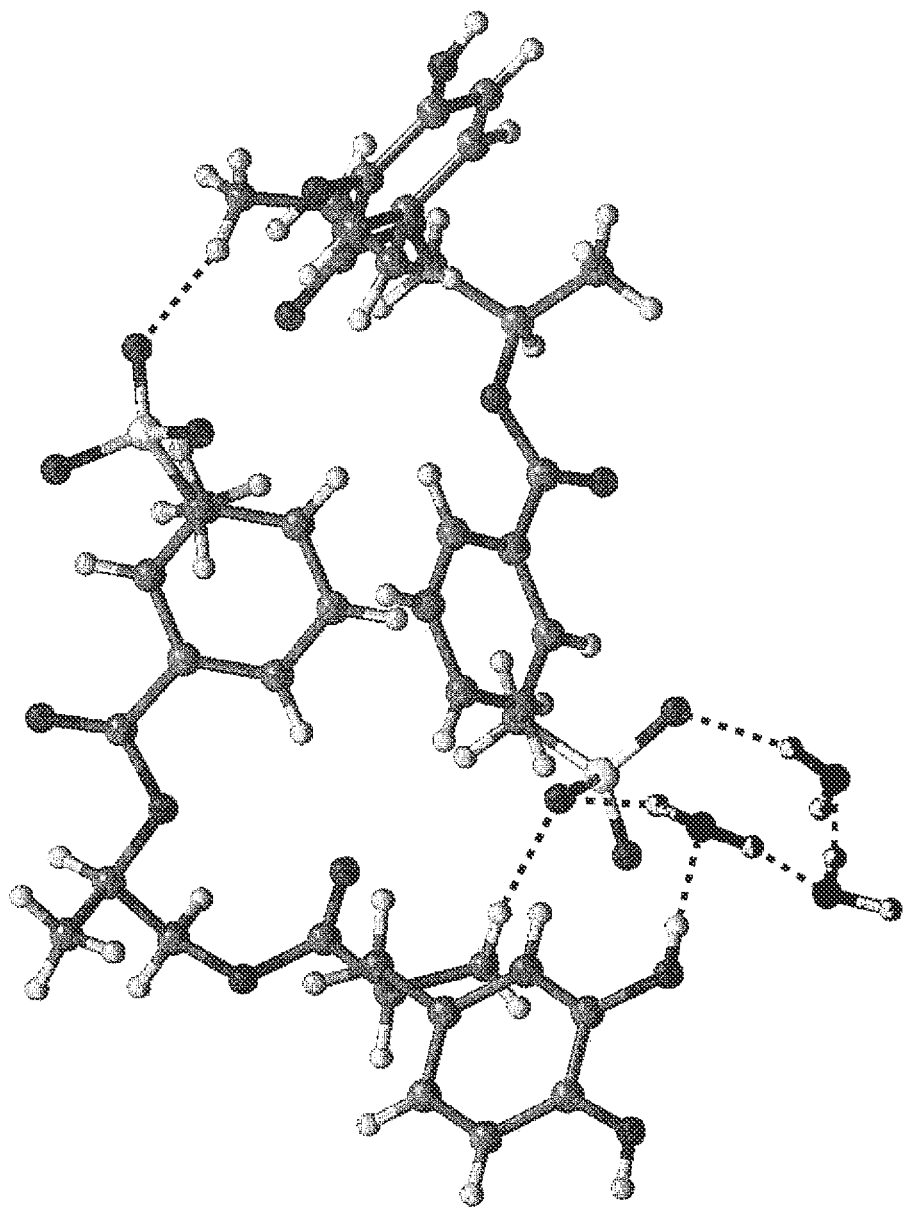
FIG. 12 shows the asymmetric unit lattice of (2R)-2-phenylcarbonyloxypropyl (2S)-2-amino-3-(3,4-dihydroxyphenyl)propanoate mesylate, hydrate showing two symmetry independent drug molecules, mesylate anions and three symmetry independent water molecules.
Figure 13:
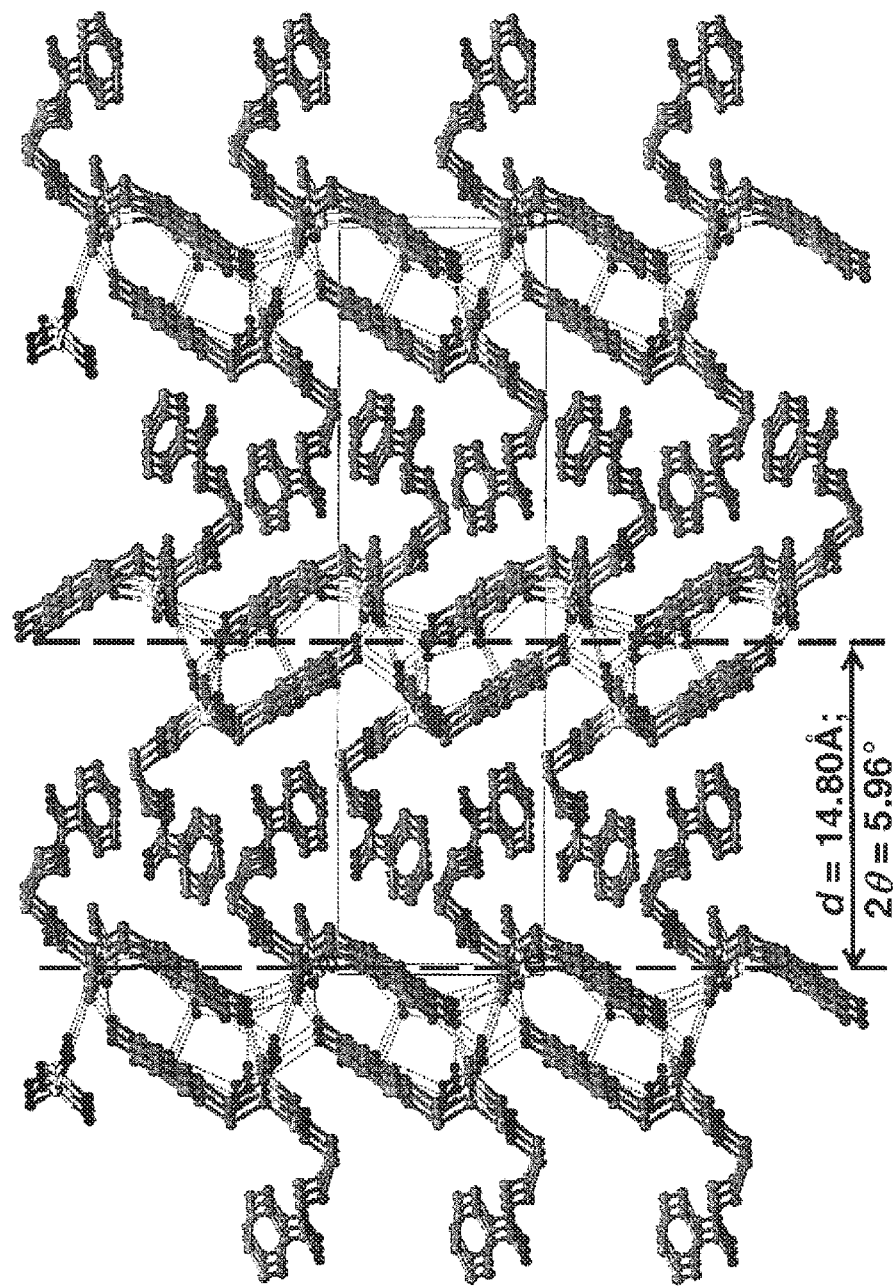
FIG. 13 shows the layered crystal structure of (2R)-2-phenylcarbonyloxypropyl (2S)-2-amino-3-(3,4-dihydroxyphenyl)propanoate mesylate, hydrate.

The hydrate form of (2R)-2-phenylcarbonyloxypropyl (2S)-2-amino-3-(3,4-dihydroxyphenyl)propanoate mesylate also crystallizes in the chiral space group $P2_1$ (Table 2). The lattice structure contains two symmetry independent mesylate salt species and three symmetry independent water molecules, giving an overall 1:1.5 stoichiometry between the compound and water. The structure of the asymmetric unit with the conformations and some inter-component hydrogen bonds is shown in FIG. 12. While independent (2R)-2-phenylcarbonyloxypropyl (2S)-2-amino-3-(3,4-dihydroxyphenyl)propanoate mesylate molecules still adopt bent conformations, the conformation in the anhydrous form is more compact compared to the ones in the hydrate. As in the anhydrous form, the —$NH_3^+$ and —OH groups participate in hydrogen bonding. In the hydrated form, however, the hydrogen bond pattern is different due to the insertion of water molecules in the hydrogen bond network. The hydrate also forms a layered structure (FIG. 13) with polar domains containing charged groups and hydrogen bonds and aromatic domains containing phenyl groups. The structure of the hydrate form has slightly higher density (1.411 g cm$^{-3}$) and packing fraction (69.7%) compared to the anhydrous form. The slightly enlarged conformation of the molecules and added water molecules in the lattice lead to a larger d-spacing for the interlayer distance in the hydrate.

TABLE 2

Crystal data for levodopa prodrug mesylate, hydrate.

| Formula | $2(C_{19}H_{22}NO_6):2(CH_3O_3S):3H_2O$ |
|---|---|
| Crystal System | Monoclinic |
| Space group | $P2_1$ (No. 4) |
| a, b, c [Å] | 8.1519(1), 29.5903(4), 9.4261(1) |
| α, β, γ [°] | 90, 92.415(1), 90 |
| V [Å$^3$] | 2271.72(5) |
| Z | 2 |
| $D_{calc}$ [g cm$^{-3}$] | 1.411 |

Finally, it should be noted that there are alternative ways of implementing the embodiments disclosed herein. Accordingly, the present embodiments are to be considered as illustrative and not restrictive. Furthermore, the claims are not to be limited to the details given herein, and are entitled their full scope and equivalents thereof.

What is claimed is:

1. A method of treating a disease in a patient comprising administering to a patient in need of such treatment a therapeutically effective amount of a compound crystalline (2R)-2-phenylcarbonyloxypropyl (2S)-2-amino-3-(3,4-dihydroxyphenyl)propanoate mesylate, hydrate, which exhibits characteristic scattering angles (2θ) at least at 6.0°±0.2°, 9.1°±0.2°, 14.6°±0.2°, 16.1°±0.2°, 16.6°±0.2°, and 18.5°±0.2° in an X-ray powder diffraction pattern measured using Cu—K$_α$ radiation, wherein the disease is chosen from Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, and excessive daytime sleepiness.

2. The method of claim 1, wherein the compound exhibits characteristic scattering angles (2θ) at least at 6.0°±0.2°, 9.1°±0.2°, 9.6°±0.2°, 12.0°±0.2°, 13.8°±0.2°, 14.6°±0.2°, 15.1°±0.2°, 15.6°±0.2°, 16.1°±0.2°, 16.6°±0.2°, 17.6°±0.2°, 18.5°±0.2°, and 19.2°±0.2° in an X-ray powder diffraction pattern measured using Cu—K$_α$ radiation.

3. The method of claim 1, wherein the compound exhibits characteristic scattering angles (2θ) at least at 6.0°±0.2°, 9.1°±0.2°, 9.6°±0.2°, 12.0°±0.2°, 13.8°±0.2°, 14.6°±0.2°, 15.1°±0.2°, 15.6°±0.2°, 16.1°±0.2°, 16.6°±0.2°, 17.6°±0.2°, 18.5°±0.2°, 19.2°±0.2°, 20.8°±0.2°, 21.9°±0.2°, 22.8°±0.2°, 23.4°±0.2°, 23.7°±0.2°, 23.9°±0.2°, and 26.5°±0.2° in an X-ray powder diffraction pattern measured using Cu—K$_α$ radiation.

4. The method of claim 1, wherein the compound exhibits characteristic scattering angles (2θ) at least at 6.0°±0.2°, 9.1°±0.2°, 9.6°±0.2°, 11.2°±0.2°, 12.0°±0.2°, 12.8°±0.2°, 13.8°±0.2°, 14.3°±0.2°, 14.6°±0.2°, 15.1°±0.2°, 15.6°±0.2°, 16.1°±0.2°, 16.6°±0.2°, 17.6°±0.2°, 18.5°±0.2°, 18.7°±0.2°, 19.2°±0.2°, 20.5°±0.2°, 20.8°±0.2°, 21.1°±0.2°, 21.9°±0.2°, 22.8°±0.2°, 23.4°±0.2°, 23.7°±0.2°, 23.9°±0.2°, 24.7°±0.2°, 26.5°±0.2°, 28.2°±0.2°, 28.3°±0.2°, and 29.5°±0.2° in an X-ray powder diffraction pattern measured using Cu—K$_\alpha$ radiation.

5. The method of claim 1, wherein the compound comprises from about 1.4 moles water to about 1.6 moles water to mole of the compound.

6. The method of claim 1, wherein the compound comprises from about 5.3 wt-% to about 5.7 wt-% water.

7. The method of claim 1, wherein the compound is prepared by a process comprising processing (2R)-2-phenylcarbonyloxypropyl (2S)-2-amino-3-(3,4-dihydroxyphenyl)propanoate mesylate by high shear wet granulation using a water content ranging from about 10 wt-% to about 20 wt-% to provide granules comprising the crystalline (2R)-2-phenylcarbonyloxypropyl (2S)-2-amino-3-(3,4-dihydroxyphenyl) propanoate mesylate, hydrate.

8. The method of claim 1, wherein the compound is prepared by a process comprising: dissolving (2R)-2-phenylcarbonyloxypropyl (2S)-2-amino-3-(3,4-dihydroxyphenyl)propanoate mesylate in a solvent comprising water to form a solution, wherein the water activity in the solvent is greater than about 0.6; and crystallizing the (2R)-2-phenylcarbonyloxypropyl (2S)-2-amino-3-(3,4-dihydroxyphenyl)propanoate mesylate to provide the crystalline (2R)-2-phenylcarbonyloxypropyl (2S)-2-amino-3-(3,4-dihydroxyphenyl) propanoate mesylate, hydrate.

9. The method of claim 1, wherein the solvent comprises isopropanol and at least about 7%-bv water.

10. The method of claim 1, wherein the disease is Parkinson's disease.

11. The method of claim 1, wherein the therapeutically effective amount of (2R)-2-phenylcarbonyloxypropyl (2S)-2-amino-3-(3,4-dihydroxyphenyl)propanoate mesylate, hydrate is from about 200 mg to about 7 g per day.

12. A method of treating a disease in a patient comprising administering to a patient in need of such treatment a pharmaceutical composition comprising a therapeutically effective amount of a compound crystalline (2R)-2-phenylcarbonyloxypropyl (2S)-2-amino-3-(3,4-dihydroxyphenyl) propanoate mesylate, hydrate, which exhibits characteristic scattering angles (2θ) at least at 6.0°±0.2°, 9.1°±0.2°, 14.6°±0.2°, 16.1°±0.2°, 16.6°±0.2°, and 18.5°±0.2° in an X-ray powder diffraction pattern measured using Cu—K$_\alpha$ radiation, wherein the disease is chosen from Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, and excessive daytime sleepiness.

13. The method of claim 12, wherein the pharmaceutical composition comprises an L-aromatic amino acid decarboxylase inhibitor.

14. The method of claim 12, wherein the pharmaceutical composition comprises a catechol-O-methyltransferase inhibitor.

15. The method of claim 12, wherein the pharmaceutical composition is formulated for sustained release oral administration.

16. A method of treating a disease in a patient comprising administering to a patient in need of such treatment an oral dosage form comprising a therapeutically effective amount of a compound crystalline (2R)-2-phenylcarbonyloxypropyl (2S)-2-amino-3-(3,4-dihydroxyphenyl)propanoate mesylate, hydrate, which exhibits characteristic scattering angles (2θ) at least at 6.0°±0.2°, 9.1°±0.2°, 14.6°±0.2°, 16.1°±0.2°, 16.6°±0.2°, and 18.5°±0.2° in an X-ray powder diffraction pattern measured using Cu—K$_\alpha$ radiation, wherein the disease is chosen from Parkinson's disease, depression, attention deficit disorder, schizophrenia, manic depression, cognitive impairment disorders, restless legs syndrome, periodic limb movement disorders, tardive dyskinesia, Huntington's disease, Tourette's syndrome, hypertension, addictive disorders, congestive heart failure, and excessive daytime sleepiness.

17. The method of claim 16, wherein the oral dosage form comprises an L-aromatic amino acid decarboxylase inhibitor.

18. The method of claim 16, wherein the oral dosage form comprises a catechol-O-methyltransferase inhibitor.

19. The method of claim 16, wherein the oral dosage form is a sustained release oral form.

* * * * *